(12) United States Patent
Webb et al.

(10) Patent No.: US 10,876,116 B2
(45) Date of Patent: Dec. 29, 2020

(54) ANTI-ARID3A TREATMENTS FOR INFLAMMATORY DISORDERS

(71) Applicant: The Board of Regents of the University of Oklahoma, Norman, OK (US)

(72) Inventors: Carol F. Webb, Oklahoma City, OK (US); Julie Ward, Franklin, MA (US); Michelle Ratliff, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 16/317,719

(22) PCT Filed: Jul. 14, 2017

(86) PCT No.: PCT/US2017/042119
§ 371 (c)(1),
(2) Date: Jan. 14, 2019

(87) PCT Pub. No.: WO2018/013912
PCT Pub. Date: Jan. 18, 2018

(65) Prior Publication Data
US 2019/0345493 A1 Nov. 14, 2019

Related U.S. Application Data

(60) Provisional application No. 62/362,775, filed on Jul. 15, 2016.

(51) Int. Cl.
*C12N 15/113* (2010.01)
*A61P 37/02* (2006.01)
*A61P 31/12* (2006.01)

(52) U.S. Cl.
CPC ............ *C12N 15/113* (2013.01); *A61P 31/12* (2018.01); *A61P 37/02* (2018.01); *C12N 2310/11* (2013.01); *C12N 2310/314* (2013.01); *C12N 2310/3233* (2013.01); *C12N 2310/351* (2013.01)

(58) Field of Classification Search
None
See application file for complete search history.

(56) References Cited

U.S. PATENT DOCUMENTS

| 7,595,302 | B2 | 9/2009 | Dutreix et al. | |
|---|---|---|---|---|
| 2005/0048464 | A1* | 3/2005 | Tian | A61P 1/16 435/4 |
| 2005/0271651 | A1 | 12/2005 | Webb | |
| 2008/0234183 | A1 | 9/2008 | Hallbrink et al. | |
| 2010/0008891 | A1 | 1/2010 | Webb et al. | |
| 2014/0187605 | A1 | 7/2014 | van Nieuw Amerongen et al. | |
| 2014/0350071 | A1* | 11/2014 | Sehgal | A61P 1/16 514/44 A |

FOREIGN PATENT DOCUMENTS

| EP | 1752536 A1 | 2/2007 | |
|---|---|---|---|
| WO | 2010009015 A2 | 1/2010 | |
| WO | 2014193611 A1 | 12/2014 | |
| WO | 2017010950 A1 | 1/2017 | |
| WO | WO-2017010950 A1 * | 1/2017 | .............. A61P 31/20 |

OTHER PUBLICATIONS

Fang et al (Digestive Diseases and Sciences, 39( 9):2014-2021, 1994) (Year: 1994).*
Pratama, et al.; "Critical role of ARID3B in the Expression of Pro-Apoptotic p53-target Genes and Apoptosis," Biochemcial and Biophysical Research Communications (2015), 468:248-254.
Lestari, et al.; "Cooperation Between ARID3A and p53 in the Transcriptional Activation of p21WAF1 in Response to DNA Damage," Biochemical and Biophysical Research Communications (2011), 417:710-716.
An, et al,; "Loss of Bright/ARID3a Function Promotes Developmental Plasticity," Stem Cells (2010) 28:1560-1567.
Ratliff, et al.; "The Transcription Factor ARID3a is important for In Vitro Differentiation of Human Hematopietic Progenitors," The Journal of Immunology (2015) 196:614-623.
Ward, et al.; "Human Effector B Lymphocytes Express ARID3a and Secrete Interferon Alpha," Journal of Autoimmunity (2016) 75:130-140.
EP17828525.0; Webb, et al. European Search Report dated Mar. 11, 2020, filed Jul. 14, 2017.
International Search Report, dated Dec. 12, 2017, in PCT/US2017/042119, filed Jul. 14, 2017.
Written Opinion of the International Searching Authority, dated Dec. 12, 2017, in PCT/US2017/042119, filed Jul. 14, 2017.
Crow, Mary K.; "Type I Interferon in the Pathogenesis of Lupus." Journal of Immunology, (2014); vol. 192, pp. 5459-5468.
Kimura, et al.; "Stabilization of Human Interferon-α1 mRNA by its Antisense RNA," Cellular and Molecular Life Sciences, (available Dec. 8, 2012), vol. 70, pp. 1451-1467.
Kim, G.; "Determinants of Embryonic Hematopoietic Stem Cell Emergence and Maturation," Doctoral Dissertation, Harvard Medical School, Dec. 31, 2015; pp. 1-116; retrieved from the Internet:<http://nrs.harvard.edu/urn-3:HUL.InstRepos:15821585> on Nov. 9, 2016, entire document.
EP Appl. No. 17828525.0; Webb, et al.; filed Jul. 14, 2017; Extended European Search Report dated Jun. 25, 2020.

* cited by examiner

*Primary Examiner* — Richard A Schnizer
(74) *Attorney, Agent, or Firm* — Dunlap Codding, P.C.

(57) ABSTRACT

Antisense compounds for suppressing expression of ARTD3a are disclosed, as well as pharmaceutical compositions containing same and methods of producing and using same. The antisense compounds can be used to treat inflammatory disorders and conditions related to interferon-alpha production.

17 Claims, 33 Drawing Sheets
Specification includes a Sequence Listing.

ANTI-ARID3A TREATMENTS FOR INFLAMMATORY DISORDERS

CROSS-REFERENCE TO RELATED APPLICATIONS/INCORPORATION BY REFERENCE STATEMENT

This patent application is a US national stage application filed under 35 USC § 371 of International Application No. PCT/US2017/042119, filed Jul. 14, 2017; which claims benefit under 35 U.S.C. § 119(e) of provisional patent application U.S. Ser. No. 62/362,775, filed on Jul. 15, 2016. The contents of the above-referenced applications are expressly incorporated herein by reference.

STATEMENT REGARDING FEDERALLY SPONSORED RESEARCH OR DEVELOPMENT

This invention was made with government support under Grant number A1118836 awarded by the National Institutes of Health. The government has certain rights in the invention.

BACKGROUND

Certain inflammatory disorders have been related to increased levels of the cytokine interferon alpha (IFN-alpha), and are sometimes referred to as interferonopathies. Systemic lupus erythemnatosus (SLE) for example is a chronic autoimmune disease resulting from breaches in immune tolerance and characterized by anti-nuclear antibody (ANA) production and waves of inflammation. ANAs form complexes with antigens and deposit in several organ systems resulting in inflammation, immune cell activation, and organ damage. Although SLE is common, the underlying causes are unknown, making it difficult to find a unifying explanation for the complex molecular abnormalities that arise in these patients. To date, there has not been a unifying biomarker predictive of susceptibility or disease activity among SLE patients, and the clinically diverse nature of SLE has further complicated the identification of new biomarkers that might lead to better treatments.

Approximately half of SLE patients exhibit increased levels of IFN-alpha, and these levels have been associated with inflammation and disease activity in SLE. Elevated IFN-alpha levels result in increased expression of multiple IFN-alpha-responsive genes in SLE peripheral blood cells, collectively referred to as an "interferon signature."

Current biologic treatments for lupus include ablation of all types of immune cells through immunosuppressive therapies, ablation of all antibody-generating B cells, and trials to directly block interferon alpha using anti-interferon antibodies. However, none of these treatments have been effective in eliminating disease activity, and they typically are associated with disadvantages associated with immunosuppression.

BRIEF DESCRIPTION OF DRAWINGS

Several embodiments of the present disclosure are hereby illustrated in the appended drawings. It is to be noted however, that the appended drawings only illustrate several embodiments and are therefore not intended to be considered limiting of the scope of the present disclosure.

DETAILED DESCRIPTION

Figure 1A:
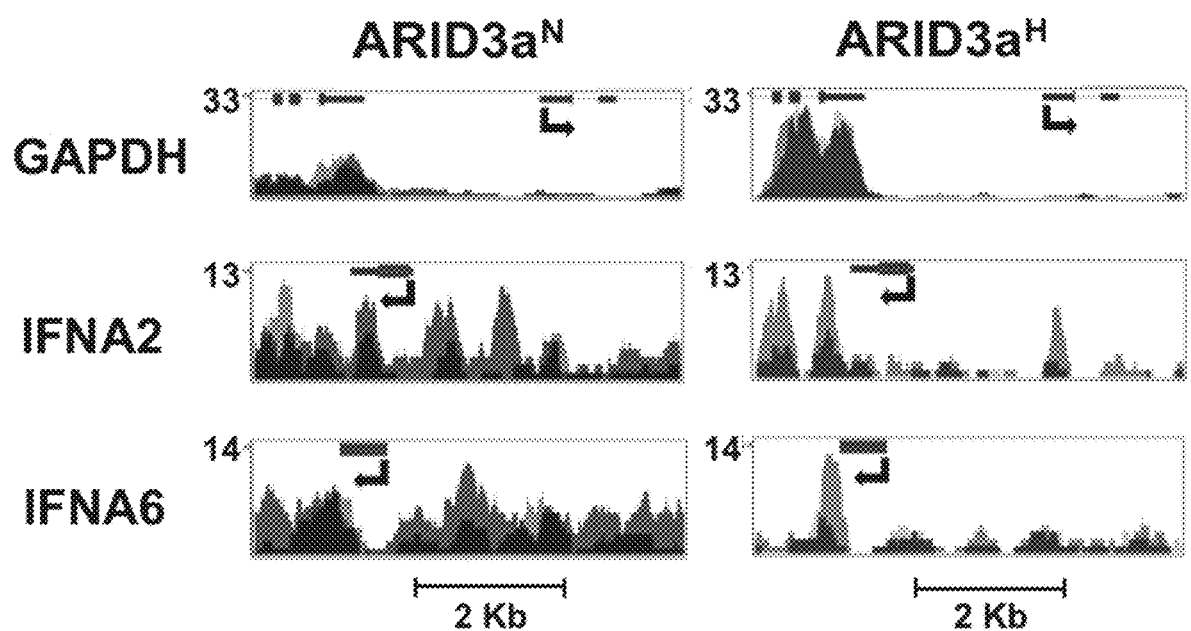
FIG. 1A shows methylation patterns of two IFN-alpha genes from PBMCs of two ARID3a$^N$ (lightest grey and medium grey on left figures) and two ARID3a$^H$ (medium grey and light grey on right figures) SLE patients. The darkest regions are positions methylated in both samples. Gene positions and transcription direction are indicated with arrows. The housekeeping gene, GAPDH, promoter served as a hypomethylated control.

Enhanced disease activity in patients with systemic lupus erythematosus (SLE) appears to be associated with dramatic increase in numbers of B lymphocytes expressing the transcription factor AT-rich-interactive domain 3a (ARID3a). Further, over-expression of ARID3a appears to result in increased production of IFN-alpha. Compounds able to interfere with IFN-alpha production would be useful as therapeutics for treating SLE patients. Antisense oligonucleotide compounds are oligomeric compounds that are capable of undergoing hybridization to a target nucleic acid, such as pre-mRNA or mature mRNA molecules. Antisense technology is emerging as an effective means for reducing the expression of such gene products and the proteins encoded by them. By virtue of their complementarity to certain target regions of ARID3a pre-mRNA or ARID3a mRNA, the antisense oligonucleotides (ASOs) of the present disclosure can block or inhibit translation of the ARID3a pre-mRNA or mRNA, and/or modify the processing of ARID3a pre-mRNA or mRNA to produce a splice variant of the mRNA, and/or block or inhibit excision of introns from an ARID3a pre-mMRNA into a mature mRNA.

Therefore, in at least certain exemplary (but non-limiting) embodiments, the present disclosure is directed to antisense oligonucleotides (including but not limited to morpholino oligomers) that are specific to inhibiting, directly or indirectly, the translation of ARID3a in B lymphocytes. There is a strong association between ARID3a expression and transcription of genes associated with lupus interferon signatures. Human effector B lymphocytes express ARID3a and secrete interferon alpha (IFN-alpha). Further, interferon alpha production from these ARID3a+ healthy B lymphocytes stimulates an increase in IFN-alpha production in plasmacytoid dendritic cells. ARID3a expression is also associated with IFN-alpha production in other peripheral blood cells including neutrophils and other types of dendritic cells. Therefore, because IFN-alpha production causes inflammatory responses, certain embodiments of the present disclosure are directed to treatments for inhibiting IFN-alpha production by inhibiting ARID3a using antisense compounds, such as (but not limited to) the antisense compounds disclosed herein, including morpholino antisense compounds. The ASOs disclosed herein can be used to treat SLE as well as other diseases or conditions associated with increased IFN-alpha production (interferonopathies), including but not limited to lupus erythematosus, rheumatoid arthritis, and Sjogren's syndrome, Down's syndrome, and virally induced conditions with inflammation due to increased levels of IFN-alpha including herpes viruses, Epstein Barr virus, mononucleosis, and varicella zoster.

In at least certain exemplary (but non-limiting) embodiments, the ASOs of the present disclosure have approximately, for example, 15 to 50, or 18 to 40, or 20 to 30 nucleotides and include a targeting sequence that is complementary to a target sequence of a nucleic acid which comprises a portion of (1) a pre-mRNA transcribed from an ARID3a gene sequence, and/or (2) a mature mRNA processed from said pre-mRNA. When the ASO binds to the target region of a preprocessed mRNA, it effectively inhibits splicing at the normal splice acceptor site and thus produces a splice variant mRNA, leading to truncated or otherwise aberrant versions of the ARID3a protein upon translation. When the ASO binds to the target region of a mature mRNA, it effectively inhibits proper translation of the mRNA into an ARID3a protein. Where used herein, the term antisense oligonucleotide (ASO) may also refer to an antisense compound which includes a moiety linked to the antisense oligonucleotide, such as (but not limited to) a cell penetration enhancing moiety, such as (but not limited to) a cell penetrating peptide or ligand.

Before further describing various embodiments of the compounds and methods for treating inflammatory diseases and conditions (such as, but not limited to SLE) by way of exemplary description, examples, and results, it is to be understood that the inhibitors of the present disclosure are not limited in application to the details of specific embodiments and examples as set forth in the following description.

The description provided herein is intended for purposes of illustration only and is not intended to be construed in a limiting sense. As such, the language used herein is intended to be given the broadest scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, a number of specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compounds, compositions, and methods and application and use thereof disclosed herein can be made and executed without undue experimentation in light of the present disclosure. Thus, while the compositions and methods have been described in terms of particular embodiments, it will be apparent to those of skill in the art that variations may be applied to the compositions and methods in the steps or in the sequence of steps of the methods described herein without departing from the concept, spirit, and scope of the inventive concepts.

All patents, published applications, and non-patent publications mentioned in the specification or referenced in any portion of this application, are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular. Where used herein, the specific term "single" is limited to only "one."

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," or "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, Z alone, as well as any combination of two of X, Y, and Z and all three of X, Y, and Z.

As used herein, all numerical values or ranges include fractions of the values and integers within such ranges and fractions of the integers within such ranges unless the context clearly indicates otherwise. Thus, to illustrate, reference to a numerical range such as 1-10 includes 1, 2, 3, 4, 5, 6, 7, 8, 9, 10, as well as 1.1, 1.2, 1.3, 1.4, 1.5, etc. and so forth. Reference to a range of 1-50 therefore includes 1, 2, 3, 4, 5, 6, 7, 8, 9, 10, 11, 12, 13, 14, 15, 16, 17, 18, 19, 10, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. Reference to an integer with more (greater) or less than includes any number greater or less than the reference number, respectively. Thus, for example, reference to less than 100 includes 99, 98, 97, etc. all the way down to the number one (1); and less than 10 includes 9, 8, 7, etc. all the way down to the number one (1).

As used in this specification and claims, the words "comprising" (and any form of comprising, such as "comprise" or "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or methods steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, BC, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the inherent variation of error for the method used to administer the composition, or the variation that exists among the study subjects. As used herein, the qualifiers "about" and "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately," where used herein when referring to a measurable value such as an amount, a temporal duration, and the like is meant to encompass, for example, variations of ±20%, or ±10%, or +5%, or +1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, any reference to "one embodiment" or "an embodiment" means that a particular element, feature, structure, or characteristic described in connection with the embodiment is included in at least one embodiment and may be included in other embodiments. The appearances of the phrases "one embodiment" and "an embodiment" in various places in the specification are not necessarily all referring to the same embodiment and are not necessarily limited to a single or particular embodiment. Further, all references to "embodiments" herein are solely for purposes of illustration only and are not intended to be limiting of the present disclosure unless explicitly indicated otherwise.

The term "pharmaceutically acceptable" refers to compounds and compositions which are suitable for administration to humans and/or animals without undue adverse side effects such as toxicity, irritation, and/or allergic response commensurate with a reasonable benefit/risk ratio. The compounds and compositions of the present disclosure may be combined with one or more pharmaceutically-acceptable excipients, including carriers, vehicles, and diluents, which may improve solubility, deliverability, dispersion, stability, and/or conformational integrity of the compounds and compositions.

As used herein, "pure" or "substantially pure" means an object species is the predominant species present (i.e., on a molar basis, it is more abundant than any other object species in the composition thereof), and particularly a substantially purified fraction is a composition wherein the object species comprises at least 50 percent (on a molar basis) of all macromolecular species present. Generally, a substantially pure composition will comprise more than about 80% of all macromolecular species present in the composition, and more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

Non-limiting examples of animals within the scope and meaning of this term include dogs, cats, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures or reducing the onset of a condition or disease. The term "treating" refers to administering the composition to a subject for therapeutic purposes and/or for prevention.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable therapeutic or treatment effect in a subject without excessive adverse side effects (such as substantial toxicity, irritation, and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein. An effective amount also refers to an amount of an antisense compound of the present disclosure which is effective in reducing expression of ARID3a and/or production of interferon-alpha.

The term "ameliorate" means a detectable or measurable improvement in a subject's condition, disease, or symptom thereof. A detectable or measurable improvement includes a subjective or objective decrease, reduction, inhibition, suppression, limit, or control in the occurrence, frequency, severity, progression, or duration of the condition or disease, or an improvement in a symptom or an underlying cause or a consequence of the disease, or a reversal of the disease. A successful treatment outcome can lead to a "therapeutic effect" or "benefit" of ameliorating, decreasing, reducing, inhibiting, suppressing, limiting, controlling, or preventing the occurrence, frequency, severity, progression, or duration of a disease or condition, or consequences of the disease or condition in a subject.

A decrease or reduction in worsening, such as stabilizing the condition or disease, is also a successful treatment outcome. A therapeutic benefit therefore need not be complete ablation or reversal of the disease or condition, or any one, most or all adverse symptoms, complications, consequences, or underlying causes associated with the disease or condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition or disease (e.g., stabilizing), over a short or long duration of time (hours, days, weeks, months, etc.). Effectiveness of a method or use, such as a treatment that provides a potential therapeutic benefit or improvement of a condition or disease, can be ascertained by various methods and testing assays.

Where used herein, the term ARID3a$^H$ refers to a population of SLE patients or cells from SLE patients that has high numbers of ARID3a$^+$ B cells in total numbers of B cells (i.e., greater than 2 standard deviations above the mean found in healthy individuals), including any mixture of the defined B cell subpopulations. Where used herein, the term ARID3a$^N$ refers to a population of SLE patients that has numbers of ARID3a$^+$ B cells similar to healthy individuals who do not have SLE, and includes up to 2 standard deviations above the mean found in such healthy individuals.

Specific amino acids may be referred to herein by the following designations: alanine: ala or A; arginine: arg or R; asparagine: asn or N; aspartic acid: asp or D; cysteine: cys or C; glutamic acid: glu or E; glutamine: gln or Q; glycine: gly or G; histidine: his or H; isoleucine: ile or I; leucine: leu or L; lysine: lys or K; methionine: met or M; phenylalanine: phe or F; proline: pro or P; serine: ser or S; threonine: thr or T; tryptophan: trp or W; tyrosine: tyr or Y; and valine: val or V.

For purposes of classifying amino acids substitutions as conservative or nonconservative, amino acids are grouped in one embodiment as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same group. Nonconservative substitutions constitute exchanging a member of one of these groups for a member of another.

Tables of conservative amino acid substitutions have been constructed and are known in the art. In other embodiments, examples of interchangeable amino acids include, but are not limited to, the following: arginine and lysine; glutamate and aspartate; serine and threonine; glutamine and asparagine; and valine, leucine, and isoleucine. In other embodiments, the following substitutions can be made: Ala (A) by leu, ile, or val; Arg (R) by gln, asn, or lys; Asn (N) by his, asp, lys, arg, or gln; Asp (D) by asn or glu; Cys (C) by ala or ser; Gln (Q) by glu or asn; Glu (E) by gln or asp; Gly (G) by ala; His (H) by asn, gln, lys, or arg; Ile (I) by val, met, ala, phe, or leu; Leu (L) by val, met, ala, phe, or ile; Lys (K) by gln, asn, or arg; Met (M) by phe, ile, or leu; Phe (F) by leu, val, ile, ala, or tyr; Pro (P) by ala; Ser (S) by thr; Thr (T) by ser; Trp (W) by phe or tyr; Tyr (Y) by trp, phe, thr, or ser; and Val (V) by ile, leu, met, phe, or ala.

Other considerations for amino acid substitutions include whether or not the residue is located in the interior of a protein or is solvent- (i.e., externally) exposed. For interior residues, conservative substitutions include for example: Asp and Asn; Ser and Thr; Ser and Ala; Thr and Ala; Ala and Gly; Ile and Val; Val and Leu; Leu and Ile; Leu and Met; Phe and Tyr; and Tyr and Trp. For solvent-exposed residues, conservative substitutions include for example: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; and Phe and Tyr.

In certain embodiments disclosed herein, nucleic acids derived from or encoding portions of ARID3a are provided. In certain aspects, the nucleic acids may comprise wild-type or a mutant version of these genes. In particular aspects, the nucleic acid comprises a precursor mRNA (a.k.a., pre-mRNA) or mature mRNA (a.k.a., mRNA), or portions thereof. In particular aspects, the nucleic acid encodes a protein, polypeptide, or peptide.

The term "nucleic acid" is well known in the art. A "nucleic acid" as used herein will generally refer to a molecule (i.e., a strand) of DNA, RNA, or a derivative or analog thereof, comprising a nucleobase. A nucleobase includes, for example, a naturally-occurring purine or pyrimidine base found in DNA (e.g., an adenine "A," a guanine "G," a thymine "T," or a cytosine "C") or RNA (e.g., an "A," a "G," a "C," or a uracil "U"). The term "nucleobase" also includes non-natural bases as described below. The term "nucleic acid" encompasses the terms "oligonucleotide" and "polynucleotide," each as a subgenus of the term "nucleic acid." The term "oligonucleotide" generally refers to a molecule of between about 3 and about 100 nucleobases in length. The term "polynucleotide" generally refers to at least one molecule of greater than about 100 nucleobases in length. These definitions generally refer to a single-stranded molecule, but in specific embodiments will also encompass an additional strand that is partially, substantially, or fully complementary to the single-stranded molecule. Thus, a nucleic acid may encompass a double-stranded molecule that comprises a complementary strand or "complement" of a particular sequence comprising a molecule. As used herein, a single-stranded nucleic acid may be denoted by the prefix "ss," and a double-stranded nucleic acid by the prefix "ds." The terms "polynucleotide sequence" and "nucleic acid," as used herein, include any polynucleotide sequence which encodes a peptide or fusion protein (or polypeptide) including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3', or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure; however, open linear structures are generally preferred (but not limiting). Within the oligonucleotide structure, the phosphate groups are commonly referred to as forming the internucleoside backbone of the oligonucleotide. The normal linkage or backbone of RNA and DNA is a 3' to 5' phosphodiester linkage.

Therefore, in the context of the present disclosure, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars, and covalent internucleoside (backbone) linkages, as well as oligonucleotides having non-naturally-occurring nucleobases, sugars, and synthetic heterocycles and covalent internucleoside (backbone) linkages which function similarly. Such modified or substituted non-natural oligonucleotides, as compared to native (natural) forms may have desirable properties such as, for example (but not by way of limitation), enhanced cellular uptake, enhanced affinity for nucleic acid target, and increased stability in the presence of nucleases.

Where used herein in reference to an antisense compound, the term "oligonucleotide" is also intended to include linked nucleobase sequences containing modified backbones comprising non-natural internucleoside linkages. As defined in this specification, oligonucleotides having modified backbones include those that retain a phosphorus atom in the backbone and those that do not have a phosphorus atom in the backbone. Further, for the purposes of this specification, the term "nucleoside" is intended to refer to a nucleobase linked to a ribose or deoxyribose sugar (a natural nucleoside), and to a nucleobase linked to a non-ribose or non-deoxyribose heterocycle, e.g., a morpholine structure (a non-natural, or modified, nucleoside or other structure described elsewhere herein). Thus, a series of such modified, non-natural, nucleosides linked together via an internucleoside backbone can also be considered to be an oligonucleotide (a non-natural, or modified, oligonucleotide). Further, the term "sugar" where used herein in the context of a nucleoside, is intended to include "non-sugar" heterocyclic compounds, such as (but not limited to) morpholines, as the portion of the internucleoside backbone which is linked to the nucleobase.

Oligonucleotides useful in the compounds and methods disclosed herein also include those comprised entirely or partially of naturally occurring nucleobases. Naturally occurring nucleobases include adenine, guanine, thymine, cytosine, uracil, and 5-methylcytosine (5-me-C).

As noted above, oligonucleotides of the present disclosure may further include those comprised entirely or partially of modified nucleobases and nucleosides (semi-synthetically or synthetically derived, natural or non-natural), including but not limited to pseudouridine, dihydrouridine, inosine, ribothymidine, 7-methylguanosine, hypoxanthine, xanthine, 5-hydroxymethyl cytosine, 2-aminoadenine, 2-methyladenine, 6-methyladenine, 2-propyladenine, N6-adenine, N6-isopentenyladenine, 2-methylthio-N6-isopentenyladenine, 2-methylguanine, 6-methylguanine, 2-propylguanine, 1-methylguanine, 7-methylguanine, 2,2-dimethylguanine, 2-thiouracil, 2-thiothymine and 2-thiocytosine, 5-fluorouracil, 5-bromouracil, 5-chlorouracil, 5-iodouracil, dihydrouracil, 5-methyl-2-thiouracil, 2-thiouracil, 4-thiouracil, 5-methyluracil, uracil-5-oxyacetic acid methylester, uracil-5-oxyacetic acid, 5-carboxymethylaminomethyl-2-thiouridine, hypoxanthine, xantine, 4-acetylcytosine, 5-(carboxyhydroxylmethyl) uracil, 5-methoxycarboxymethyluracil, 5-methoxyuracil, 5-methyl-2-thiouracil, 3-(3-amino-3-N-2-carboxypropyl) uracil, 5-carboxymethylaminomethyluracil, 5-methylaminomethyluracil, 5-methoxyaminomethyl-2-thiouracil, 5-propynyl uracil and cytosine and other alkynyl derivatives of pyrimidine bases, 6-azo uracil, cytosine, and thymine, 5-uracil (pseudouracil), 4-thiouracil, 8-halo-adenine, 8-amino adenine, 8-thiol adenine, 8-thioalkyl adenine, 8-hydroxyl adenine, 5-halo particularly 5-bromo uracil, 5-trifluoromethyl uracil, 3-methylcytosine, 5-methylcytosine, 5-trifluoromethyl cytosine, 7-methylguanine and 7-methyladenine, 2-F-adenine, 2-amino-adenine, 8-azaguanine and 8-azaadenine, 7-deazaguanine, 8-halo-guanine, 8-amino guanine, 8-thiol guanine, 8-thioalkyl guanine, 8-hydroxyl guanine, 7-deazaadenine, 3-deazaguanine, 3-deazaadenine, beta-D-galactosylqueosine, beta-D-mannosylqueosine, 1-methylinosine, 2,6-diaminopurine and queosine. Further modified nucleobases include tricyclic pyrimidines such as (but not limited to) phenoxazine cytidine(1H-pyrimido[5,4-b][1,4]benzoxazin-2(3H)-one), and phenothiazine cytidine (1H-pyrimido[5,4-b][1,4]benzothiazin-2(3H)-one.

The present disclosure also encompasses oligonucleotides which comprise targeting sequences (base sequences) that are complementary to particular nucleic acid target sequences taught herein. A nucleic acid is a "complement" or is "complementary" to another nucleic acid when it is capable of base-pairing with the other nucleic acid according to the standard Watson-Crick, Hoogsteen, or reverse Hoogsteen binding complementarity rules. Polynucleotides (nucleic acids) are described as "complementary" to one another when hybridization occurs in an antiparallel configuration between two single-stranded polynucleotides.

More particularly, "complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target, and as such, as is understood in the art, the targeting sequence of an antisense oligonucleotide of the present disclosure need not be 100% complementary to that of its target sequence to be specifically hybridizable. An antisense compound is specifically hybridizable when binding of the compound to the target sequence of the DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed. An antisense oligonucleotide and a target sequence are thus complementary to each other when a sufficient number of nucleobases of the antisense oligonucleotide can hydrogen bond with the corresponding nucleobases of the target sequence, such that a desired effect will occur (e.g., antisense inhibition of a target nucleic acid, such as (but not limited to) an ARID3a nucleic acid).

For example, an antisense oligonucleotide in which 18 of 20 nucleobases of the antisense oligonucleotide are complementary to a target sequence, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense oligonucleotide which is 18 nucleobases in length having three noncomplementary nucleobases which are flanked by two regions of complete complementarity with the target nucleic acid, or are distributed in non-contiguous positions, would have 83% overall complementarity with the target sequence.

In other embodiments, the antisense oligonucleotides provided herein are fully complementary (i.e. 100% complementary) to a target sequence of a nucleic acid. For example, the antisense compound may be fully complementary to an entire ARID3a nucleic acid segment disclosed herein (SEQ ID NOS:1-28), or to only a portion of an ARID3a nucleic acid segment disclosed herein. As used herein, "fully complementary" means each nucleobase of an antisense oligonucleotide is capable of precise base pairing with the corresponding nucleobases of a target nucleic acid.

The term target sequence where used herein refers to a contiguous series of nucleobases in a nucleotide sequence (target region). Where used herein the term "target region" refers to one of SEQ ID NOS:1-28. The term "target sequence" refers to a sequence that is a subsequence (portion or segment) of the target region, or to the entire sequence of the target region. For example, a target sequence of SEQ ID NO:1 (which comprises 32 nucleobases), may consist of 18, 19, 20, 21, 22, 23, 24, 25, 26, 27, 28, 29, 30, 31, or 32 nucleobases. A target sequence may include the 5' terminal nucleobase of a nucleic acid sequence plus adjacent internal nucleobases of the sequence, or the 3' terminal nucleobase plus adjacent internal nucleobases of the sequence, or only internal nucleobases within the sequence, or the target sequence may be 100% identical to the target region. In certain embodiments, an antisense compound of the present disclosure comprises an oligonucleotide having a nucleobase sequence that, when written in the 5' to 3' direction, comprises the reverse complement of a target sequence of a nucleic acid target region (e.g., one of SEQ ID NOS: 1-28) to which it is targeted.

In at least certain embodiments, the present disclosure is directed to oligonucleotides that are antisense oligonucleotides ("ASO"). As used herein, the terms "antisense oligonucleotide" and "ASO" refer to an oligomeric nucleic acid that is capable of hybridizing with its complementary target sequence, generally resulting in the modulation of the normal function of the nucleic acid (e.g., mRNA) having the target sequence. "Antisense" further refers to an oligomer having a sequence of nucleotide bases and a subunit-to-subunit backbone that allows the antisense oligomer to hybridize to a target sequence in an RNA by Watson-Crick base pairing, to form an RNA:oligomer heteroduplex within the target sequence, typically with an mRNA. The antisense oligomer (oligonucleotide) may have exact sequence complementarity to the target sequence or near complementarity, and may include modified (non-natural) nucleobases in place of naturally complementary nucleobases.

The terms "complementary" and "antisense" can be used interchangeably. Complementary also refers to polynucleotide sequences that are substantially complementary (antisense) over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches.

In certain embodiments, antisense oligonucleotides of the present disclosure are synthesized using one or more modified nucleotides. As used herein, the terms "modified" and "modification" when used in the context of the constituents of a nucleotide monomer, i.e., sugar, nucleobase, and internucleoside linkage (backbone), refer to non-natural changes to the chemical structure of these naturally occurring constituents or the substitutions of these constituents with non-naturally occurring ones, i.e., mimetics. For example, the "unmodified" or "naturally occurring" sugar ribose (RNA) can be modified by replacing the hydrogen at the 2'-position of ribose with a methyl group. Similarly, the naturally occurring internucleoside linkage of nucleic acids is a 3' to 5' phosphodiester linkage that can be modified by replacing one of the non-bridging phosphate oxygen atoms with a sulfur atom to create a phosphorothioate linkage. Modified oligonucleotides are structurally distinguishable but functionally interchangeable with naturally occurring or synthetic unmodified oligonucleotides and usually have enhanced properties such as increased resistance to degradation by exonucleases and endonucleases or increased binding affinity.

As noted above, in certain embodiments, modifications to the antisense oligonucleotides encompass substitutions or changes to internucleoside linkages, sugar moieties, or nucleobases. Where used herein the term "non-natural," when used in reference to an antisense oligonucleotide, refers to an antisense oligonucleotide which comprises at least one modification selected from the group consisting of a modified internucleoside linkage, a modified sugar, and a modified nucleobase, wherein such modified internucleoside linkage, modified sugar, and/or modified nucleobase is not found naturally in DNA or RNA.

Non-naturally occurring internucleoside linkages "oligonucleotide backbones" include those that retain a phosphorus atom and also those that do not have a phosphorus atom. Numerous phosphorous containing modified oligonucleotide backbones are known in the art and include, for example (but not by way of limitation), phosphoramidites, phosphorodiamidate morpholinos, phosphorothioates, phosphorodithioates, phosphotriesters, aminoalkylphosphotri-esters, methyl phosphonates and other alkyl phosphonates including 3'-alkylene phosphonates, 5'-alkylene phosphonates and chiral phosphonates, and phosphinates. In some embodiments, the modified oligonucleotide backbones are without phosphorus atoms and comprise short chain alkyl or cycloalkyl internucleoside linkages, mixed heteroatom and alkyl or cycloalkyl internucleoside linkages, or one or more short chain heteroatomic or heterocyclic internucleoside linkages. In further embodiments, the non-naturally occurring internucleoside linkages are uncharged and in others, the linkages are achiral. In some embodiments, the non-naturally occurring internucleoside linkages are uncharged and achiral, such as (but not limited to) the peptide linkages of peptide nucleic acids (PNAs). In at least certain embodiments, the antisense oligomers of the present disclosure are morpholino oligomers as discussed elsewhere herein. In certain embodiments, an ASO of the present disclosure with a morpholino backbone typically contains a stretch of between 20-30 nucleotides.

It is understood that the sequence set forth in each SEQ ID NO contained herein is independent of any modification to a sugar moiety, an internucleoside linkage, or a nucleobase. As such, antisense compounds defined by a complementary correspondence to a SEQ ID NO disclosed herein, or segment thereof, may comprise, independently, one or more modifications to a sugar moiety, an internucleoside linkage, or a nucleobase.

Examples of non-natural (modified) oligonucleotide backbones include, but are not limited to, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thiono-phosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5', or 2' to 2' linkage. Certain oligonucleotides having inverted polarity comprise a single 3' to 3' linkage at the 3'-most internucleotide linkage, i.e., a single inverted nucleoside residue which may be abasic (the nucleobase is missing or has a hydroxyl group in place thereof). Various salts, mixed salts, and free acid forms are also included. Examples of U.S. patents that teach the preparation of such phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697; and 5,625,050, each of which is herein incorporated by reference in its entirety.

Examples of modified oligonucleotide backbones that do not include a phosphorus atom therein include those having backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts. Examples of U.S. patents that teach the preparation of such non-phosphorus containing oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference in its entirety.

In certain oligonucleotide mimetics of the present disclosure, both the sugar and the internucleoside linkage, i.e., the backbone, of the nucleotide units are replaced with novel (non-natural) groups. One such oligomeric compound is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Examples of U.S. patents that teach the preparation of PNA compounds include, but are not limited to, U.S. Pat. Nos. 5,539,082; 5,714,331; and 5,719,262, each of which is herein incorporated by reference in its entirety.

In one embodiment, antisense compounds targeted to an ARID3a nucleic acid comprise one or more modified internucleoside linkages. In some embodiments, the modified internucleoside linkages are phosphorothioate linkages. In other embodiments, each internucleoside linkage of an antisense compound is a phosphorodiamidate internucleoside linkage, and more particularly a phosphorodiamidate morpholino internucleoside linkage.

As used herein, the terms "complementary" or "complement" also refer to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

The term "homologous" or "% identity" as used herein means a nucleic acid (or fragment thereof), including morpholino nucleic acids, or a protein (or a fragment thereof) having a degree of homology to the corresponding natural reference nucleic acid or protein that may be in excess of 70%, or in excess of 80%, or in excess of 85%, or in excess of 90%, or in excess of 91%, or in excess of 92%, or in excess of 93%, or in excess of 94%, or in excess of 95%, or in excess of 96%, or in excess of 97%, or in excess of 98%, or in excess of 99%. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage of homology as described above is calculated as the percentage of the components found in the smaller of the two sequences that may also be found in the larger of the two sequences (with the introduction of gaps), with a component being defined as a sequence of four contiguous amino acids. Also included as substantially homologous is any protein product which may be isolated by virtue of cross reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993, 90, 5873-5877.

Percentage sequence identities can be determined with protein sequences maximally aligned by the Kabat numbering convention. After alignment, if a particular polypeptide region is being compared with the same region of a reference polypepetide, the percentage sequence identity between the subject and reference polypeptide region is the number of positions occupied by the same amino acid in both the subject and reference polypeptide region divided by the total number of aligned positions of the two regions, with gaps not counted, multiplied by 100 to convert to percentage.

In one embodiment "% identity" represents the number of amino acids or nucleotides which are identical at corresponding positions in two sequences of a protein having the same activity or encoding similar proteins. For example, two amino acid sequences each having 100 residues will have 95% identity when 95 of the amino acids at corresponding positions are the same.

Another example of a mathematical algorithm used for comparison of sequences is the algorithm of Myers & Miller, CABIOS 1988, 4, 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988, 85, 2444-2448.

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish, 1996, Local alignment statistics, Doolittle ed., Methods in Enzymology 266, 460-480; Altschul et al., Journal of Molecular Biology 1990, 215, 403-410; Gish & States, Nature Genetics, 1993, 3: 266-272; Karlin & Altschul, 1993, Proc. Natl. Acad. Sci. USA 90, 5873-5877; all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information. These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as (but not limited to) PAM can be utilized.

As used herein, "hybridization," "hybridize(s)," or "capable of hybridizing" is understood to mean the forming of a double or triple stranded molecule or a molecule with partial double or triple stranded nature. The term "anneal" as used herein is synonymous with "hybridize." The term "hybridization," "hybridize(s)," or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Non-limiting applications include isolating a nucleic acid, such as (but not limited to) a gene or a nucleic acid segment thereof, or detecting at least one specific mRNA transcript or a nucleic acid segment thereof, and the like. Stringent conditions may comprise low salt and/or high temperature conditions, such as (but not limited to) provided by about 0.02 M to about 0.15 M NaCl at temperatures of about 50° C. to about 70° C. It is understood that the temperature and ionic strength of a desired stringency are determined in part by the length of the particular nucleic acid, the length and nucleobase content of the target sequence, the charge composition of the nucleic acid, and to the presence or concentration of formamide, tetramethylammonium chloride, or other solvent in a hybridization mixture.

It is also understood that these ranges, compositions, and conditions for hybridization are mentioned by way of non-limiting examples only, and that the desired stringency for a particular hybridization reaction is often determined empirically by comparison to one or more positive or negative controls. Depending on the application envisioned, varying conditions of hybridization to achieve varying degrees of selectivity of a nucleic acid towards a target sequence are used. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suit a particular application.

In at least certain embodiments, an ASO of the present disclosure that is complementary to a target RNA is capable of hybridizing to the target RNA under stringent conditions. Typically, this means that the reverse complement of the ASO is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identical to the nucleotide sequence of the target site of the target nucleic acid. Such an ASO therefore generally has either two, one, or zero mismatches with the reverse complement of the target RNA. A mismatch is defined herein as a nucleotide or nucleotide analogue that does not have the same base pairing capacity in kind, not necessarily in amount, as the nucleotide it replaces. For instance, the complement of a base that binds with two hydrogen bonds is another base that binds with two hydrogen bonds (e.g., A and T or U). The complement of a base that binds with three hydrogen bonds is another base that binds with three hydrogen bonds (e.g., G and C).

As used herein "wild-type" refers to the naturally occurring sequence of a nucleic acid at a genetic locus in the genome of an organism, or a sequence transcribed or translated from such a nucleic acid. Thus, the term "wild-type" also may refer to an amino acid sequence encoded by a nucleic acid. As a genetic locus may have more than one sequence or allele in a population of individuals, the term "wild-type" encompasses all such naturally occurring allele(s). As used herein the term "polymorphic" means that variation exists (i.e., two or more alleles exist) at a genetic locus in the individuals of a population. As used herein "mutant" refers to a change in the sequence of a nucleic acid or its encoded protein, polypeptide, or peptide that is the result of the hand of man.

In certain embodiments, a "gene" refers to a nucleic acid that is transcribed. In certain aspects, the gene includes regulatory sequences involved in transcription, or message production or composition. In particular embodiments, the gene comprises transcribed sequences that encode for a protein, polypeptide or peptide. As will be understood by those in the art, this functional term "gene" includes both genomic sequences, RNA or cDNA sequences, or smaller engineered nucleic acid segments, including nucleic acid segments of a non-transcribed part of a gene, including (but not limited to) the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants, and/or the like.

The terms "morpholino nucleic acid," "morpholino oligomer," "morpholino oligonucleotide," "morpholino," or "phosphorodiamidate morpholino oligomer (PMO)" can be used interchangeably and as used herein, refer to a nucleic acid base structure comprising a chain of A, T, G, and/or C bases having a backbone of methylenemorpholine rings linked via phosphorodiamidate intersubunit linkages. The morpholino oligomers of the present disclosure also include variants thereof which comprise modified nucleobases which do not substantially diminish their affinity for the target epitope of the target nucleic acid molecules, such as (but not limited to) mRNA. For example, variants include, but are not limited to, morpholinos oligomers which are the same as the morpholinos described herein except having at least one base substitution (e.g., A for T, T for A, C for G, and G for C) which does not substantially impair the agonistic or antagonistic activity or properties of the variants described herein. Further, variant bases may comprise modified or non-natural purine and pyrimidine bases such as described hereinabove.

In at least certain embodiments, the morpholino oligomers of the present disclosure have approximately 15 to 50, or 18 to 40, or 20 to 30, or 22 to 28 nucleotides and include a targeting sequence that is complementary to a target sequence of a nucleic acid which comprises a portion of (1) a pre-mRNA transcribed from an ARID3a gene sequence, and/or (2) a mature mRNA processed from said pre-mRNA. When the morpholino oligomer binds to the target region of a preprocessed mRNA, it effectively inhibits splicing at the normal splice acceptor site and thus produces a splice variant mRNA, leading to truncated or otherwise aberrant versions of the ARID3a protein upon translation. When the morpholino oligomer binds to the target region of a mature mRNA, it effectively inhibits proper translation of the mRNA into an ARID3a protein. The morpholino oligomers disclosed herein may be constructed with morpholino subunits of the form shown in U.S. Pat. Nos. 5,698,685; 5,217,866; 5,142,047; 5,034,506; 5,166,315; 5,521,063; and 5,506,337, each of which is incorporated herein by reference in its entirety. The synthesis, structures, and binding characteristics of morpholino oligomers are detailed in these patents. In a morpholino oligomer, (i) the morpholino groups are linked together by uncharged phosphorus-containing linkages, one to three atoms long, joining the morpholino nitrogen of one subunit to the 5' exocyclic carbon of an adjacent subunit, and (ii) the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil, or thymine. Preparation of such oligomers is described in detail in U.S. Pat. No. 5,185,444, which is hereby incorporated by reference in its entirety. As shown in the reference, several types of nonionic linkages may be used to construct a morpholino backbone.

Such morpholino oligomers have shown high binding affinity for RNA targets, and the uncharged backbone favors uptake into cells and reduces non-specific binding interactions, relative to charged analogs such as phosphorothioates. They have been shown to provide significantly improved activity and selectivity in inhibiting translation of targeted sequences in comparison to phosphorothioate oligonucleotides. The morpholino oligomers have very high nuclease resistance and good water solubility, making them good candidates for in vivo use. In at least certain embodiments, the antisense oligomers disclosed herein do not activate RNase H.

In certain embodiments, the antisense oligomers of the present disclosure comprise a Peptide Nucleic Acid (PNA), having a modified polyamide backbone. The backbone of the PNA is composed of N-(2-aminoethyl)-glycine units linked by peptide bonds, wherein the nucleobases are linked to the backbone by methylene carbonyl bonds (see for example, U.S. Pat. Nos. 7,223,833 and 8,859,490, and PCT Published Patent Application Nos. WO 92/20702, WO 92/20703, and WO 93/12129 each of which is incorporated herein by reference in its entirety). An alternative backbone comprises a one-carbon extended pyrrolidine PNA monomer. Since the backbone of a PNA molecule contains no charged phosphate groups, PNA-RNA hybrids are usually more stable than RNA-RNA or RNA-DNA hybrids, respectively.

In certain embodiments, the antisense oligomers of the present disclosure comprise nucleotides comprising one or more sugar moieties that are mono- or disubstituted at the 2', 3', and/or 5' position, such as (but not limited to) a —OH; —F; substituted or unsubstituted, linear or branched lower (Cl—Cl0) alkyl, alkenyl, alkynyl, alkaryl, allyl, aryl, or aralkyl that may be interrupted by one or more heteroatoms; O-, S-, or N-alkyl; O-, S-, or N-alkenyl; O-, S-, or N-alkynyl; O-, S-, or N-allyl; O-alkyl-O alkyl; -methoxy; -aminopropoxy; -aminoxy; methoxyethoxy; -dimethylaminooxyethoxy; and -dimethylaminoethoxyethoxy. The sugar moiety can be a pyranose or derivative thereof, or a deoxypyranose or derivative thereof, a ribose or a derivative thereof, or a deoxyribose or a derivative thereof. Such derivatized sugar moieties comprise a Locked Nucleic Acid (LNA), in which the 2'-carbon atom is linked to the 3' or 4' carbon atom of the sugar ring, thereby forming a bicyclic sugar moiety. In one embodiment, an LNA comprises 2'-0,4'-C-ethylene-bridged nucleic acid. These substitutions render the nucleotide analogue RNase H- and nuclease-resistant and increase the affinity for the target RNA.

For the purposes of describing the non-natural internucleoside linkages present in PNAs and LNAs, the non-natural internucleoside linkage present in a PNA will be defined herein as a "peptide" linkage, while the non-natural internucleoside linkage present in an LNA will be defined herein as a "locked" linkage.

In some embodiments, the antisense oligonucleotides further comprise a heterogeneous molecule covalently or non-covalently attached to the oligomer, with or without the use of a linker, also known as a crosslinker. In some embodiments, the heterogeneous molecule is a delivery or internalization moiety that enhances or assists the absorption, distribution, and/or cellular uptake of the oligonucleotides. These moieties include, for example, polyethylene glycols, cholesterols, biotin, vitamins, phospholipids, cell-penetrating peptides (CPPs), ligands to cell membrane receptors, and antigen-binding domains, such as (but not limited to) provided by an antibody, a Fab fragment of an antibody, or a single chain antigen binding domain, such as (but not limited to) a cameloid single domain antigen-binding domain.

In general, CPPs are well-known in the art and can be 6 to 30 amino acid residues in length, and include but are not limited to antennapedia, HIV tat, transportan, penetratin, MPG, pVEC, Pep-1, MAP, and other positively charged amino acids, such as (but not limited to) oligoarginine, poly-arginine, oligolysine or polylysine, $R_6W_3$, $R_9F_2$, RXR, RX, RB, and RBR; where R is arginine (which may include D-arginine), B is beta-alanine, and each X is independently NH—$(CHR^1)_n$—C(O), where n is 4-6 and each $R^1$ is independently H or methyl, such that $R^1$ is at most two methyls. In some embodiments, each $R^1$ is hydrogen. In other embodiments, the cationic peptide can be any of 6, 7, 8, 9, 10, 11, 12, 13, 14, 15, 16, 17, 18, 19, 20, 21, 22, 23, 24, 25, 26, 27, 28, 29, or 30 amino acid residues in length. In another embodiment, the variable X is 6-aminohexanoic acid. Other CPPs which can be used include but are not limited to those shown in U.S. Pat. No. 8,575,126 and U. S. Patent Application Publication No. 2009/0099066, each of which is incorporated by reference herein in their entirety. Other non-limiting examples of CPPs for enhancing uptake into cells are shown in U.S. Pat. Nos. 7,579,318; 7,943,581; 8,242,081; and 8,575,305 (each of which is incorporated herein by reference in its entirety).

In certain embodiments, the CPP is covalently linked directly to the 5' end of the ASO. In other embodiments, the CPP is linked to the antisense oligonucleotide via a spacer moiety linked to the 5' end of the ASO. The spacer moiety may be incorporated into the peptide during CPP synthesis. For example, where a spacer contains a free amino group and a second functional group (e.g., a carboxyl group or an amino group) that enables binding to another molecular moiety, the spacer may be conjugated to a solid support used for peptide synthesis. Thereafter, the cationic peptide may be synthesized directly onto the spacer's free amino group by standard solid phase techniques. In another embodiment, the spacer moiety may be conjugated to the CPP after peptide synthesis. Such conjugation may be achieved by methods well established in the art. In one embodiment, the linker contains at least one functional group suitable for attachment to the target functional group of the synthesized CPP. For example, a spacer with a free amine group may be reacted with the CPP's C-terminal carboxyl group. Non-limiting examples of spacers which may be used are shown in U.S. Published Patent Application No. 2015/0238627 (the entire contents of which are incorporated herein by reference).

In other embodiments, the antisense oligomers of the present disclosure can be attached to dendrimers such as (but not limited to) octa-guanadinium dendrimers for enhancing cellular uptake (for example as shown in U.S. Pat. Nos. 5,142,047; 5,185,444; and 8,198,429, each of which is incorporated herein by reference in its entirety). Conjugates of morpholino oligomers and octa-guanadinium dendrimers are known as "vivo-morpholinos."

In certain embodiments, antisense oligonucleotides of the present disclosure comprise nucleobase targeting sequences which are complementary, or substantially complementary, to at least 15 to 50 contiguous bases of the nucleic acid base (target) sequences shown in Table 1, which are derived from human ARID3a gene and a nucleic acid structure encoding ARID3a protein.

TABLE 1

Target regions for ARID3a antisense oligonucleotide inhibitors (5' > 3')

| SEQ ID NO: | Base Sequence |
|---|---|
| 1 | ATGAAACTACAGGCCGTGATGGAGACGCTGTT |
| 2 | CAGTTTAAGCAGCTCTACGAACTCGACGG |

TABLE 1-continued

Target regions for ARID3a antisense oligonucleotide inhibitors (5' > 3')

| SEQ ID NO: | Base Sequence |
|---|---|
| 3 | CAGAAGCGAGGGACACCTGTGAA |
| 4 | CTAAGATCAAGAAAGAGGAGGACTCAGCCATCCC |
| 5 | CACCCTGCGGACCCAATACATGAAGTACC |
| 6 | CAGCAGCTGTGCAAGCAGCAGC |
| 7 | GCTGATGCAACGTGCACTCCAGCAGAACTTCCTG |
| 8 | AGCTACCCGTGTCCTCCCTGGGCCTGGCCGCAAGCACCAATGGCAGCTCCATC |
| 9 | ATTCGGATCAACAGCCAAGCCTC |
| 10 | ACCCTGTGGTGGCAGCCCAGGCAGCAGCTGTGCAAGCAGCAGCCGCCCAAGCAGCTGTGGCCGCACAGGCAGCTGCCCTGGAACAGCTG |
| 11 | AAGATGGCCCTGGTGGCCGATGAGCAGCAACGGCTGATGCAACGTGCACTCCAGCAGAACTTCCTGGCCATGG |
| 12 | CGGATCAACAGCCAAGCCTCCGAAAGCC |
| 13 | GGCATCATGTACACAGGAGTTCTGTTTGCTCAGCC |
| 14 | CTCCACATCTACCTCAAATAACTCGTTGCCTTAA |
| 15 | AGGACATGGCCTCCGACGAGGACATGTGAGTTGGG |
| 16 | GACTCCTGCCCTCTGCTCACCCCAGGAAGCCCAAATGGGAGGAGGAGGAG |
| 17 | GACTTACGAGGAGCAGTTTAAG CAGGTGAGTGGGCG |
| 18 | ACCCATCCCCTCTCCACCCTCACAGCTCTACGAACTCGACGGG |
| 19 | TTGTTCAGCTTCATGCAGAAGCGAGGTGAGCCCTCTGCCCC |
| 20 | ACCTCCCTCTCGCCCCTTCCCCCAGGGACACCTGTGAACCGCATCCCCAT |
| 21 | AGTGCAGCCTTCACCCTGCGGACCCAGTGAGTG CGGACGGTTGTGCCGAG |
| 22 | TCCTCTTCCCTCGTCCCACCCACAGATACATGAAGTACCTGTACCCCTAC |
| 23 | CCCTAAGATCAAGAAAGGTAAGGGCCTGTATGGG |
| 24 | GGGAGGAGGACTCAGCCATCCCCATCAC |
| 25 | ATGAGCATTCGGATCAACAGCCAAGGTACTGCCCTCGTGCCCAGACCCGC |
| 26 | AACTAATTTGTTCTTCTTCCCACAGCCTCCGAAAGCCGCCAGGACTCTGC |
| 27 | GAGATCAACGGCATCATGTACACAGGTAGGACCCCTGAG CCACGCCCTG |
| 28 | CATATGTCTTCTGTTCTTGCCTTAGGAGTTCTGTTTGCTCAGCCGC |

As noted, anti-ARID3a antisense oligomers (oligonucleotides) of the present disclosure include, but are not limited to, nucleotide sequences between 15 and 50 nucleotides in length, including 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, which are complementary to an entire base sequence, or a portion thereof, of the target regions shown in Table 1. In certain embodiments, the ASO comprises a targeting sequence that is complementary to part of an ARID3a precursor (preprocessed) mRNA, i.e., a sequence which contains both introns and exons. In certain embodiments, the length of the complementary portion of the oligonucleotide is at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, or at least 50 nucleotides. As noted previously, an ASO of the present disclosure may further comprise additional nucleotides that are not complementary to the target sequence of the target pre-mRNA. When the target sequence is a pre-mRNA and comprises at least a portion of an intron and at least a portion of an exon adjacent to the intron, the ASO may bind to and overlap a portion of the intron and a portion of the adjacent exon, for example the ASO may substantially bind to a portion of the exon and at least two nucleotides of the adjacent intron, or may substantially bind to a portion of the intron and at least two nucleotides of the adjacent exon.

In certain embodiments, the present disclosure is directed to an antisense compound which comprises an antisense oligonucleotide comprising a targeting sequence consisting of a 15-50 nucleobase sequence which is at least 84% complementary to a target sequence (portion) of a nucleotide sequence selected from the group consisting of SEQ ID NOS: 1-28. In at least certain embodiments, the nucleobases of the nucleobase sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide. As noted above, the term target sequence (portion) refers to a contiguous series of nucleobases in the nucleotide sequence comprising the target region.

In certain embodiments, the antisense compound comprises an antisense oligonucleotide comprising a targeting sequence consisting of an 18-32 nucleobase sequence which is at least 84% complementary to a target sequence (portion) of a nucleotide sequence consisting of SEQ ID NO: 1. More particularly, the targeting sequence may consist of 18, 19, 20, 21, 22, 23, 24, 25, 26, 27, 28, 29, 30, 31, or 32 nucleobases. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide. One non-limiting example of an ASO which comprises a targeting sequence complementary to a target sequence of SEQ ID NO: 1 is the vivo morpholino referred to elsewhere herein as "ATG" which comprises a nucleobase targeting sequence 5'-TCTCCATCACGGCCTGTAGTTTCAT-3' (SEQ ID NO:29) that is complementary to positions 1-25 of SEQ ID NO: 1. Other examples of 25-mer ASOs embodied in the present disclosure include targeting sequences which are complementary to positions 2-26, 3-27, 4-28, 5-29, 6-30, 7-31, and 8-32. A person having ordinary skill in the art will readily see that other ASOs comprising target sequences having 18-32 bases can be created by selecting an initial base position in SEQ ID NO: 1 and extending the sequence for the desired number of positions to a terminal complementary position. Other targeting sequence sizes could be selected using the shift method shown below for determining possible target sequences of SEQ ID NO: 1. For example, if a 20-mer ASO is desired, a contiguous complementary target sequence of SEQ ID NO:1 could be selected from the set of base positions 1-20, 2-21, 3-22, 4-23, 5-24, 6-25, 7-26, 8-27, 9-28, 10-29, 11-30, 12-31, and 13-32 of SEQ ID NO: 1. Alternatively, if a 21-mer ASO is desired, a contiguous complementary target sequence of SEQ ID NO:1 could be selected from the set of base positions 1-21, 2-22, 3-23, 4-24, 5-25, 6-26, 7-27, 8-28, 9-29, 10-30, 11-31, and 12-32 of SEQ ID NO:1. Alternatively, if a 22-mer ASO is desired, a contiguous complementary target sequence of SEQ ID NO:1 could be selected from the set of base positions 1-22, 2-23, 3-24, 4-25, 5-26, 6-27, 7-28, 8-29, 9-30, 10-31, and 11-32 of SEQ ID NO: 1. Alternatively, if a 23-mer ASO is desired, a contiguous complementary target sequence of SEQ ID NO:1 could be selected from the set of base positions 1-23, 2-24, 3-25, 4-26, 5-27, 6-28, 7-29, 8-30, 9-31, and 10-32 of SEQ ID NO:1. Alternatively, if a 24-mer ASO is desired, a contiguous complementary target sequence of SEQ ID NO:1 could be selected from the set of base positions 1-24, 2-25, 3-26, 4-27, 5-28, 6-29, 7-30, 8-31, and 9-32 of SEQ ID NO:1. Alternatively, if a 26-mer ASO is desired, a contiguous complementary target sequence of SEQ ID NO:1 could be selected from the set of base positions 1-26, 2-27, 3-28, 4-29, 5-30, 6-31, and 7-32 of SEQ ID NO: 1. Alternatively, if a 27-mer ASO is desired, a contiguous complementary target sequence of SEQ ID NO:1 could be selected from the set of base positions 1-27, 2-28, 3-29, 4-30, 5-31, and 6-32 of SEQ ID NO:1. Alternatively, if a 28-mer ASO is desired, a contiguous complementary target sequence of SEQ ID NO: 1 could be selected from the set of base positions 1-28, 2-29, 3-30, 4-31, and 5-32 of SEQ ID NO:1. Alternatively, if a 29-mer ASO is desired, a contiguous complementary target sequence of SEQ ID NO: 1 could be selected from the set of base positions 1-29, 2-30, 3-31, and 4-32 of SEQ ID NO:1. Alternatively, if a 30-mer ASO is desired, a contiguous complementary target sequence of SEQ ID NO:1 could be selected from the set of base positions 1-30, 2-31, and 3-32 of SEQ ID NO: 1. Alternatively, if a 31-mer ASO is desired, a contiguous complementary target sequence of SEQ ID NO: 1 could be selected from the set of base positions 1-31 and 2-32 of SEQ ID NO: 1. Alternatively, if a 32-mer ASO is desired, a contiguous complementary target sequence of SEQ ID NO: 1 would be the set of base positions 1-32 of SEQ ID NO: 1.

In certain embodiments, the antisense compound comprises an antisense oligonucleotide comprising a targeting sequence consisting of an 18-29 nucleobase sequence which is at least 84% complementary to a target sequence of a nucleotide sequence consisting of SEQ ID NO:2. More particularly, the targeting sequence may consist of 18, 19, 20, 21, 22, 23, 24, 25, 26, 27, 28, or 29 nucleobases. A 25-mer ASO, for example, could comprise a targeting sequence which is complementary to a target sequence selected from the set of positions 1-25, 2-26, 3-27, 4-28, and 5-29 of SEQ ID NO:2. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-23 nucleobase sequence which is at least 84% complementary to a target sequence of a nucleotide sequence consisting of SEQ ID NO:3. More particularly, the targeting sequence may consist of 18, 19, 20, 21, 22, or 23 nucleobases. A 20-mer ASO, for example, could comprise a targeting sequence which is complementary to a target sequence selected from the set of positions 1-20, 2-21, 3-22, and 4-23 of SEQ ID NO:3. Other targeting sequence sizes could be selected using the shift method shown above for determining possible target sequences of SEQ ID NO: 1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-34 nucleobase sequence which is at least 84% complementary to a target sequence of a nucleotide sequence consisting of SEQ ID NO:4. More particularly, the targeting sequence may consist of 18, 19, 20, 21, 22, 23, 24, 25, 26, 27, 28, 29, 30, 31, 32, 33, or 34 nucleobases. A 25-mer ASO, for example, could comprise a targeting sequence which is complementary to a target sequence selected from the set of positions 1-25, 2-26, 3-27, 4-28, 5-29, 6-30, 7-31, 8-32, 9-33, and 10-34 of SEQ ID NO:4. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-29 nucleobase sequence which is at least 84% complementary to a target sequence of a nucleotide sequence consisting of SEQ ID NO:5. More particularly, the targeting sequence may consist of 18, 19, 20, 21, 22, 23, 24, 25, 26, 27, 28, or 29 nucleobases. A 25-mer ASO, for example, could comprise a targeting sequence which is complementary to a target sequence selected from the set of positions 1-25, 2-26, 3-27, 4-28, and 5-29 of SEQ ID NO:5. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-22 nucleobase sequence which is at least 84% complementary to a target sequence of a nucleotide sequence consisting of SEQ ID NO:6. More particularly, the targeting sequence may consist of 18, 19, 20, 21, or 22 nucleobases. A 20-mer ASO, for example, could comprise a targeting sequence which is complementary to a target sequence selected from the set of positions 1-20, 2-21, and 3-22 of SEQ ID NO:6. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-34 nucleobase sequence which is at least 84% complementary to a target sequence of a nucleotide sequence consisting of SEQ ID NO:7. More particularly, the targeting sequence may consist of 18, 19, 20, 21, 22, 23, 24, 25, 26, 27, 28, 29, 30, 31, 32, 33, or 34 nucleobases. A 25-mer ASO, for example, could comprise a targeting sequence which is complementary to a target sequence selected from the set of positions 1-25, 2-26, 3-27, 4-28, 5-29, 6-30, 7-31, 8-32, 9-33, and 10-34 of SEQ ID NO:7. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-50 nucleobase sequence which is at least 84% complementary to a target sequence of a nucleotide sequence consisting of SEQ ID NO:8. More particularly, the targeting sequence may consist of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, and 26-50 of SEQ ID NO:8. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-23 nucleobase sequence which is at least 84% complementary to a target sequence of a nucleotide sequence consisting of SEQ ID NO:9. More particularly, the targeting sequence may consist of 18, 19, 20, 21, 22, or 23 nucleobases. A 20-mer ASO, for example, could comprise a targeting sequence which is complementary to a target sequence selected from the set of positions 1-20, 2-21, 3-22, and 4-23 of SEQ ID NO:9. Other targeting sequence sizes could be selected using the shift method shown above for determining possible target sequences of SEQ ID NO: 1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-50 nucleobase sequence which is at least 84% complementary to a target sequence of a nucleotide sequence consisting of SEQ ID NO:10. More particularly, the targeting sequence may consist of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, and 26-50 of SEQ ID NO: 10. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-50 nucleobase sequence which is at least 84% complementary to a target sequence of a nucleotide sequence consisting of SEQ ID NO:11. More particularly, the targeting sequence may consist of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, and 26-50 of SEQ ID NO: 11. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-28 nucleobase sequence which is at least 84% complementary to a target sequence of a nucleotide sequence consisting of SEQ ID NO:12. More particularly, the targeting sequence may consist of 18, 19, 20, 21, 22, 23, 24, 25, 26, 27, or 28 nucleobases. A 25-mer ASO, for example, could comprise a targeting sequence which is complementary to a target sequence selected from the set of positions 1-25, 2-26, 3-27, and 4-28 of SEQ ID NO: 12. Other targeting sequence sizes could be selected using the shift method shown above for determining possible target sequences of SEQ ID NO: 1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-35 nucleobase sequence which is at least 84% complementary to a target sequence of a nucleotide sequence consisting of SEQ ID NO:13. More particularly, the targeting sequence may consist of 15, 16, 17, 18, 19, 20, 21, 22, 23, 24, 25, 26, 27, 28, 29, 30, 31, 32, 33, 34, or 35 nucleobases. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, and 11-35 of SEQ ID NO:13. Other targeting sequence sizes could be selected using the shift method shown above for determining possible target sequences of SEQ ID NO: 1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-34 nucleobase sequence which is at least 84% complementary to a target sequence of a nucleotide sequence consisting of SEQ ID NO:14. More particularly, the targeting sequence may consist of 18, 19, 20, 21, 22, 23, 24, 25, 26, 27, 28, 29, 30, 31, 32, 33, or 34 nucleobases. A 25-mer ASO, for example, could comprise a targeting sequence which is complementary to a target sequence selected from the set of positions 1-25, 2-26, 3-27, 4-28, 5-29, 6-30, 7-31, 8-32, 9-33, and 10-34 of SEQ ID NO: 14. Other targeting sequence sizes could be selected using the shift method shown above for determining possible target sequences of SEQ ID NO: 1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-35 nucleobase sequence which is at least 84% complementary to a target sequence of a nucleotide sequence consisting of SEQ ID NO:15. More particularly, the targeting sequence may consist of 18, 19, 20, 21, 22, 23, 24, 25, 26, 27, 28, 29, 30, 31, 32, 33, 34, or 35 nucleobases. In at least certain embodiments, the targeting sequence comprises a 4-nucleobase segment which is 100% complementary to the sequence 5'-ATGT-3' (positions 24-27) of SEQ ID NO: 15. In at least certain embodiments, the targeting sequence comprises a 7-nucleobase segment upstream and/or downstream of the sequence 5'-ATGT-3' of SEQ ID NO: 15 which is 100% complementary to the 7 nucleobases upstream and/or downstream of the sequence 5'-ATGT-3', respectively, of SEQ ID NO:15. In at least certain embodiments, the targeting sequence comprises a 10-nucleobase segment upstream and/or downstream of the sequence 5'-ATGT-3' of SEQ ID NO: 15 which is 100% complementary to the 10 nucleobases upstream and/or downstream of the sequence 5'-ATGT-3', respectively, of SEQ ID NO:15. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, and 11-35 of SEQ ID NO:15. Other targeting sequence sizes could be selected using the shift method shown above for determining possible target sequences of SEQ ID NO: 1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-50 nucleobase sequence which is at least 84% complementary to a target sequence of a nucleotide sequence consisting of SEQ ID NO:16. More particularly, the targeting sequence may consist of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases. In at least certain embodiments, the targeting sequence comprises a 4-nucleobase segment which is 100% complementary to the sequence 5'-AGGA-3' in positions 24-27 of SEQ ID NO: 16. In at least certain embodiments, the targeting sequence comprises a 7-nucleobase segment upstream and/or downstream of the sequence 5'-AGGA-3' in positions 24-27 of SEQ ID NO: 16 which is 100% complementary to the 7 nucleobases upstream and/or downstream, respectively, of the sequence 5'-AGGA-3' in positions 24-27 of SEQ ID NO:16. In at least certain embodiments, the targeting sequence comprises a 10-nucleobase segment upstream and/or downstream of the sequence 5'-AGGA-3' in positions 24-27 of SEQ ID NO: 16 which is 100% complementary to the 10 nucleobases upstream and/or downstream, respectively, of the sequence 5'-AGGA-3' in positions 24-27 of SEQ ID NO: 16. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, and 26-50 of SEQ ID NO:16. Other targeting sequence sizes could be selected using the shift method shown above for determining possible target sequences of SEQ ID NO: 1. In at least certain embodiments, the nucleobases of the targeting sequence are linked via a non-natural internucleoside backbone. In at least certain embodiments, the non-natural internucleoside backbone comprises phosphorodiamidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-36 nucleobase sequence which is at least 84% complementary to a target sequence of a nucleotide sequence consisting of SEQ ID NO:17. More particularly, the targeting sequence may consist of 18, 19, 20, 21, 22, 23, 24, 25, 26, 27, 28, 29, 30, 31, 32, 33, 34, 35, or 36 nucleobases. In at least certain embodiments, the targeting sequence comprises a 4-nucleobase segment which is 100% complementary to the sequence 5'-AGGT-3' (positions 24-27) of SEQ ID NO: 17. In at least certain embodiments, the targeting sequence comprises a 7-nucleobase segment upstream and/or downstream of the sequence 5'-AGGT-3' of SEQ ID NO: 17 which is 100% complementary to the 7 nucleobases upstream and/or downstream of the sequence 5'-AGGT-3', respectively, of SEQ ID NO: 17. In at least certain embodiments, the targeting sequence comprises a 10-nucleobase segment upstream and/or downstream of the sequence 5'-AGGT-3' of SEQ ID NO: 17 which is 100% complementary to the 10 nucleobases upstream and/or downstream of the sequence 5'-AGGT-3', respectively, of SEQ ID NO: 17. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, 11-35, and 12-36 of SEQ ID NO:17. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiamidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-43 nucleobase sequence which is at least 84% complementary to a target sequence of a nucleotide sequence consisting of SEQ ID NO:18. More particularly, the targeting sequence may consist of 18, 19, 20, 21, 22, 23, 24, 25, 26, 27, 28, 29, 30, 31, 32, 33, 34, 35, 36, 37, 38, 39, 40, 41, 42, or 43 nucleobases. In at least certain embodiments, the targeting sequence comprises a 4-nucleobase segment which is 100% complementary to the sequence 5'-AGCT-3' (positions 24-27) of SEQ ID NO: 18. In at least certain embodiments, the targeting sequence comprises a 7-nucleobase segment upstream and/or downstream of the sequence 5'-AGCT-3' of SEQ ID NO:18 which is 100% complementary to the 7 nucleobases upstream and/or downstream of the sequence 5'-AGCT-3', respectively, of SEQ ID NO:18. In at least certain embodiments, the targeting sequence comprises a 10-nucleobase segment upstream and/or downstream of the sequence 5'-AGCT-3' of SEQ ID NO: 18 which is 100% complementary to the 10 nucleobases upstream and/or downstream of the sequence 5'-AGCT-3', respectively, of SEQ ID NO: 18. A 25-mer ASO, for example, could comprise a targeting sequence which is complementary to a target selected from the set of positions 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, and 19-43 of SEQ ID NO:18. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiamidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-41 nucleobase sequence which is at least 84% complementary to a target sequence of a nucleotide sequence consisting of SEQ ID NO:19. More particularly, the targeting sequence may consist of 18, 19, 20, 21, 22, 23, 24, 25, 26, 27, 28, 29, 30, 31, 32, 33, 34, 35, 36, 37, 38, 39, 40, or 41 nucleobases. In at least certain embodiments, the targeting sequence comprises a 4-nucleobase segment which is 100% complementary to the sequence 5'-AGGT-3' (positions 24-27) of SEQ ID NO:19. In at least certain embodiments, the targeting sequence comprises a 7-nucleobase segment upstream and/or downstream of the sequence 5'-AGGT-3' of SEQ ID NO: 19 which is 100% complementary to the 7 nucleobases upstream and/or downstream of the sequence 5'-AGGT-3', respectively, of SEQ ID NO: 19. In at least certain embodiments, the targeting sequence comprises a 10-nucleobase segment upstream and/or downstream of the sequence 5'-AGGT-3' of SEQ ID NO: 19 which is 100% complementary to the 10 nucleobases upstream and/or downstream of the sequence 5'-AGGT-3', respectively, of SEQ ID NO:19. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, 11-35, 12-36, 13-37, 14-38, 15-39, 16-40, and 17-41 of SEQ ID NO:19. Other targeting sequence sizes could be selected using the shift method shown above for determining possible target sequences of SEQ ID NO: 1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-50 nucleobase sequence which is at least 84% complementary to a target sequence of a nucleotide sequence consisting of SEQ ID NO:20. More particularly, the targeting sequence may consist of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases. In at least certain embodiments, the targeting sequence comprises a 4-nucleobase segment which is 100% complementary to the sequence 5'-AGGG-3' (positions 24-27) of SEQ ID NO:20. In at least certain embodiments, the targeting sequence comprises a 7-nucleobase segment upstream and/or downstream of the sequence 5'-AGGG-3' of SEQ ID NO:20 which is 100% complementary to the 7 nucleobases upstream and/or downstream of the sequence 5'-AGGG-3', respectively, of SEQ ID NO:20. In at least certain embodiments, the targeting sequence comprises a 10-nucleobase segment upstream and/or downstream of the sequence 5'-AGGG-3' of SEQ ID NO:20 which is 100% complementary to the 10 nucleobases upstream and/or downstream of the sequence 5'-AGGG-3', respectively, of SEQ ID NO:20. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, and 26-50 of SEQ ID NO:20. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-50 nucleobase sequence which is at least 84% complementary to a target sequence of a nucleotide sequence consisting of SEQ ID NO:21. More particularly, the targeting sequence may consist of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases. In at least certain embodiments, the targeting sequence comprises a 4-nucleobase segment which is 100% complementary to the sequence 5'-CAGT-3' (positions 25-28) of SEQ ID NO:21. In at least certain embodiments, the targeting sequence comprises a 7-nucleobase segment upstream and/or downstream of the sequence 5'-CAGT-3' of SEQ ID NO:21 which is 100% complementary to the 7 nucleobases upstream and/or downstream of the sequence 5'-CAGT-3', respectively, of SEQ ID NO:21. In at least certain embodiments, the targeting sequence comprises a 10-nucleobase segment upstream and/or downstream of the sequence 5'-CAGT-3' of SEQ ID NO:21 which is 100% complementary to the 10 nucleobases upstream and/or downstream of the sequence 5'-CAGT-3', respectively, of SEQ ID NO:21. A 25-mer ASO, for example, could comprise a targeting sequence which is complementary to a target portion selected from the set of positions 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, and 26-50 of SEQ ID NO:21. Other targeting sequence sizes could be selected using the shift method shown above for determining possible target sequences of SEQ ID NO:1. One non-limiting example of an ASO which comprises a targeting sequence complementary to a target sequence of SEQ ID NO:21 is the vivo morpholino referred to elsewhere herein as "e515" (a.k.a. e5i5) which comprises a nucleobase targeting sequence 5'-CACAACCGTCCGCCACTCACTG-3' (SEQ ID NO:30) that is complementary to positions 25-46 of SEQ ID NO:21. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-50 nucleobase sequence which is at least 84% complementary to a target sequence of a nucleotide sequence consisting of SEQ ID NO:22. More particularly, the targeting sequence may consist of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases. In at least certain embodiments, the targeting sequence comprises a 4-nucleobase segment which is 100% complementary to the sequence 5'-AGAT-3' (positions 24-27) of SEQ ID NO:22. In at least certain embodiments, the targeting sequence comprises a 7-nucleobase segment upstream and/or downstream of the sequence 5'-AGAT-3' of SEQ ID NO:22 which is 100% complementary to the 7 nucleobases upstream and/or downstream of the sequence 5'-AGAT-3', respectively, of SEQ ID NO:22. In at least certain embodiments, the targeting sequence comprises a 10-nucleobase segment upstream and/or downstream of the sequence 5'-AGAT-3' of SEQ ID NO:22 which is 100% complementary to the 10 nucleobases upstream and/or downstream of the sequence 5'-AGAT-3', respectively, of SEQ ID NO:22. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, and 26-50 of SEQ ID NO:22. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiaminidate morpholine linkages.

In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-34 nucleobase sequence which is at least 84% complementary to a target sequence of a nucleotide sequence consisting of SEQ ID NO:23. More particularly, the targeting sequence may consist of 18, 19, 20, 21, 22, 23, 24, 25, 26, 27, 28, 29, 30, 31, 32, 33, or 34 nucleobases. In at least certain embodiments, the targeting sequence comprises a 4-nucleobase segment which is 100% complementary to the sequence 5'-AGGT-3' (positions 16-19) of SEQ ID NO:23. In at least certain embodiments, the targeting sequence comprises a 7-nucleobase segment upstream and/or downstream of the sequence 5'-AGGT-3' of SEQ ID NO:23 which is 100% complementary to the 7 nucleobases upstream and/or downstream of the sequence 5'-AGGT-3', respectively, of SEQ ID NO:23. In at least certain embodiments, the targeting sequence comprises a 10-nucleobase segment upstream and/or downstream of the sequence 5'-AGGT-3' of SEQ ID NO:23 which is 100% complementary to the 10 nucleobases upstream and/or downstream of the sequence 5'-AGGT-3', respectively, of SEQ ID NO:23. A 25-mer ASO, for example, could comprise a targeting sequence which is complementary to a target sequence selected from the set of positions 1-25, 2-26, 3-27, 4-28, 5-29, 6-30, 7-31, 8-32, 9-33, and 10-34 of SEQ ID NO:23. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-28 nucleobase sequence which is at least 84% complementary to a target sequence of a nucleotide sequence consisting of SEQ ID NO:24. More particularly, the targeting sequence may consist of 18, 19, 20, 21, 22, 23, 24, 25, 26, 27, or 28 nucleobases. In at least certain embodiments, the targeting sequence comprises a 4-nucleobase segment which is 100% complementary to the sequence 5'-GGAG-3' (positions 2-5) of SEQ ID NO:24. In at least certain embodiments, the targeting sequence comprises a 7-nucleobase segment downstream of the sequence 5'-GGAG-3' of SEQ ID NO:24 which is 100% complementary to the 7 nucleobases downstream of the sequence 5'-GGAG-3' of SEQ ID NO:24. In at least certain embodiments, the targeting sequence comprises a 10-nucleobase segment downstream of the sequence 5'-GGAG-3' of SEQ ID NO:24 which is 100% complementary to the 10 nucleobases downstream of the sequence 5'-GGAG-3' of SEQ ID NO:24. A 25-mer ASO, for example, could comprise a targeting sequence which is complementary to a target sequence selected from the set of positions 1-25, 2-26, 3-27, and 4-28 of SEQ ID NO:24. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-50 nucleobase sequence which is at least 84% complementary to a target sequence of a nucleotide sequence consisting of SEQ ID NO:25. More particularly, the targeting sequence may consist of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases. In at least certain embodiments, the targeting sequence comprises a 4-nucleobase segment which is 100% complementary to the sequence 5'-AGGT-3' (positions 24-27) of SEQ ID NO:25. In at least certain embodiments, the targeting sequence comprises a 7-nucleobase segment upstream and/or downstream of the sequence 5'-AGGT-3' of SEQ ID NO:25 which is 100% complementary to the 7 nucleobases upstream and/or downstream of the sequence 5'-AGGT-3', respectively, of SEQ ID NO:25. In at least certain embodiments, the targeting sequence comprises a 10-nucleobase segment upstream and/or downstream of the sequence 5'-AGGT-3' of SEQ ID NO:25 which is 100% complementary to the 10 nucleobases upstream and/or downstream of the sequence 5'-AGGT-3', respectively, of SEQ ID NO:25. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, and 26-50 of SEQ ID NO:25. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-50 nucleobase sequence which is at least 84% complementary to a target sequence of a nucleotide sequence consisting of SEQ ID NO:26. More particularly, the targeting sequence may consist of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases. In at least certain embodiments, the targeting sequence comprises a 4-nucleobase segment which is 100% complementary to the sequence 5'-AGCC-3' in positions 24-27 of SEQ ID NO:26. In at least certain embodiments, the targeting sequence comprises a 7-nucleobase segment upstream and/or downstream of the sequence 5'-AGCC-3' in positions 24-27 of SEQ ID NO:26 which is 100% complementary to the 7 nucleobases upstream and/or downstream, respectively, of the sequence 5'-AGCC-3' in positions 24-27 of SEQ ID NO:26. In at least certain embodiments, the targeting sequence comprises a 10-nucleobase segment upstream and/or downstream of the sequence 5'-AGCC-3' in positions 24-27 of SEQ ID NO:26 which is 100% complementary to the 10 nucleobases upstream and/or downstream, respectively, of the sequence 5'-AGCC-3' in positions 24-27 of SEQ ID NO:26. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, and 26-50 of SEQ ID NO:26. Other targeting sequence sizes could be selected using the shift method shown above for determining possible target sequences of SEQ ID NO: 1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-50 nucleobase sequence which is at least 84% complementary to a target sequence of a nucleotide sequence consisting of SEQ ID NO:27. More particularly, the targeting sequence may consist of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases. In at least certain embodiments, the targeting sequence comprises a 4-nucleobase segment which is 100% complementary to the sequence 5'-AGGT-3' (positions 24-27) of SEQ ID NO:27. In at least certain embodiments, the targeting sequence comprises a 7-nucleobase segment upstream and/or downstream of the sequence 5'-AGGT-3' of SEQ ID NO:27 which is 100% complementary to the 7 nucleobases upstream and/or downstream of the sequence 5'-AGGT-3', respectively, of SEQ ID NO:27. In at least certain embodiments, the targeting sequence comprises a 10-nucleobase segment upstream and/or downstream of the sequence 5'-AGGT-3' of SEQ ID NO:27 which is 100% complementary to the 10 nucleobases upstream and/or downstream of the sequence 5'-AGGT-3', respectively, of SEQ ID NO:27. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, and 26-50 of SEQ ID NO:27. Other targeting sequence sizes could be selected using the shift method shown above for determining possible target sequences of SEQ ID NO:1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

In certain embodiments, the antisense compound comprises an antisense oligonucleotide comprising a targeting sequence consisting of an 18-46 nucleobase sequence which is at least 84% complementary to a target sequence of a nucleotide sequence consisting of SEQ ID NO:28. More particularly, the targeting sequence may consist of 18, 19, 20, 21, 22, 23, 24, 25, 26, 27, 28, 29, 30, 31, 32, 33, 34, 35, 36, 37, 38, 39, 40, 41, 42, 43, 44, 45, or 46 nucleobases. In at least certain embodiments, the targeting sequence comprises a 4-nucleobase segment which is 100% complementary to the sequence 5'-AGGA-3' (positions 24-27) of SEQ ID NO:28. In at least certain embodiments, the targeting sequence comprises a 7-nucleobase segment upstream and/or downstream of the sequence 5'-AGGA-3' of SEQ ID NO:28 which is 100% complementary to the 7 nucleobases upstream and/or downstream of the sequence 5'-AGGA-3', respectively, of SEQ ID NO:28. In at least certain embodiments, the targeting sequence comprises a 10-nucleobase segment upstream and/or downstream of the sequence 5'-AGGA-3' of SEQ ID NO:28 which is 100% complementary to the 10 nucleobases upstream and/or downstream of the sequence 5'-AGGA-3', respectively, of SEQ ID NO:28. A 25-mer ASO, for example, could comprise a targeting sequence which is complementary to a target sequence selected from the set of positions 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, and 22-46 of SEQ ID NO:28. Other targeting sequence sizes could be selected using the shift method shown above for determining possible target sequences of SEQ ID NO: 1. In at least certain embodiments, the nucleobases of the targeting sequence are linked via a non-natural internucleoside backbone. In at least certain embodiments, the non-natural internucleoside backbone comprises phosphorodiaminidate morpholine linkages. In at least certain embodiments, the antisense compound comprises a cell-penetration enhancing moiety linked to the oligonucleotide.

As noted above, various inflammatory diseases (interferonopathies) are exacerbated by the production of IFN-alpha. Therefore, certain embodiments of the present disclosure provide an antisense compound for use in a method to treat IFN-alpha-associated inflammatory diseases (disorders, conditions) by way of modulating the production of IFN-alpha through inhibiting the production of ARID3a protein. Limiting IFN-alpha production is useful in treating inflammatory diseases, especially SLE, because increased levels of IFN-alpha are associated with inflammation and disease activity in SLE patients. Because there is a strong association between numbers of ARID3a$^+$ B lymphocytes, increased disease activity, and increased levels of IFN-alpha, certain embodiments of this disclosure address how ARID3a expression contributes to autoimmunity in SLE. Through inhibiting ARID3a+ transcription and/or translation, production of IFN-alpha is decreased, which can be an effective way to treat various inflammatory diseases, including (but not limited to) lupus erythematosus, systemic lupus erythematosus, rheumatoid arthritis, Sjogren's syndrome, Down syndrome, and other interferonopathies. It can also be used to treat virally-induced conditions with inflammation due to increased levels of IFN-alpha, including (but not limited to) herpes viruses, Epstein Barr virus, mononucleosis, and varicella zoster.

Therefore, without wishing to be bound by theory, in some embodiments, the administration of an anti-ARID3a antisense oligonucleotide is believed to decrease the expression of ARID3a mRNA. In particular embodiments, the decrease in the expression of ARID3a mRNA comprises the interference in the function of the ARID3a DNA sequence (ARID3a gene), typically resulting in decreased replication and/or transcription of the ARID3a DNA. In other embodiments, the decrease in expression of ARID3a mRNA by an anti-ARID3a oligonucleotide results from interference in function of ARID3a RNA, typically resulting in impaired splicing of transcribed ARID3a RNA (pre-mRNA) to yield mature mRNA species, decreased ARID3a RNA stability, decreased translocation of the ARID3a mRNA to the site of protein translation and impaired translation of protein from mature mRNA. In other embodiments, the decrease in expression of ARID3a mRNA by an anti-ARID3a oligonucleotide comprises the decrease in cellular ARID3a mRNA number or cellular content of ARID3a mRNA. In some embodiments, the decrease in expression of ARID3a mRNA by an anti-ARID3a oligonucleotide comprises the down-regulation or knockdown of ARID3a gene expression. In other embodiments, the decrease in expression of ARID3a mRNA by an anti-ARID3a oligonucleotide comprises the decrease in ARID3a protein expression or cellular ARID3a protein content. In some embodiments, the present disclosure is directed to compounds for and methods of administering synthetic oligonucleotides that decrease the expression of human ARID3a mRNA or human ARID3a protein. Further, in other embodiments, the administration to a subject of anti-ARID3a oligonucleotides as disclosed herein results in the decrease in production of cellular IFN-alpha, for example due to a decrease in transcription and/or translation of ARID3a precursor mRNA or mature mRNA, causing a decrease in cellular ARID3a.

In some embodiments, the administration of an effective amount of an anti-ARID3a oligonucleotide decreases ARID3a mRNA transcription rate, cellular ARID3a mRNA level, ARID3a expression rate, or cellular ARID3a protein level of ARID3a$^+$ cells (including but not limited to B lymphocytes, dendritic cells, and neutrophils) by at least 5%, at least 10%, at least 15%, at least 20%, at least 25%, at least 30%, at least 35%, at least 40%, at least 45%, at least 50%, at least 60%, at least 70%, at least 80%, or at least 90% compared to controls. In additional embodiments, the administration of an effective amount of an anti-ARID3a oligonucleotide decreases IFN-alpha protein by at least 5%, at least 10%, at least 15%, at least 20%, at least 25%, at least 30%, at least 35%, at least 40%, at least 45%, at least 50%, at least 60%, at least 70%, at least 80%, or at least 90% compared to controls. In further embodiments, the administration of an effective amount of an anti-ARID3a oligonucleotide decreases or reverses IFN-alpha-associated inflammatory diseases such as SLE and others as discussed elsewhere herein or otherwise known in the art.

EXAMPLES

Certain novel embodiments of the present disclosure, having now been generally described, will be more readily understood by reference to the following examples, which are included merely for purposes of illustration of certain aspects and embodiments of the present disclosure, and are not intended to be limiting. The following examples are to be construed, as noted above, only as illustrative, and not as limiting of the present disclosure in any way whatsoever. Those skilled in the art will promptly recognize appropriate variations from the various compositions, structures, components, procedures and methods.

Example 1: Role of ARID3a in the Production of IFN-Alpha

Experiments were performed to further investigate the role of ARID3a in the production of IFN-alpha.
Material and Methods
Clinical Patient Characteristics
Clinical presentations are diverse among SLE patients. Therefore, 11 American College of Rheumatology (ACR) criteria are used for disease classification, which include clinical and immunological criteria. Healthy controls (n=7) and patients (n=22) who met a minimum of four American College of Rheumatology Classification Criteria for SLE were recruited after informed consent from the Oklahoma Medical Research Foundation Clinical Pharmacology clinic (Oklahoma City, Okla.) as part of the Oklahoma Lupus Cohort (IRB compliance #09-07 and #06-19), in accordance with the Declaration of Helsinki. Peripheral blood mononuclear cells were analyzed for ARID3a expression. SLE samples were defined as ARID3a$^H$ if numbers of ARID3A$^+$ B cells >2 standard deviations above the average numbers of ARID$^3$a$^+$ B cells in healthy controls (9,830 ARID3a$^+$ B cells/ml).

Plasma Assessment

Due to low IFN-alpha levels in peripheral blood, ELISA-based methods for quantitation can be unreliable. WISH endothelial cells express the IFN-alpha receptor and have low/-endosomal Toll-like receptor (TLR) expression, and do not trigger endogenous IFN pathways. Patient plasma was measured for the ability to elevate expression of IFN-alpha-inducible genes using the human WISH reporter cell line (ATCC, CCL-25; gift from S. Kovats) by qRT-PCR. Briefly, WISH epithelial cells (50,000 cells/well) were cultured 1:2 with SLE patient or control plasma and RPMI supplemented with 10% FBS, for 6 hours at 37° C. prior to lysis for RNA isolation. Data were normalized to HPRT1 or GAPDH. Each value was expressed relative to the average normalized IFIT1 expression induced by 6 healthy control plasma samples.

RT-PCR, Quantitative RT-PCR, and BioMark HD

Total RNA was isolated using Tri-Reagent (Molecular Research Center, Inc., Cincinnati, Ohio). For RT-PCR, cDNA synthesis was performed at 37° C. for 1 hour with M-MLV reverse transcriptase (Promega, Madison, Wis.) and random primers (Promega), and amplification was for 40 cycles: 57-60° C. for 30 s, 72° C. for 1 min, and 95° C. for 30 sec, according to the gene of interest. Real-Time qPCR was preformed according to the manufacturer's protocol using the 7500 Real-Time PCR System (Applied Biosystems, Foster City, Calif.) with SYBR Green PCR Master Mix (Qiagen, Hilden, Germany) and gene-specific primers. Technical replicates were performed in duplicate or triplicate. Target gene expression was normalized to GAPDH or HPRT1, and expressed relative to gene expression in positive (EBV-transformed B cells or 293T) or B cells from healthy individuals for the Biomark HD data. The IFN-alpha primers used for qRT-PCR of SLE B cells amplified ~70% of the IFN-alpha subtype genes and quantified the collective expression of those genes. For BioMark HD assays, fluorescence activated cell sorted (FACS) CD20$^+$ B lymphocytes were isolated using a FACSAria™ II cell sorter (BD Biosciences, San Jose, Calif.). RNA was isolated as above, then quantified and assessed for integrity using Agilent Total RNA Pico chips on the 2100 Bioanalyzer (Agilent Technologies, Boblingen, Germany). The DELTAgene assay designer was used for primer design for optimal performance on the Biomark HD system. Primers were generated using the DELTAgene assay kit (Fluidigm, San Francisco, Calif.) optimized for DELTAgene assays on the BioMark HD system, and primer pair specificity was determined via melting curve analysis at 400 nM. The cDNA preparation (Fluidigm preamp master mix, PM100-5580) and amplification (Fluidigm, DELTAgene assay kit) were used at a final 1:10 dilution in DNA suspension buffer. The quantitative PCR was conducted on the BioMark HD system, and transcript expression was assessed using the Gene Expression 96.96 IFC chip (Fluidigm) using the standard DELTAgene assay. Thermocycling parameters included an initial phase of 98° C. for 40 s followed by 40 cycles, consisting of 95° C. for 10 s and 60° C. for 40 s. Raw quantification cycle (cycle threshold [Ct]) values were obtained from the Fluidigm BioMark software; along with quality control calls, Ct values that failed quality control were dropped from subsequent analyses. GAPDH was used as a housekeeping standard, and DDCt values were calculated from averaged duplicates. A list of PCR primer sequences for the genes assessed is described in Table 1 of US Provisional Patent Application Ser. No. 62/362,775, filed Jul. 15, 2016, the entirety of which is hereby expressly incorporated by reference herein.

Methyl-Seq

Purified genomic DNA was isolated from frozen aliquots containing PBMCs obtained from two ARID3a high and two ARID3a low expressing SLE patients using standard phenol/Chloroform extraction protocols. Sample gDNA was fragmented on a Covaris S2 sonicator (Covaris, Woburn, Mass.) to an average size of ~350 bp in length. Fragmented DNA was subjected to MethylMiner Methylated DNA Enrichment Kit (Life Technologies, Carlsbad, Calif.), according to the manufacturer's protocol. Illumina sequencing libraries were prepared using the Illumina Truseq DNA LT Sample Prep Kit (Illumina, San Diego, Calif.) per the manufacturer's protocol by the OMRF Genomics Core facility. The samples were pooled, and libraries were sequenced on an Illumina Hiseq 2000 instrument with paired-end 100 bp reads. Quality control metrics were assessed with Picard tools v. (Broad Institute, Cambridge, Mass. After sequencing, reads were aligned to the human reference genome hg19 using the aligner BWA-MEM followed by local realignment around problematic indel sequences using the Genome Analysis Tool Kit (GATK). Genes with statistically significant methylation differences were defined using EpiCenter v. 1-6-1-8. Methylation differences were tested over promoters of the genes, defined as 2,000 bp regions upstream of gene transcription start sites. The differentially methylated regions were visualized in the IGV integrative genomics viewer. For visualization in the UCSC Genome Browser, BigWig files were created from the final BAM files using a combination of BEDTools and UCSC conversion utilities.

ARID3a Knockdown

EBV-transformed lymphoblastoid (LCL) B cell lines were plated into triplicate wells (40,000 cells/well) and transfected with 3 lentiviral constructs (MOI 3) containing ARID3a shRNA and co-expressing GFP (1-3), or a control vector expressing a scrambled sequence and GFP, as previously described. Briefly, cells were cultured in RPMI 1640 supplemented with 4% FBS for 36 hours at 37° C., and lysed for RNA isolation, cDNA synthesis, and qPCR after 36 hours (n=3).

Flow Cytometry

PBMCs were isolated from heparinized peripheral blood (~15 ml) with Ficoll-Paque Plus (GE Healthcare, Little Chalfont, UK), and stained with the following fluorochrome-labeled antibodies: CD19 PE-Cy5, CD10 Pacific Blue (BioLegend, San Diego, Calif.), IgD PerCP-Cy5.5, CD27 PE-Cy7, CD38 Alexa Fluor 700 (BD Pharmingen, San Jose, Calif.), and IgM APC (Southern Biotech, Birmingham, Ala.). PBMCs were fixed (3% paraformaldehyde) and permeabilized (0.1% Tween-20) prior to staining with goat anti-human ARID3a antibody and a rabbit anti-goat IgG FITC secondary (Invitrogen, Carlsbad, Calif.). Gating for individual B cell subsets was used with the following B (CD20$^+$) cell subset markers: transitional (IgD$^+$CD27$^-$CD10+), naïve (IgD$^+$CD27$^-$CD10$^+$), MZ-like Memory (IgD$^+$CD27$^+$), Memory (IgD$^+$CD27$^+$), and Double-negative (DN) (IgD-CD27) B cells. Non-B cells were excluded using the following markers on the fluorochrome, APC: T cells (CD3), Monocytes, macrophages, and granulocytes (CD14); NK cells, neutrophils, macrophage, and dendritic cells (CD16); and NK and NKT cells (CD56). Isotype controls (Caltag (Carlsbad, Calif.), BD Pharmingen (San Jose, Calif.), and eBioscience (San Diego, Calif.)) were used for gating. Data (500,000 events per sample) were collected using an LSRII (BD Biogenics, San Jose, Calif.) and FACS-Diva (BD Biosciences, San Jose, Calif.) software version 4.1 and were analyzed using FlowJo (Tree Star, Ashland, Oreg.) software version 9.5.2.

Statistics

GraphPad Prism 6 was used for all statistical analyses. A two-tailed Student's T test or the nonparametric Mann-Whitney test was used for data comparing 2 groups. A one-way ANOVA was used for comparisons between 3 groups, followed by Turkey or Dunn's posttest to correct for multiple comparisons. All statistical tests, and corresponding P values, are indicated in the figure legends. P values <0.05 were considered significant and are indicated with the following symbols in the figures: *P<0.05, P<0.01, *P<0.001.

Results

ARID3a is Associated with IFN-Alpha Expression

ARID3a over-expression in SLE was postulated to be associated with differential gene regulation in total PBMCs. Because numbers of cells expressing ARID3a in individuals vary over time, division of SLE samples based on total numbers of ARID3a$^+$ B cells allowed for better evaluation of phenotypes directly associated with ARID3a expression. Others have shown differential methylation patterns in SLE PBMCs compared to PBMCs from healthy controls. Without wishing to be bound by theory, it was hypothesized that ARID3a expression might ultimately affect the methylation status of multiple promoters, providing clues regarding which genes might be dysregulated in patient samples with increased numbers of ARID3a$^+$ B cells (ARID3a$^H$) versus samples with normal numbers of ARID3a-expressing B cells (ARID3a$^N$). Genome-wide methyl-seq analyses of total PBMC samples from two ARID3a$^H$ and two ARID3a$^N$ designated SLE patient samples indicated methylation was globally higher across all chromosomes in the ARID3a$^H$ samples compared to ARID3a$^N$ samples. Promoter hypermethylation is typically correlated with gene repression. However, PBMCs from ARID3a$^H$ SLE patients showed hypomethylation of several IFN-alpha promoters, including IFNA 2, 5, 6, 8, 10, 14, 16, and 21, compared to ARID3a$^N$ SLE PBMCs (FIG. 1A), implying that PBMCs from samples with increased numbers of ARID3a$^+$ B cells express IFN-alpha. Additionally, a review of data from the ENCODE group indicated potential ARID3a binding sites in promoters of IFN-alpha subtype genes in some human cell lines, indicating that ARID3a could participate in regulation of those genes.

Figure 1B:
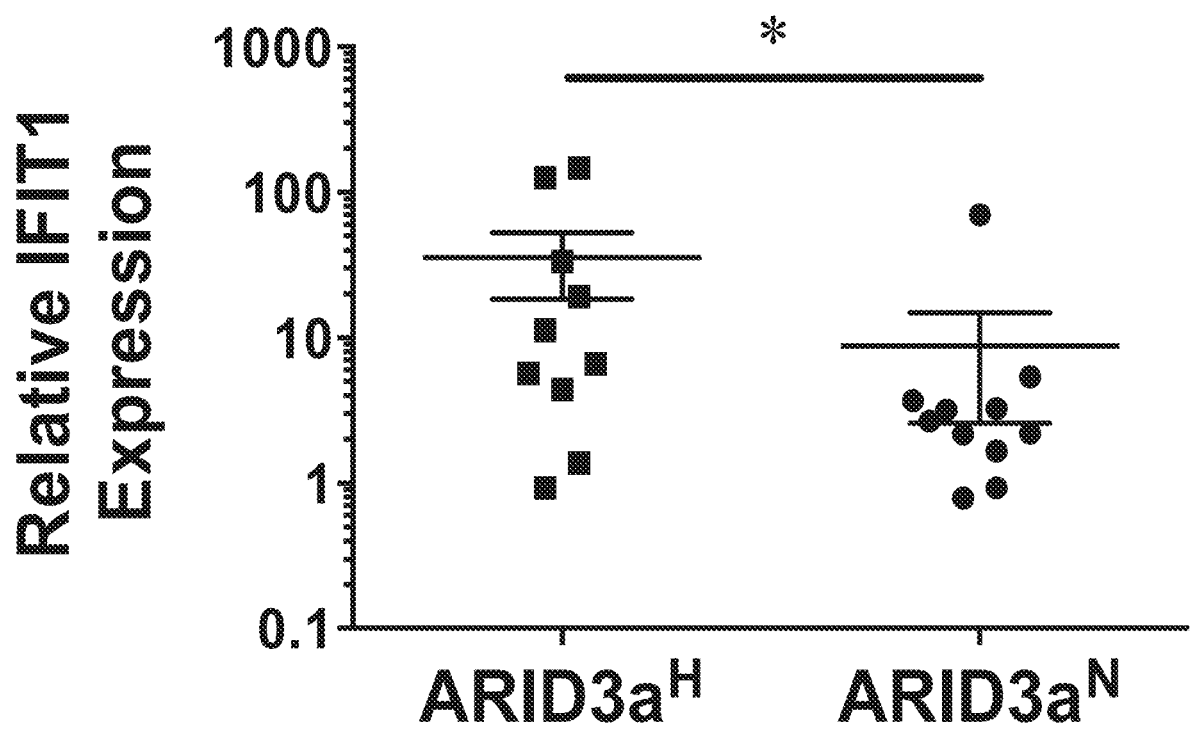
FIG. 1B shows plasma from ARID3a$^H$ (n=10) and ARID3a$^N$ (n=1) SLE patients (symbols) that were tested for the ability to elicit expression of the interferon-signature gene, IFIT1, by qRT-PCR using the WISH reporter cell line. Means, standard errors, and significance (Mann-Whitney, *p<0.05) are shown.

To determine if increased numbers of ARID3a$^+$ SLE B lymphocytes were associated with elevated circulating IFN-alpha, ARID3a$^H$ and ARID3a$^N$ plasma samples were assessed for IFN-alpha levels. Using a standard reporter assay allowing measurement of interferon-responsive genes by qRT-PCR, it was found that ARID3a$^H$ SLE plasma samples showed significantly higher expression (p<0.05) of the IFN-alpha response gene, IFIT1, compared to ARID3a$^N$ SLE plasma samples (FIG. 1B). These data indicate that plasma from patients with increased numbers of ARID3a$^+$ B cells was more effective at inducing IFN-alpha-stimulated gene expression than plasma from ARID3a$^N$ SLE samples, indicating that IFN-alpha levels were higher in these samples.

Figure 1C:
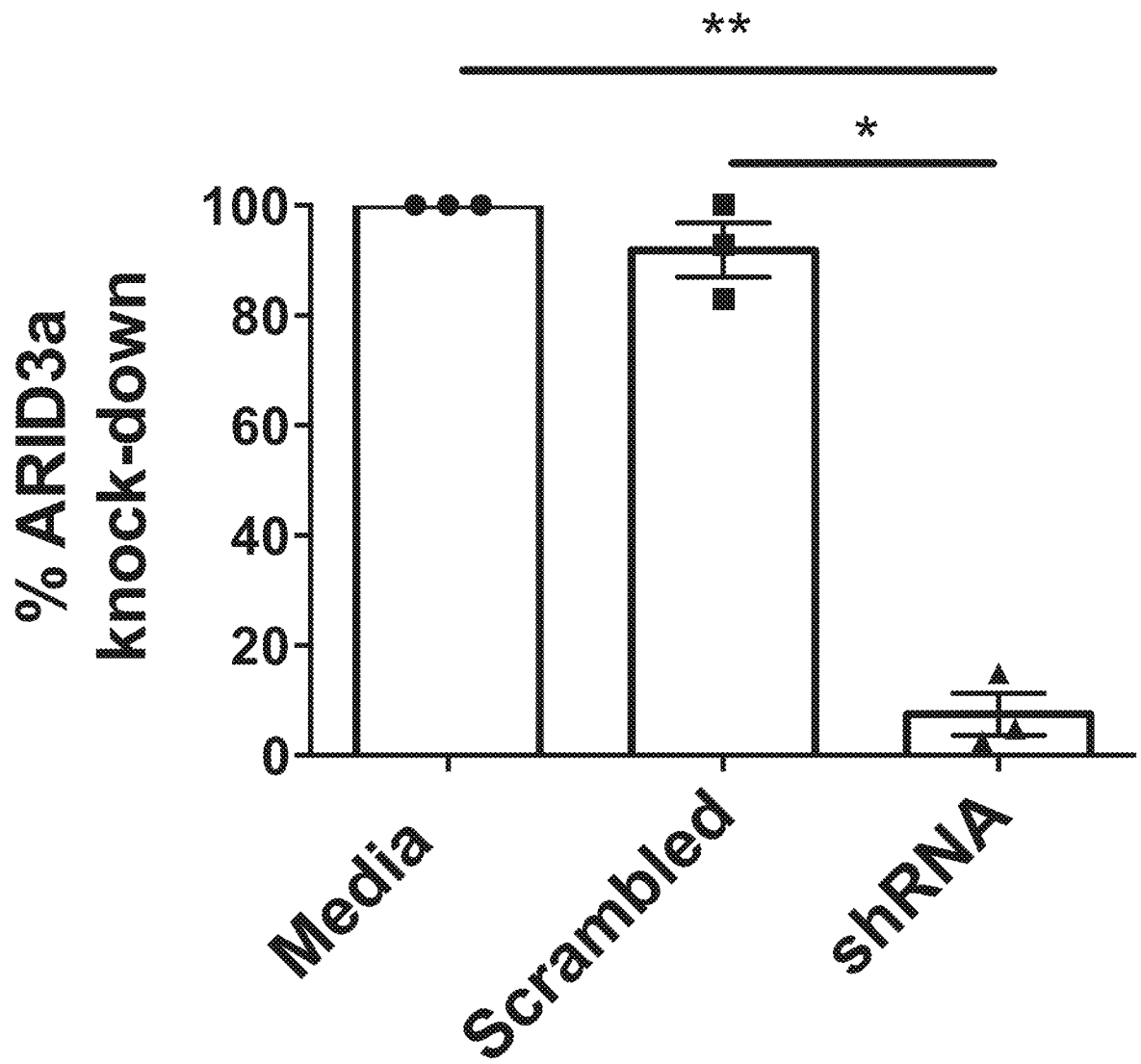
FIG. 1C shows percentages of ARID3a expression in EBV-transformed B cell lines with scrambled shRNA or ARID3a shRNA-treatment relative to media control.
Figure 1D:
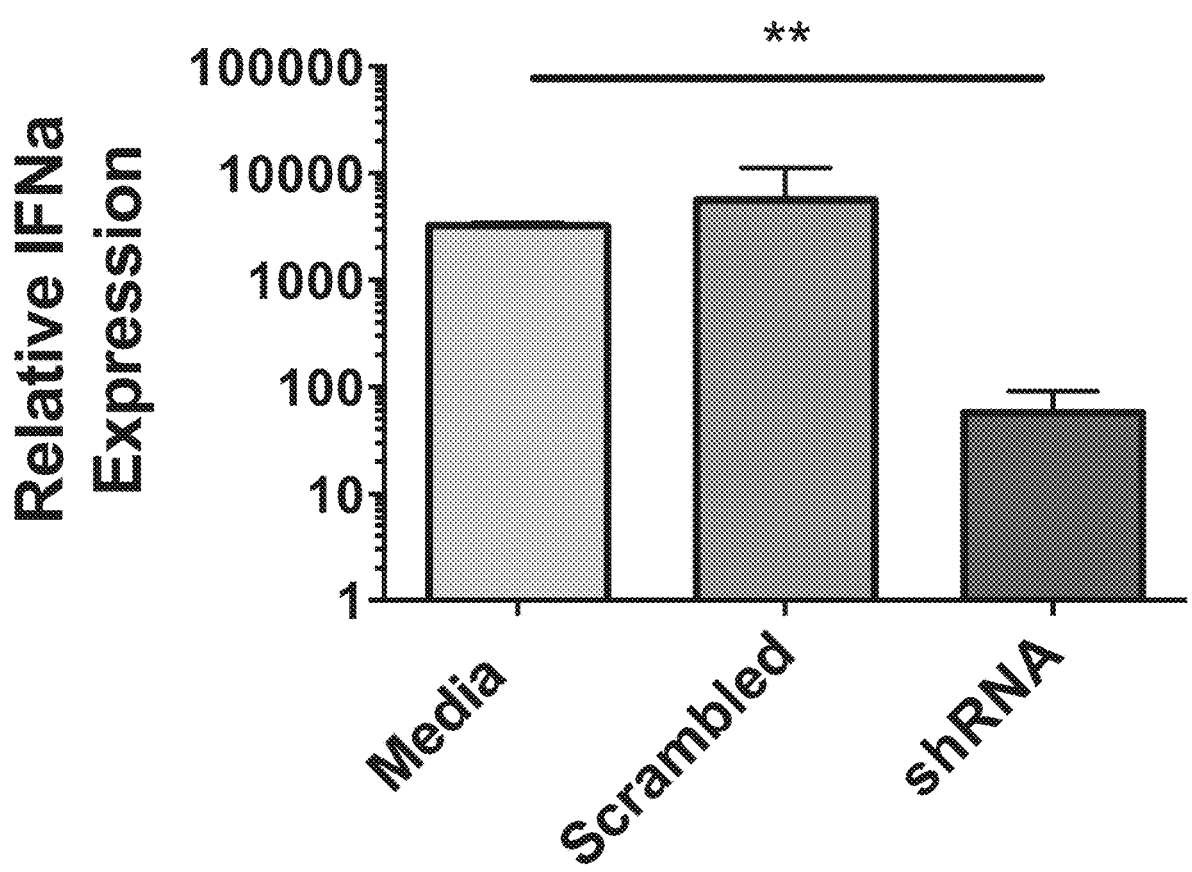
FIG. 1D shows IFN-alpha expression assessed by qRT-PCR of EBV-transformed B cell lines after treatment in FIG. 1C.
Figure 1E:
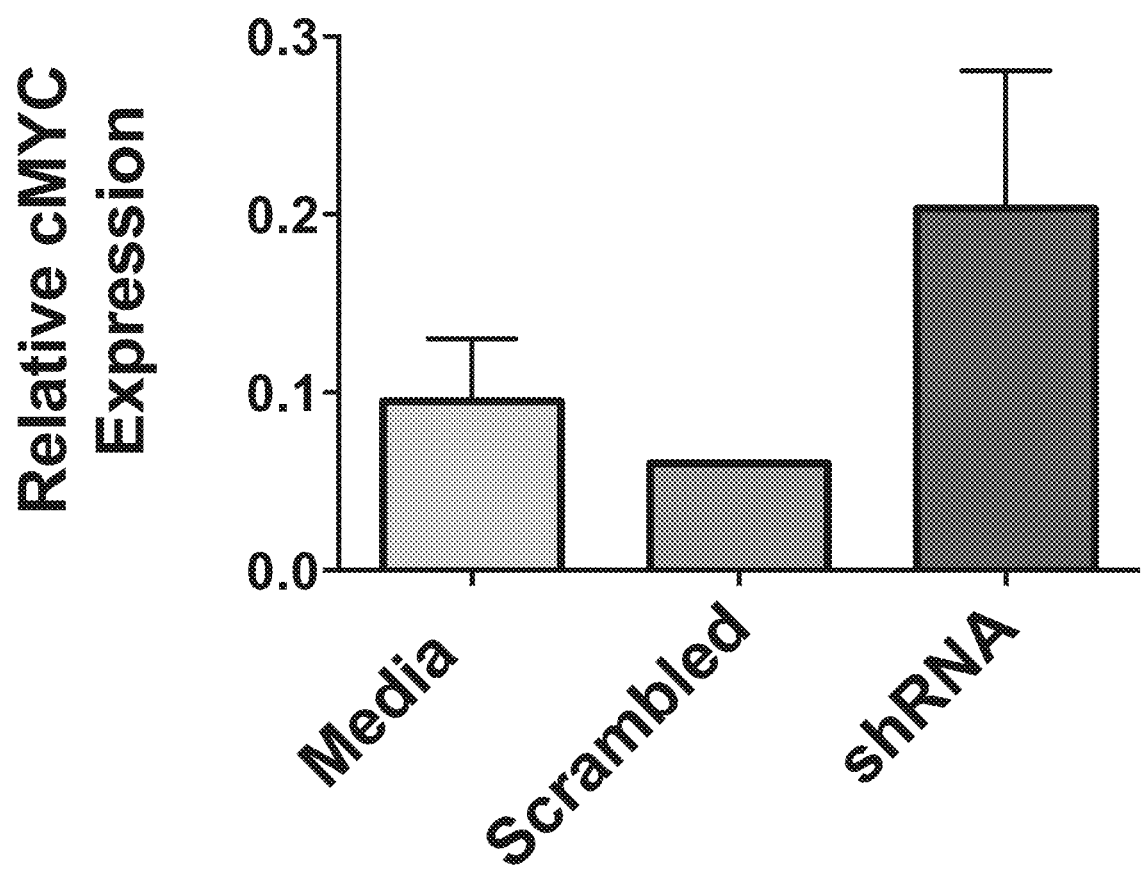
FIG. 1E shows cMyc expression assessed by qRT-PCR of EBV-transformed B cell lines after treatment in FIG. 1C.

Human lymphoblastoid B cell lines generated by infection with the Epstein Barr virus (EBV), express IFN-alpha. Moreover, it was observed that all EBV-transformed cell lines express ARID3a, and others showed that ARID3a is necessary for expression of EBV latency proteins. To test the requirement of ARID3a for IFN-alpha expression, EBV-transformed B cells were infected with lentivirus expressing ARID3a shRNA or scrambled control shRNA. Primers designed to amplify 6 of 12 highly homologous IFN-alpha subtype gene products were demonstrated to yield appropriate sized products by RT-PCR using several EBV lines (see FIGS. 1A-E, 6A, and 6B). Thirty-six hours post-infection, expression of ARID3a and IFN-alpha was determined via qRT-PCR (FIGS. 1C-D). While scrambled control shRNA did not significantly alter expression of ARID3a or IFN-alpha, ARID3a knockdown decreased IFN-alpha levels by more than 95%. However, expression of cMyc (FIG. 1E), a gene previously determined to increase after ARID3a knockdown in 293T cells, was increased, indicating that RNA expression was not globally affected by ARID3a inhibition. These data indicate expression of IFN-alpha in EBV-transformed B cells requires ARID3a.

Figure 2A:
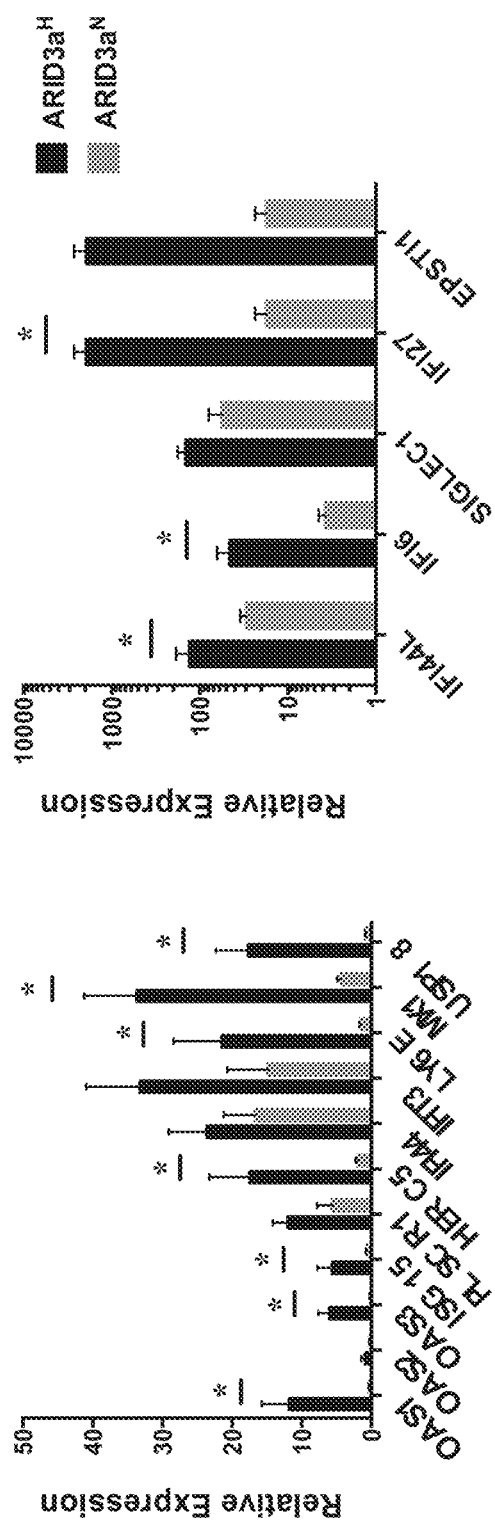
FIG. 2A shows that innate and IFN-alpha signature genes are upregulated in association with ARID3a in SLE patient B cells. RNA from isolated CD20$^+$ SLE patient B cells (3 each ARID3a$^H$ and ARID3a$^N$) was evaluated by Biomark HD qRT-PCR for interferon signature genes and other innate signaling pathway genes. Means, standard errors, and significance of genes upregulated >2-fold by Student's T test (*p) are shown.
Figure 2B:
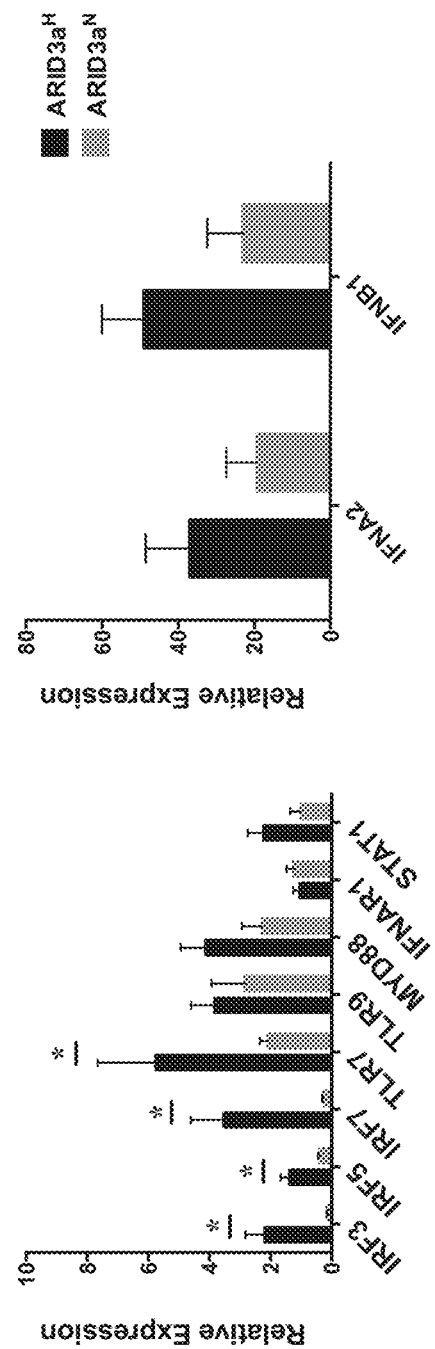
FIG. 2B shows that innate and IFN-alpha signaling pathway genes are upregulated in association with ARID3a in SLE patient B cells. RNA from isolated CD20$^+$ SLE patient B cells (3 each ARID3a$^H$ and ARID3a$^N$) was evaluated by Biomark HD qRT-PCR for interferon signature genes where gene expression was normalized to HPRT1. Means, standard errors, and significance of genes upregulated >2-fold by Student's T test (*p) are shown.
Figure 3A:
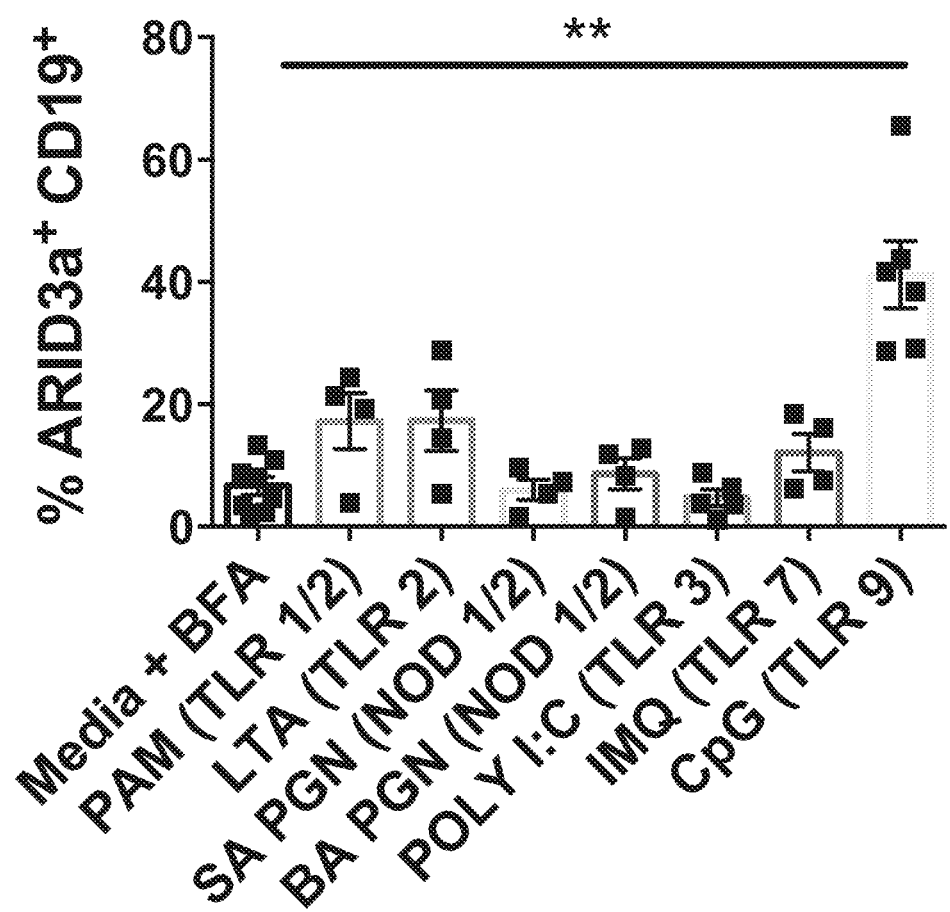
FIG. 3A shows healthy control B cell expressing ARID3a upon stimulation via TLR 9 using flow cytometry to assess percentage of ARID3a$^+$ CD19$^+$ B cells from 4-6 healthy controls after stimulation (18-24 hours) with PAM, LTA, SA PGN, BA PGN, Poly I:C, IMQ, and CpG. Means, standard errors, and significance (Paired T test, **p<0.01) are shown.
Figure 3B:
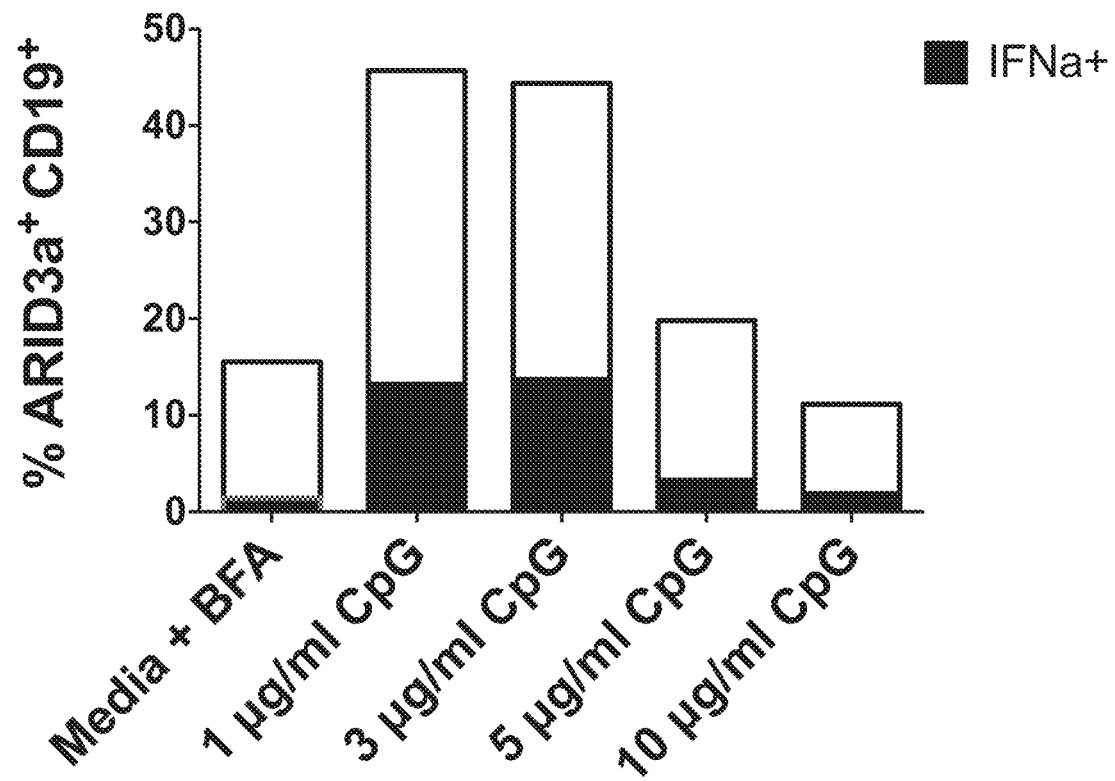
FIG. 3B shows representative percentages of ARID3a$^+$ and IFN-alpha-expressing B cells in response to increasing concentrations of CpG.

Expression of IFN-Alpha Signature Genes is Elevated in B Cells with Increased ARID3a IFN can exert autocrine effects on cells that produce it. To determine if IFN-alpha-responsive genes typically assessed in SLE were upregulated in B lymphocytes from ARID3a$^H$ versus ARID3a$^N$ B cells, FACS-purified ARID3a$^H$ (n=3) and ARID3a$^N$ (n=3) CD20$^+$ cells were evaluated for expression of IFN-alpha pathway genes via BioMark HD qRT-PCR. ARID3a$^H$ B cells showed higher expression (>10-fold) of ARID3a mRNA versus ARID3a$^N$ samples (Table 2), and had significant expression (>2 fold) of 11 IFN signature genes versus ARID3a$^N$ B cells (see Table 3, FIG. 2A). One IFN-alpha subtype gene, IFNA2α, was included on the array; however, there were no significant differences in expression between ARID3a-based patient groups (FIG. 3B). Additional genes involved in the IFN-alpha pathway, including IRF3, IRF5, and IRF7, showed increased expression in ARID3a$^H$ versus ARID3a$^N$ B cells (FIG. 2B). These data indicate genes involved in the IFN-alpha pathway are upregulated in ARID3a$^+$ SLE B cells, associating these cells with responses to IFN-alpha, indicating that those cells may have been previously exposed to IFN.

TABLE 2

Unregulated genes in ARID3a$^H$ versus ARID3a$^N$ SLE B cells

| Gene | P-value |
| --- | --- |
| Upregulated | |
| ARID3a | 0.0008 |
| OAS3 | 0.0018 |
| OAS1 | 0.0007 |
| HERC5 | 0.0043 |
| ISGI5 | 0.0118 |
| Ly6E | 0.0023 |
| MX1 | 0.0009 |
| USP18 | 0.0010 |
| IFI44L | 0.0369 |
| IFI6 | 0.0227 |
| IFI27 | 0.0034 |
| EPSTI1 | 0.0034 |
| IRF 3 | 0.0008 |
| IRF 5 | 0.0034 |
| IRF 7 | 0.0006 |
| TLR 7 | 0.0165 |
| BCL2L1 | 0.0049 |
| BCL2 | 0.0081 |

*Upregulated or downregulated >2 fold;
IFN signature genes are in bold

TABLE 3

Summary of B cell array data

| |
| --- |
| Upregulated* genes in ARID3a$^H$ vs. ARID3a$^N$ SLE B cells |
| ARID3a, OAS1, OAS3, HERC5, ISGI5, Ly6E, MX1, USP18, IFI44L, IFI6, IFI27, EPSTI1, IRF3, IRF5, IRF7, TLR7, BCL2L1, and BCL2 |
| Upregulated* genes in SLE vs. Control B cells |
| IFNA2, IFNB1, IFI44, IFIT3, IFI44L, IFI6, IFI27, EPSTI1, SIGLEC1, and TLR7 |
| Upregulated* genes in Stim. vs. Unstim. Control B cells |
| IFNA2, IFNRA1, IFNB1, EPSTI1, HERC5, IFI44L, IFIT3, MX1, Ly6E, OAS1, PLSCR1, OAS3, IRF3, TLR7, and TLR9 |
| Downregulated genes in Stim. vs. Unstim. Control B cells |
| BCL2L1 |

*(>2 fold);
IFN signature genes are in bold

TLR 9 Signals Induce ARID3a and IFN-Alpha Expression in Healthy Control B Cells

The initiating signals that induce ARID3a expression in SLE B cells are unknown. Although multiple stimuli induce ARID3a expression in mouse B cells, induction of ARID3a in healthy human B lymphocytes has been difficult. Viral pathogens, microbial products, and self-antigens trigger innate immune responses in cell types expressing endosomal TLRs, including B cells, leading to the production of IFN-alpha. The inventors hypothesized that ARID3a expression would be induced by stimuli that lead to IFN-alpha expression (i.e., microbial products or self-antigens). Therefore, a variety of TLR and NOD-like receptor agonists were assessed for their ability to induce ARID3a expression in B lymphocytes from healthy donors. Although expression of ARID3a was modestly stimulated by several of these agonists, stimulation of TLR 9 led to robust increases (p=0.0015) in numbers of ARID3a$^+$ B cells (FIG. 3A). Therefore, the effects of increasing concentrations of CpG on ARID3a and IFN-alpha expression were further evaluated in healthy B cells from 3 donors after 24 hours. Representative percentages of IFN-alpha$^+$ ARID3a$^+$ B cells induced by CpG stimulation versus media control are shown in FIG. 3B. These data indicate that ARID3a expression is robustly stimulated through activation of TLR 9 in healthy control B cells, and titrates with expression of IFN-alpha.

Figure 3C:
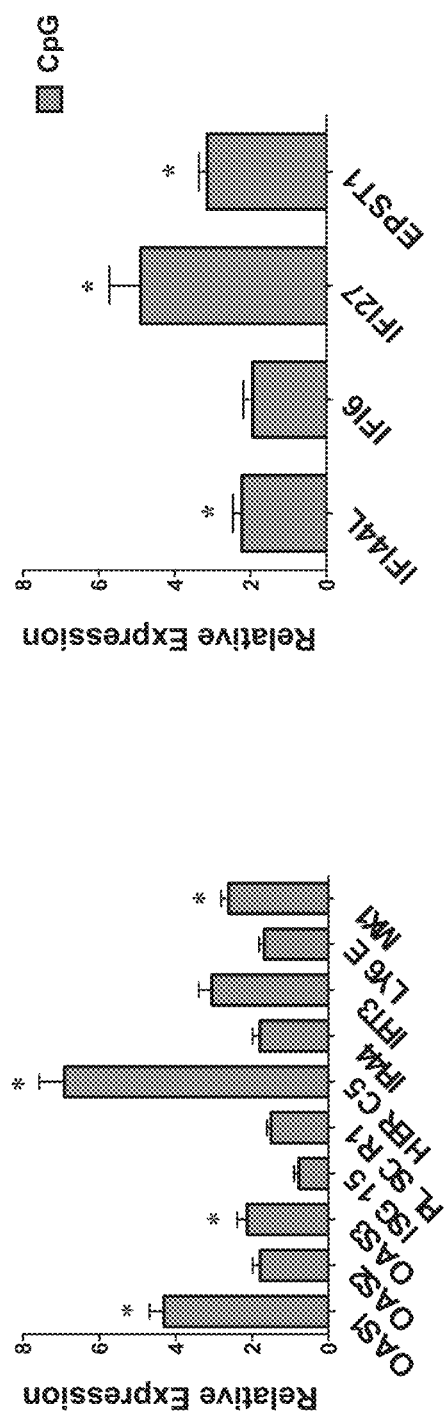
FIG. 3C is a Biomark HD qRT-PCR analysis demonstrating IFN-alpha signatures in FACs-purified CD20$^+$ B cells from CpG-treated (n=2) and unstimulated (n=2) healthy control samples.
Figure 3D:
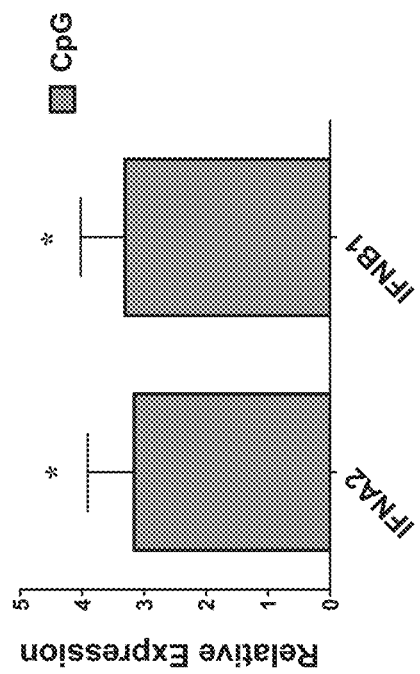
FIG. 3D is a Biomark HD qRT-PCR analysis demonstrating TLR pathway-associated genes in FACs-purified CD20$^+$ B cells from CpG-treated (n=2) and unstimulated (n=2) healthy control samples.
Figure 3D:
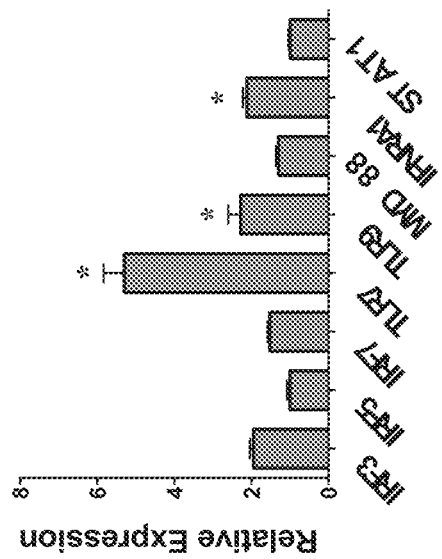

ARID3a$^+$ healthy B cells were further evaluated for expression of IFN-alpha signature genes, as performed above for SLE ARID3a$^H$ and ARID3a$^N$ B cells, by BioMark HD qRT-PCR. CpG-stimulated healthy B cells showed increased expression of many of the same IFN-alpha signature genes associated with ARID3a expression in SLE B cells (FIG. 3C, Tables 2 and 3). CpG-stimulated B cells showed increased expression of several IFN signature genes in comparison to control B cells, including IFNA2 and IFNB1 (see Table 4, FIGS. 3C-D). In line with previous studies, several IFN-alpha signature genes were highly expressed in SLE versus healthy control B cells (Tables 2 and 4). Furthermore, comparison of upregulated genes from CpG-stimulated B cells and ARID3a$^H$ SLE B cells showed up regulation of TLR7, as well as 7 IFN-alpha signature genes, in both array sets (Table 2). Interestingly, expression of BCL2L1 was increased in ARID3a$^H$ SLE B cells, but downregulated in healthy control B cells upon stimulation with CpG (Tables 2 and 4). While most genes analyzed were similarly regulated in SLE ARID3a$^+$ versus healthy CpG-stimulated B cells, these data indicate that ARID3a$^+$ SLE B cells may differ from healthy ARID3a⁺ B cells and may become dysregulated in healthy versus SLE inflammatory responses.

TABLE 4

Upregulated* or downregulated* genes in CpG-stimulated Versus unstimulated healthy control B cells

| Gene | P-value |
|---|---|
| Upregulated | |
| EPST1 | 1.5141E−07 |
| HERC5 | 3.2523E−07 |
| IFI44L | 1.2634E−03 |
| IFIT3 | 1.2119E−04 |
| MX1 | 2.0624E−06 |
| Ly6E | 2.6060E−04 |
| OAS1 | 3.8393E−07 |
| OAS3 | 1.3798E−03 |
| PLSCR1 | 3.3164E−04 |
| IFNA2 | 1.5070E−02 |
| IFNRA1 | 5.7879E−08 |
| IFNB1 | 1.7893E−02 |
| TLR7 | 1.6453E−06 |
| TLR9 | 1.5184E−03 |
| Downregulated | |
| BCL2L1 | 9.4228E−03 |

*Upregulated or downregulated >2 fold;
IFN signature genes are in bold

IFN-Alpha is Secreted from SLE B Cells

Figure 4A:
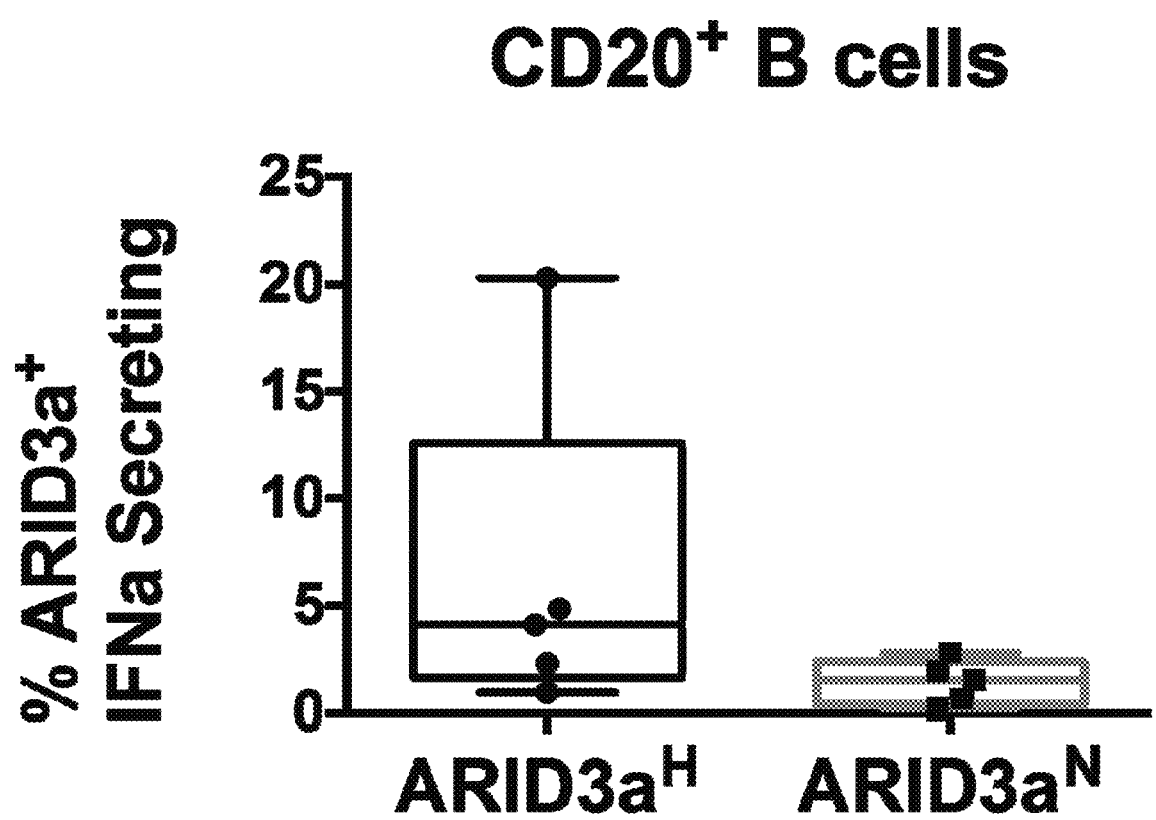
FIG. 4A shows the results of flow cytometry demonstrating through percentages of ARID3a+ IFN-alpha-secreting B cells in ARID3a$^H$ (n=4) and ARID3a$^N$ (n=5) SLE patient samples that ARID3a+SLE B cells secrete IFN-alpha.
Figure 4B:
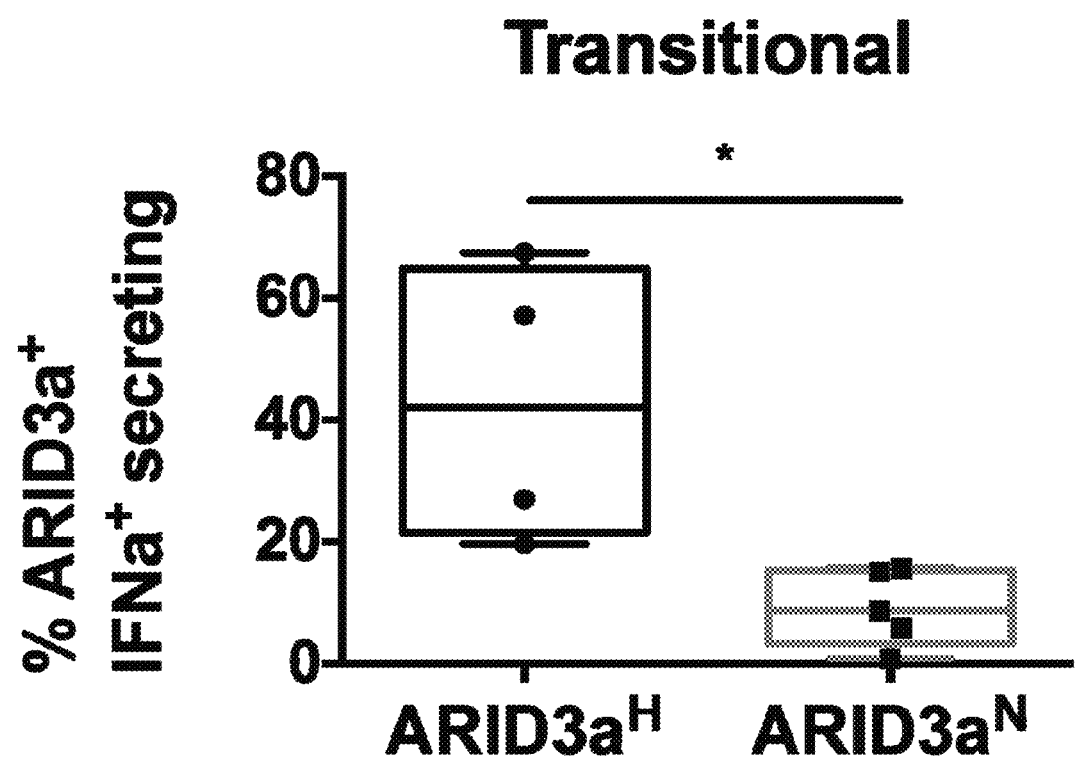
FIG. 4B shows the percentages of ARID3a+IFN-alpha-secreting B cells in transitional (IgD$^+$CD27$^-$CD10$^+$) B cell subsets.
Figure 4C:
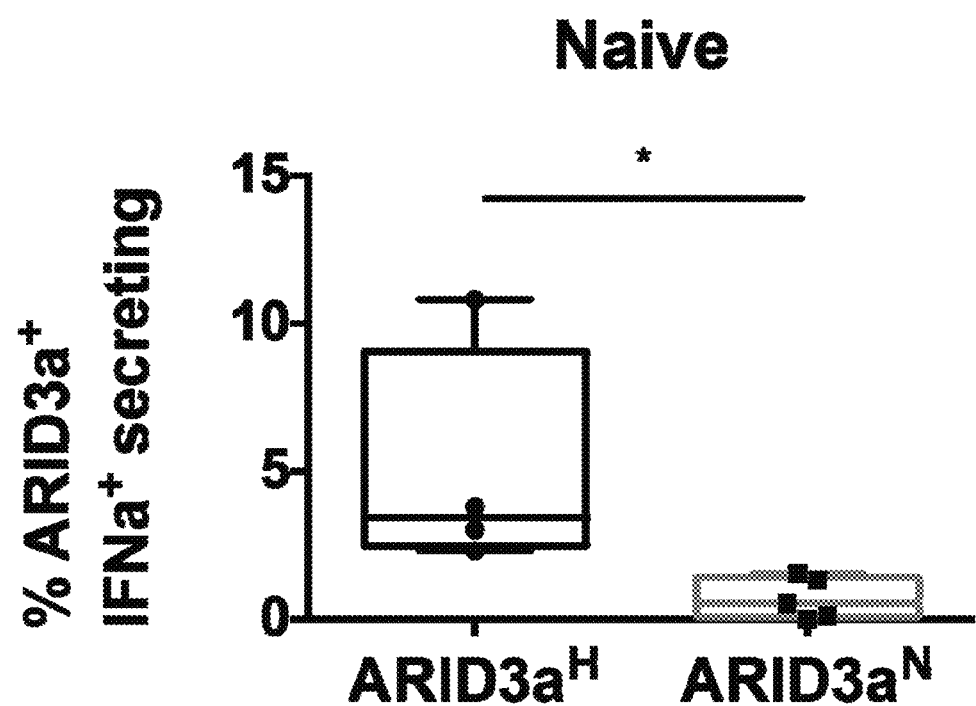
FIG. 4C shows the percentages of ARID3a+IFN-alpha-secreting B cells in naïve (IgD$^+$CD27$^-$CD10$^-$) B cell subsets.
Figure 4D:
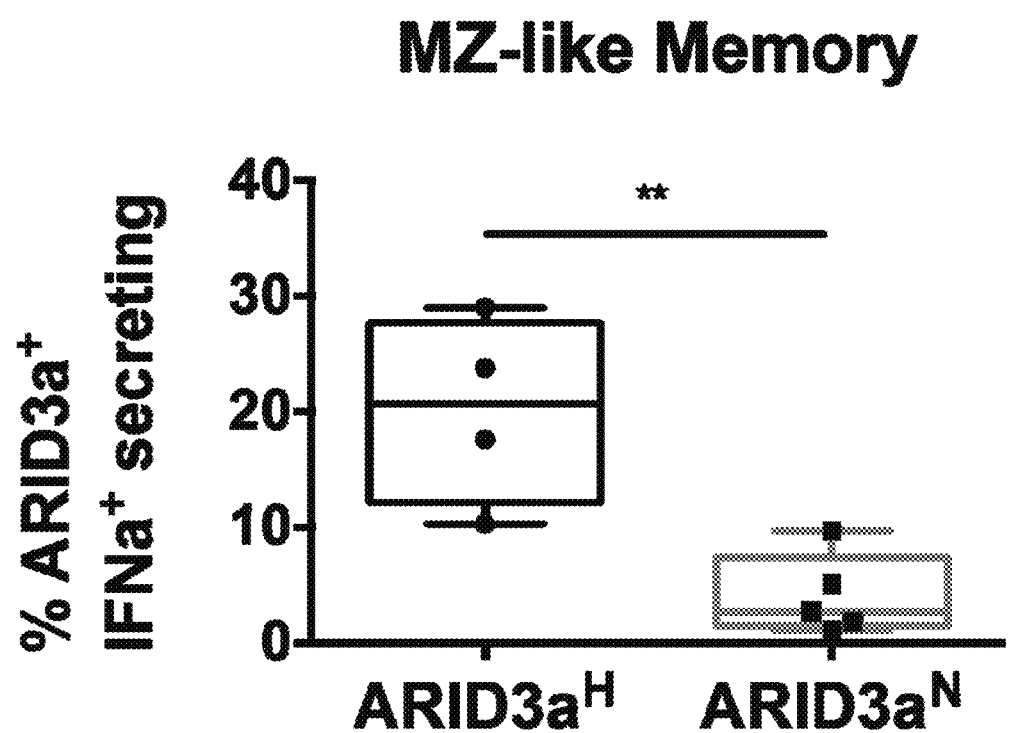
FIG. 4D shows the percentages of ARID3a+IFN-alpha-secreting B cells in MZ-like memory (IgD$^+$CD27$^+$) B cell subsets.
Figure 4E:
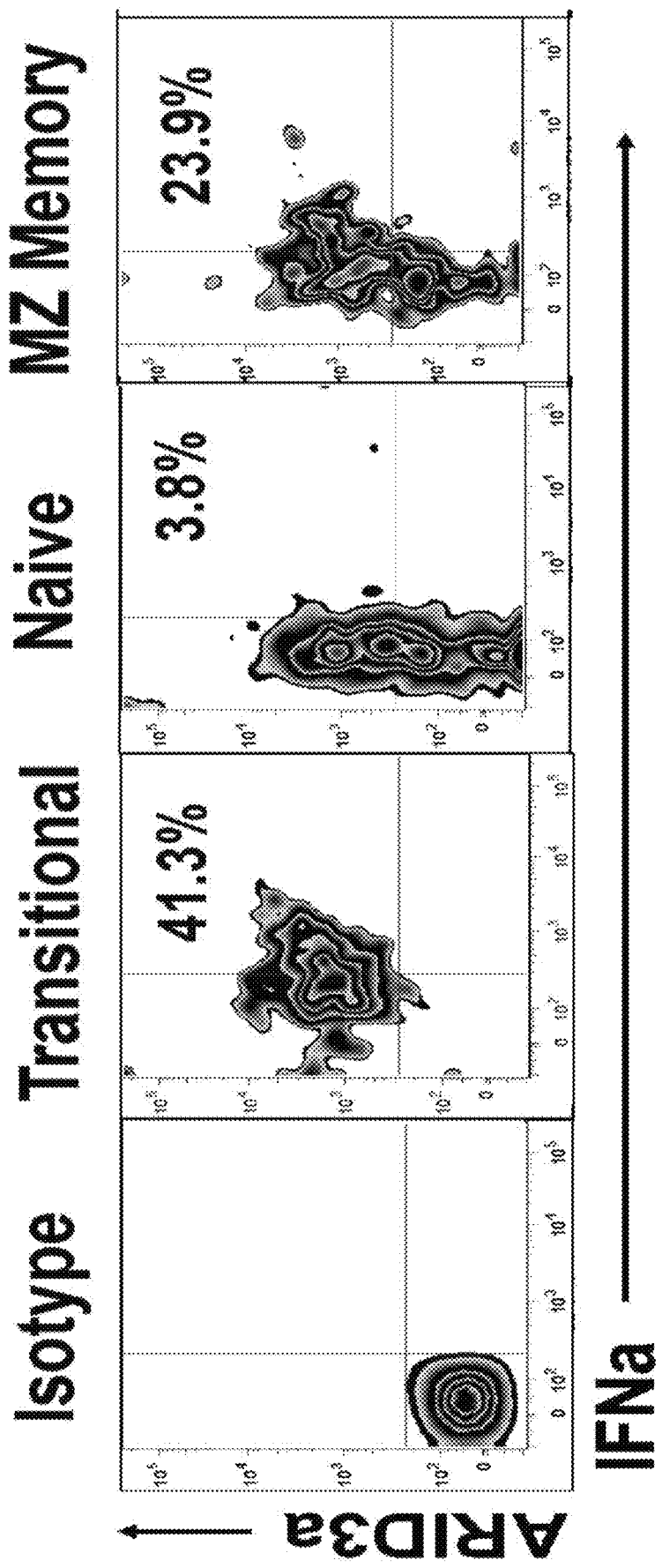
FIG. 4E shows representative flow plots from one ARID3a[H] individual showing percentages of ARID3a+ IFN-alpha-secreting cells in multiple subsets.

Although the data provided herein demonstrated IFN protein expression in ARID3a⁺ B cells, it was also determined if IFN-alpha was secreted from SLE B cells. Using an IFN-alpha capture antibody, it was found that both ARID3a$^H$ and ARID3a$^N$ B cell samples showed evidence of IFN-alpha secretion (FIG. 4A). Examination of individual B cell subsets indicated that ARID3a$^H$ B cell samples had significantly higher percentages of ARID3a⁺ IFN-alpha-secreting cells in transitional (p=0.0159), naïve (p=0.0159), and MZ memory (p=0.0047) B cells, versus ARID3a$^N$ samples (FIGS. 4B-D). A representative flow plot for an ARID3a$^H$ B cell sample, showing percentages of ARID3a⁺ IFN-alpha-secreting naïve, MZ-like memory, and transitional B cells, is presented in FIG. 4E. These data indicate that SLE ARID3a⁺ B cells can secrete IFN-alpha at multiple stages of differentiation, including the early transitional B cell stage.

ARID3a⁺ Healthy B Lymphocytes Act as Effector B Cells

Figure 5A:
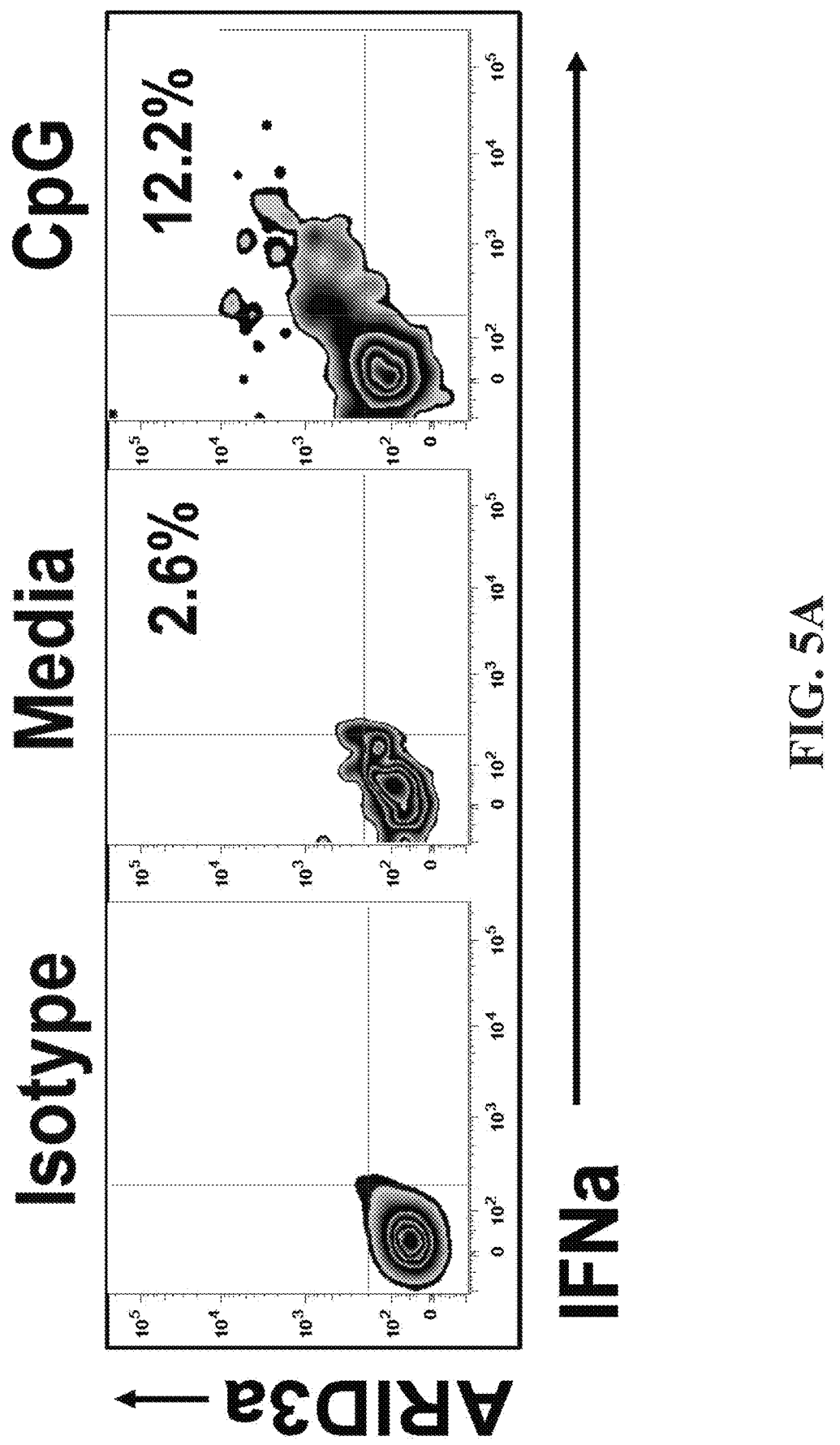
FIG. 5A demonstrates that healthy donor ARID3a+ B cells secrete IFN-alpha analyzed by flow cytometry for percentages of ARID3a+ IFN-alpha-secreting total B cells with and without CpG stimulation (n=6). Means, standard errors, and significance (paired Student's T test, **p<0.01) are shown.
Figure 5B:
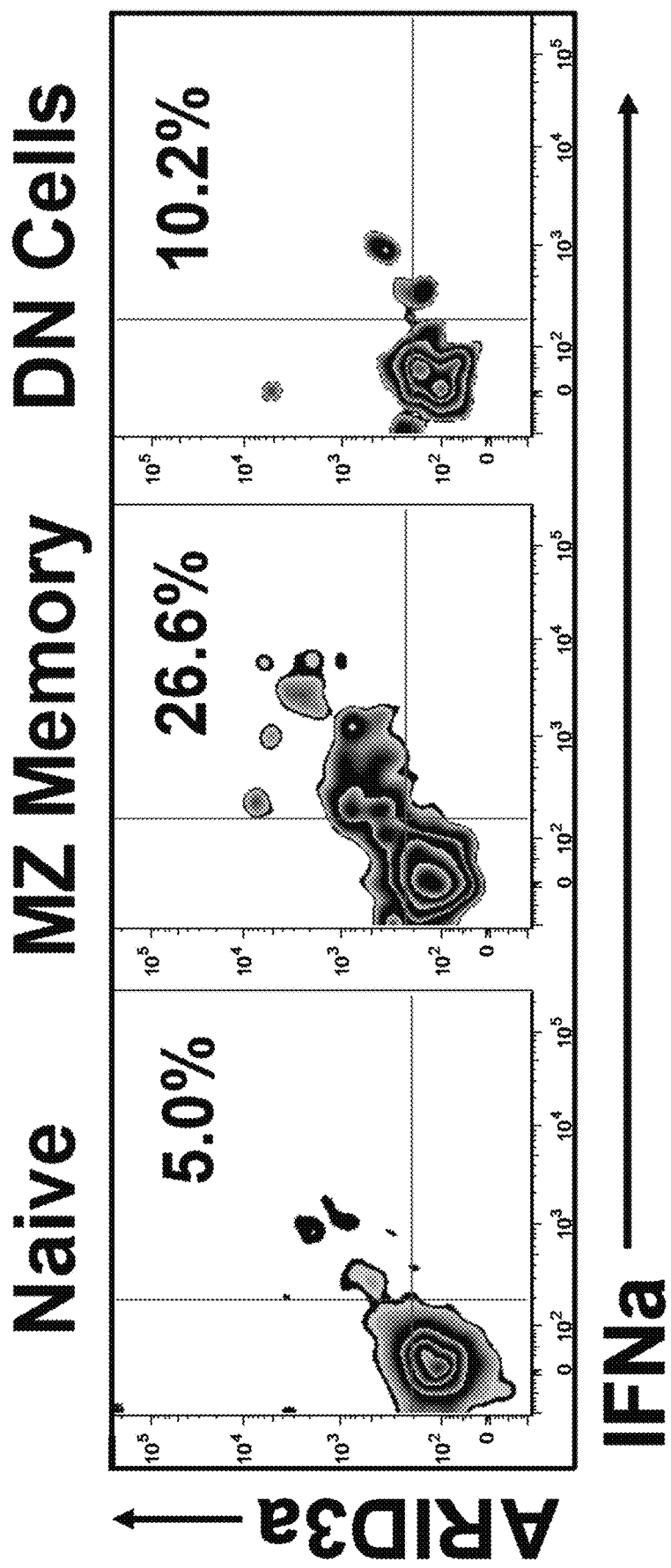
FIG. 5B demonstrates that healthy donor ARID3a+ B cells secrete IFN-alpha in individual naïve (IgD+CD27−CD10−), MZ memory (IgD+CD27+), and DN (IgD−CD27−) B cell subsets. Means, standard errors, and significance (paired Student's T test, **p<0.01) are shown.

To determine if IFN-alpha secretion is a property of healthy ARID3a⁺ B cells, healthy donor cells were stimulated with CpG (3 µg/ml) and assessed for secreted IFN-alpha as described above. Healthy ARID3a⁺ B cells also secreted IFN-alpha (FIG. 5A). However, consistent with the inventors' previous findings that healthy naïve B cells do not typically express ARID3a, even after CpG stimulation, there was little IFN-alpha secretion from those cells, or from the more mature DN subset. Interestingly, healthy MZ-like ARID3a⁺ B cells showed robust IFN-alpha secretion (FIG. 5B). These data indicate that healthy MZ-like ARID3a⁺ B cells secrete IFN-alpha.

Figure 5C:
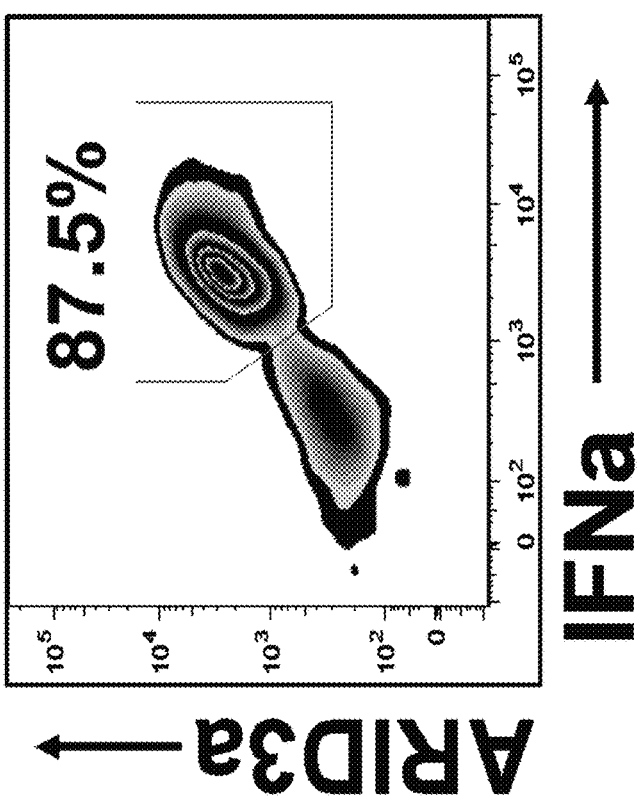
FIG. 5C demonstrates that healthy donor ARID3a+ B cells secrete IFN-alpha and act as effector cells. Representative autologous pDCs cocultured with CpG-stimulated or unstimulated B cells were evaluated by flow cytometry for ARID3a and IFN-alpha expression (n=6). Means, standard errors, and significance (paired Student's T test, **p<0.01) are shown.
Figure 5C:
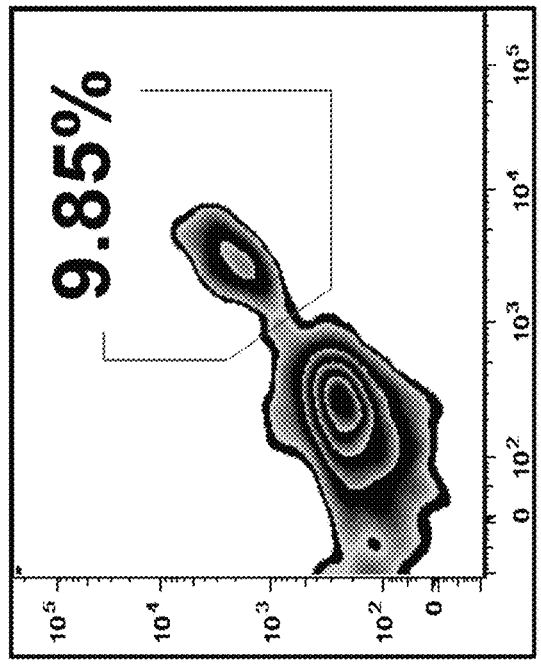
Figure 5D:
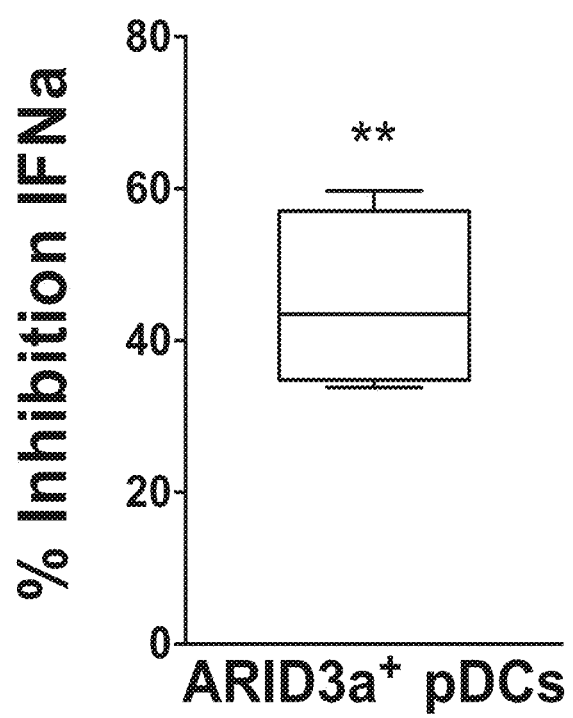
FIG. 5D demonstrates that healthy donor ARID3a+ B cells secreting IFN-alpha and acting as effector cells can be inhibited by an IFN-alpha blocking antibody. The percent inhibition of IFN-alpha expression by the blocking antibody was determined in ARID3a+ pDCs by flow cytometry. Means, standard errors, and significance (paired Student's T test, **p<0.01) are shown.
Figure 6A:
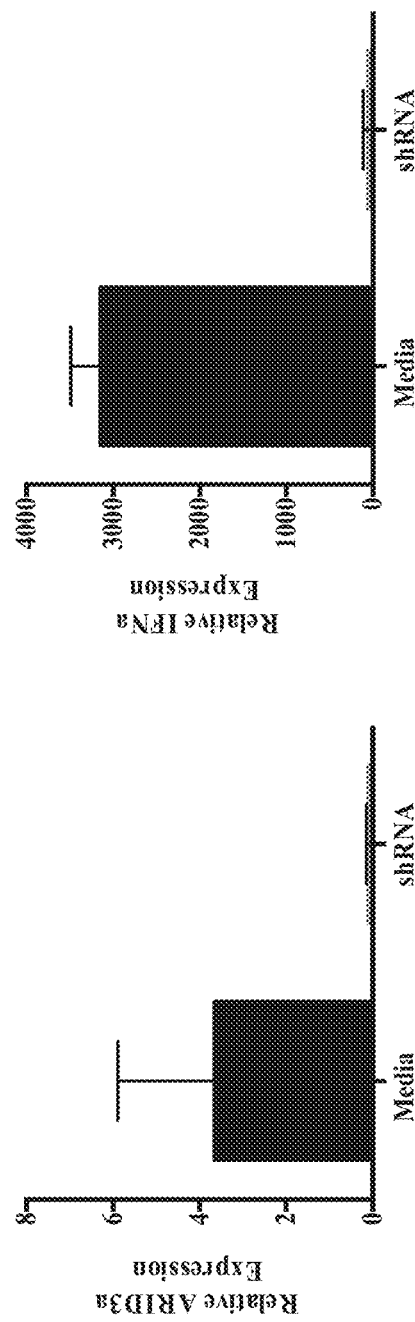
FIG. 6A shows knockdown of ARID3a resulted in knockdown of IFN-alpha inhibition when EBV lymphoblastoid cells were infected with ARID3a shRNA-expressing lentivirus (moi 3) and qRT-PCR was performed for ARID3a and IFNA after 36 hours on ARID3a-inhibited and untreated cells. Duplicate wells (40,000 cells/well) were evaluated in triplicate. Average and standard errors are shown.
Figure 6B:
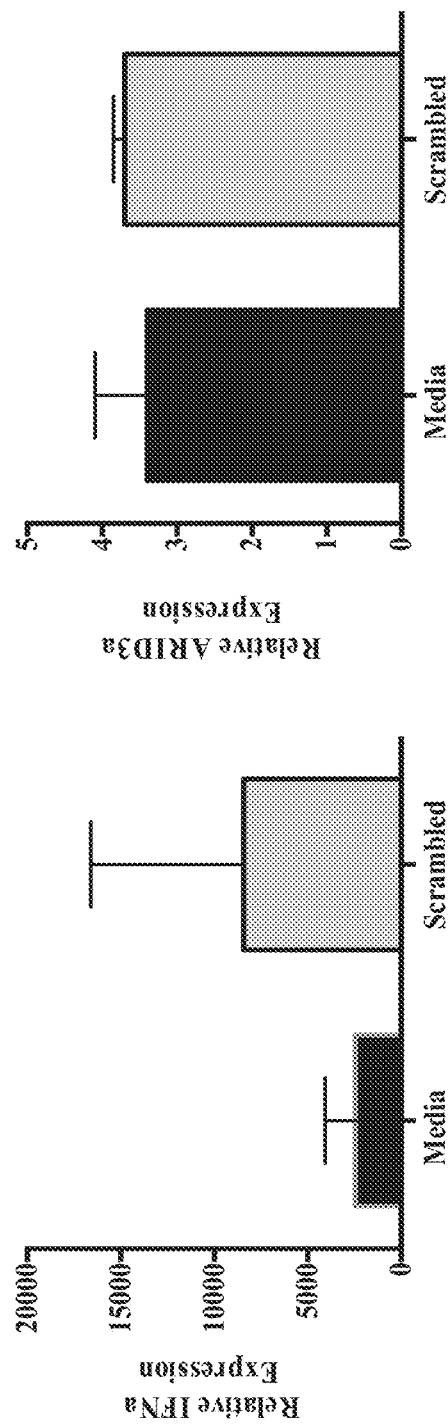
FIG. 6B shows EBV lymphoblastoid cells treated with scrambled control shRNA vectors, and qRT-PCR was performed for ARID3a and IFNA after 36 hours on ARID3a-inhibited and untreated cells. Duplicate wells (40,000 cells/well) were evaluated in triplicate. Average and standard errors are shown.

The inventors found it unlikely that secretion of IFN-alpha from B lymphocytes could account for the association between ARID3a expression and IFN-alpha plasma levels (FIG. 1B). Plasmacytoid dendritic cells (pDCs) are the most notable human IFN-alpha producers, secreting 10-100× more IFN-alpha than other cell type upon activation. Because IFN-alpha can act as an autocrine factor to induce additional IFN-alpha secretion, the inventors hypothesized that ARID3a⁺ IFN-alpha-secreting B cells were effector cells that would stimulate increased IFN-alpha production in pDCs. Therefore, healthy control (n=6) CpG-stimulated or unstimulated B cells were cultured with autologous pDCs (3:1) for 20 hours prior to assessment of intracellular ARID3a and IFN-alpha expression in gated pDCs. Interestingly, IFN-alpha⁺ pDCs also expressed ARID3a when cocultured with CpG-treated control B cells, which stimulated (p=0.0409) a 3.49 fold increase in IFN-alpha⁺ ARID3a⁺ pDCs relative to unstimulated B cells on average (range 1.34-8.84). The most dramatic increase in IFN-alpha⁺ ARID3a⁺ pDCs was approximately 9-fold (87.5%), versus coculture with unstimulated B cells (9.85%) (FIG. 5C). Stimulation of pDCs with CpG alone did not induce ARID3a or IFN-alpha expression under these conditions (not shown). Further, addition of polyclonal IFN-alpha blocking antibodies to pDC cocultures (n=4) with autologous CpG-stimulated B cells inhibited production of IFN-alpha⁺ ARID3a⁺ pDCs (p=0.0026) (FIG. 5D). Together these data indicate that ARID3a⁺ IFN-alpha-secreting B cells are innate effector B cells capable of secreting IFN-alpha and influencing IFN-alpha production in other cells.

In certain embodiments of this disclosure, the results show that expanded numbers of ARID3a⁺ B cells in SLE are associated with increased plasma levels of IFN-alpha and that both healthy and SLE B cells that express ARID3a synthesize IFN-alpha. Additionally, these healthy ARID3a⁺ B cells can act as effector cells to enhance IFN-alpha secretion in pDCs. Together, these data indicate that ARID3a expression in B lymphocytes, and other cell types, including pDCs, is associated with IFN-alpha production. Thus, in at least one embodiment, the present disclosure identifies ARID3a as a marker for a new type of IFN-alpha-secreting effector B lymphocyte that is enriched in SLE patient samples.

Example 2: Inhibitors of ARID3a and Methods of Use

Morpholino Oligomer Inhibitors of ARID3a

Because the expression of ARID3a in B lymphocytes, pDCs, and other cell types correlates to IFN-alpha production and disease severity in SLE patients, inhibiting ARID3a can be a therapeutic method of treating SLE and other diseases and conditions associated with production or overexpression of IFN-alpha (such as described below). Certain embodiments of the present disclosure are therefore directed towards therapeutic treatment of inflammatory diseases through inhibiting ARID3a. In particular embodiments of the present disclosure, anti-ARID3a morpholino oligomers can be used in novel methods of ARID3a knockdown for causing reduced production of IFN-alpha in conditions and diseases associated with increased levels of IFN-alpha, including but not limited to, lupus erythematosus, systemic lupus erythematosus, rheumatoid arthritis, Sjogren's syndrome, and virally-induced conditions with inflammation due to increased levels of IFN-alpha including herpes viruses, Epstein Barr virus, mononucleosis, and varicella zoster.

For example, in at least certain embodiments of the present disclosure, antisense oligonucleotides, such as but not limited to morpholino oligomer sequences, can be constructed against all or subsequences of complementary base sequences (target regions) such as shown in Table 1 above. These antisense oligonucleotides can be used to knockdown ARID3a expression by targeting, binding to, and blocking processing of ARID3a precursor mRNA and/or translation of ARID3a mature mRNA.

As noted above, such morpholino oligomers can be attached to dendrimers such as (but not limited to) octa-guanadinium dendrimers forming "vivo-morpholinos" for enhancing cellular uptake. Two vivo-morpholinos constructs ("ATG" and "e515"- or "e5i5") were tested as inhibitors of mouse ARID3a in primary kidney organ culture. The morpholino oligomer ATG comprised the nucleobase sequence 5'-TCTCCATCACGGCCTGTAGTTTCAT-3' (SEQ ID NO:29) and the morpholino oligomer e515 comprised the nucleobase sequence 5'-CACAACCGTCCGCCACTCACTG-3' (SEQ ID NO:30). Results described below show that when ARID3a+ B cells were treated with morpholinos that target ARID3a RNA, there is a knockdown of ARID3a protein as well as a decrease in IFN-alpha protein expression.

Figure 7:
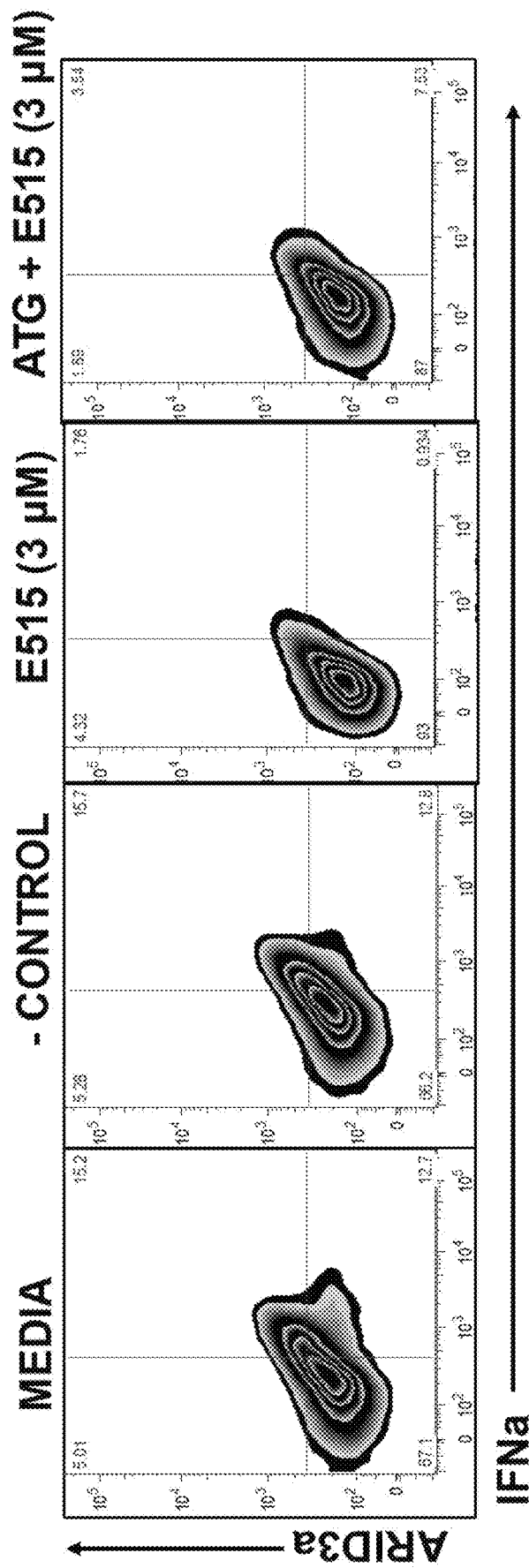
FIG. 7 shows that the knockdown of ARID3a protein corresponds to a decrease in IFN-alpha protein expression. Representative flow cytometry plots show percentages of both ARID3a and IFN-alpha in EBV-transformed B cells cultured in media alone or treated with negative control, morpholino antisense oligomer "e515" (also referred to herein as "e5i5"), or both e515 and morpholino antisense oligomer ATG for 24 hours.
Figure 8:
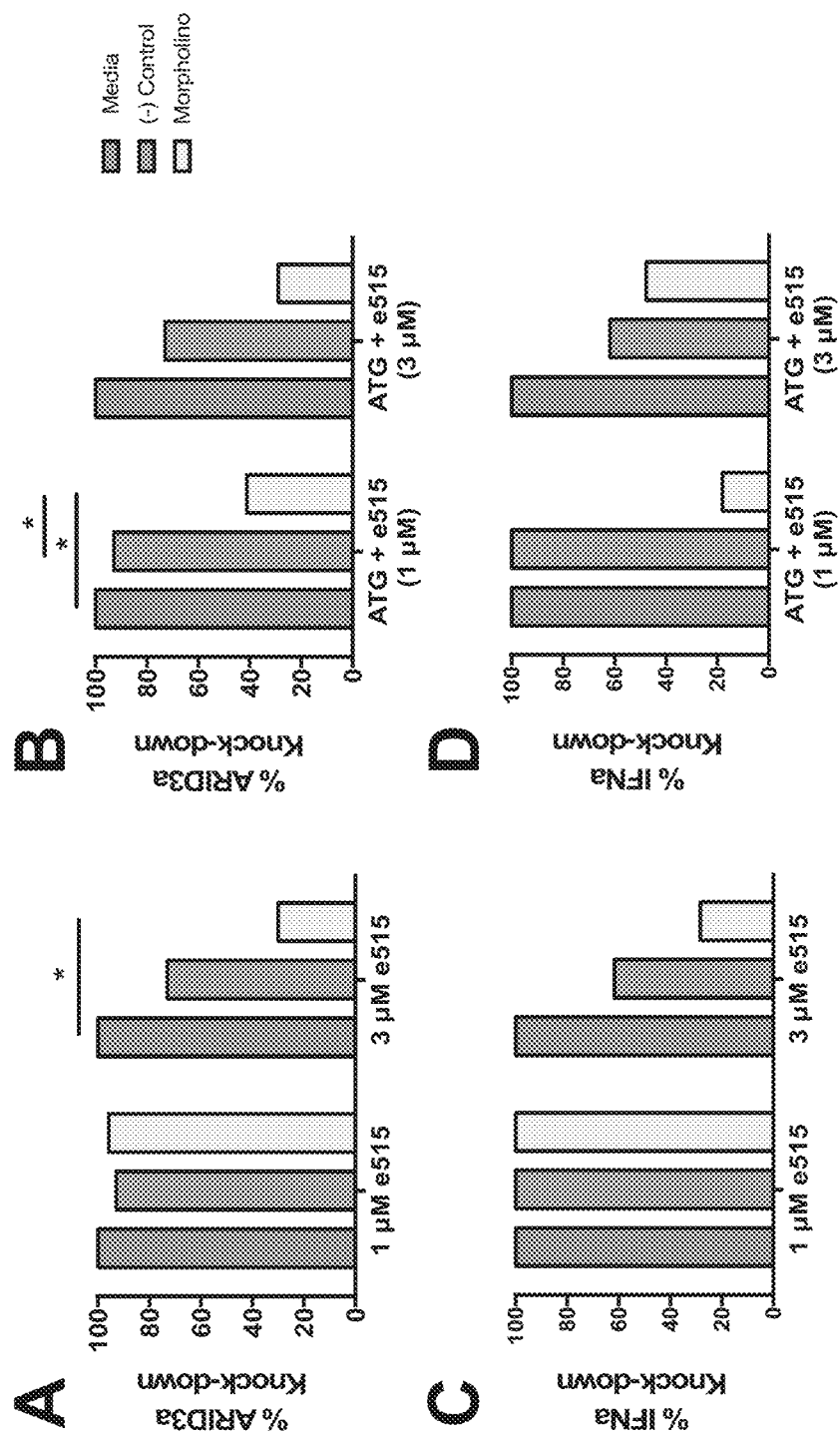
FIG. 8 is a flow cytometric analysis showing the percentage of ARID3a (A, B) or IFN-alpha (C, D) protein knockdown expression in EBV-transformed B cells in media alone, or after treatment with negative control morpholino, morpholino e515 (A, C), or morpholinos ATG+e515 (B, D) at 1 or 3 μM concentrations. Knockdown was calculated as a percentage of ARID3a or IFN-alpha positive cells in media alone.
Figure 9:
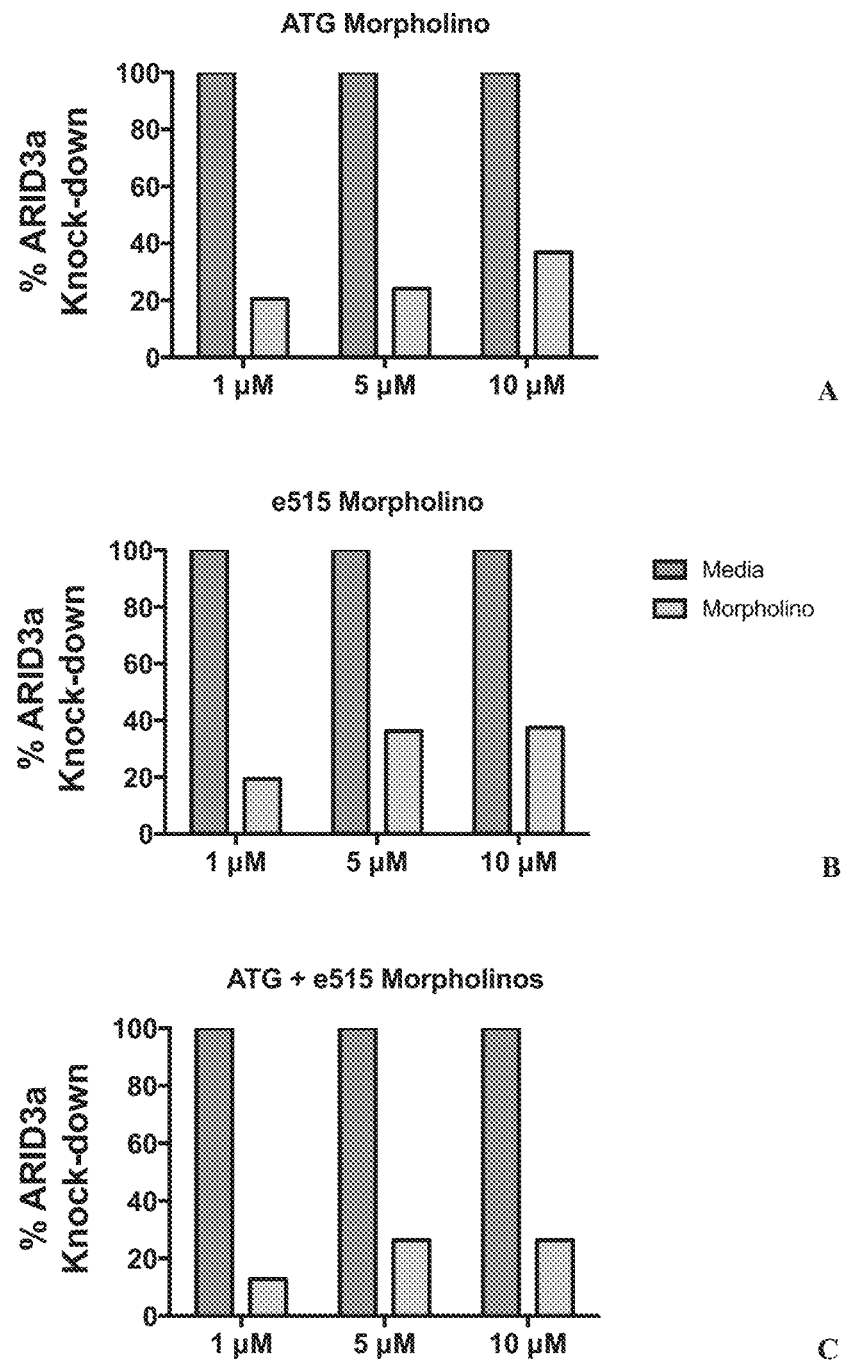
FIG. 9 shows that morpholino treatments cause knockdown of ARID3a protein expression in K562 cells. Flow cytometric analyses show the percentage of ARID3a protein knockdown expression in K562 cells in media alone or treatment with (A) ATG morpholino, (B) e515 morpholino, or (C) ATG+e515 morpholinos, at 1, 3, and 10 μM concentrations. Knockdown was calculated as a percentage of ARID3a+ cells in media alone.
Figure 10:
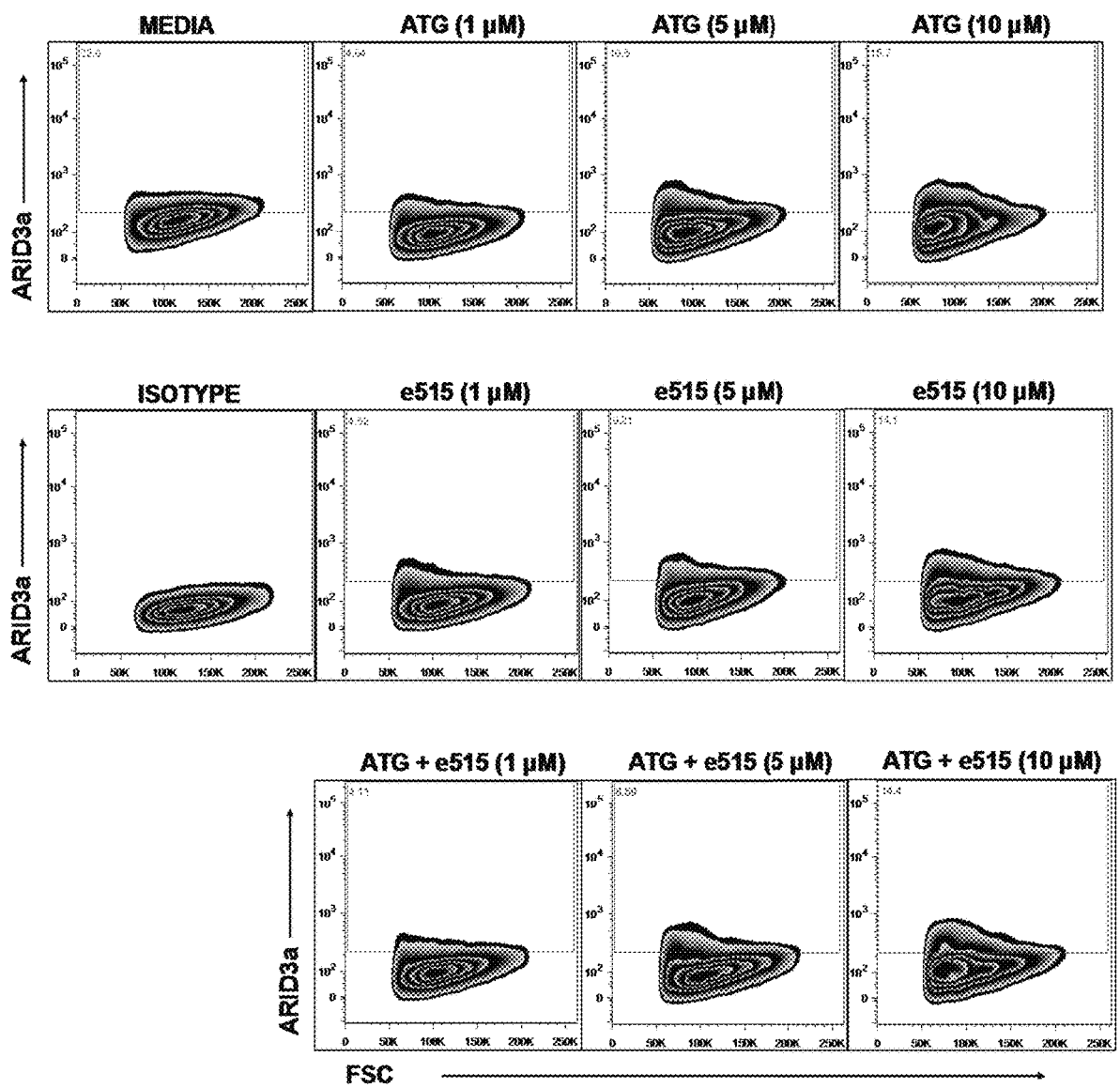
FIG. 10 is a representative flow cytometry plot showing percentages of ARID3a in the K562 cell line cultured in media alone or treated with negative control, e515, or both ATG+e515 morpholinos for 24 hours at varying doses.
Figure 11:
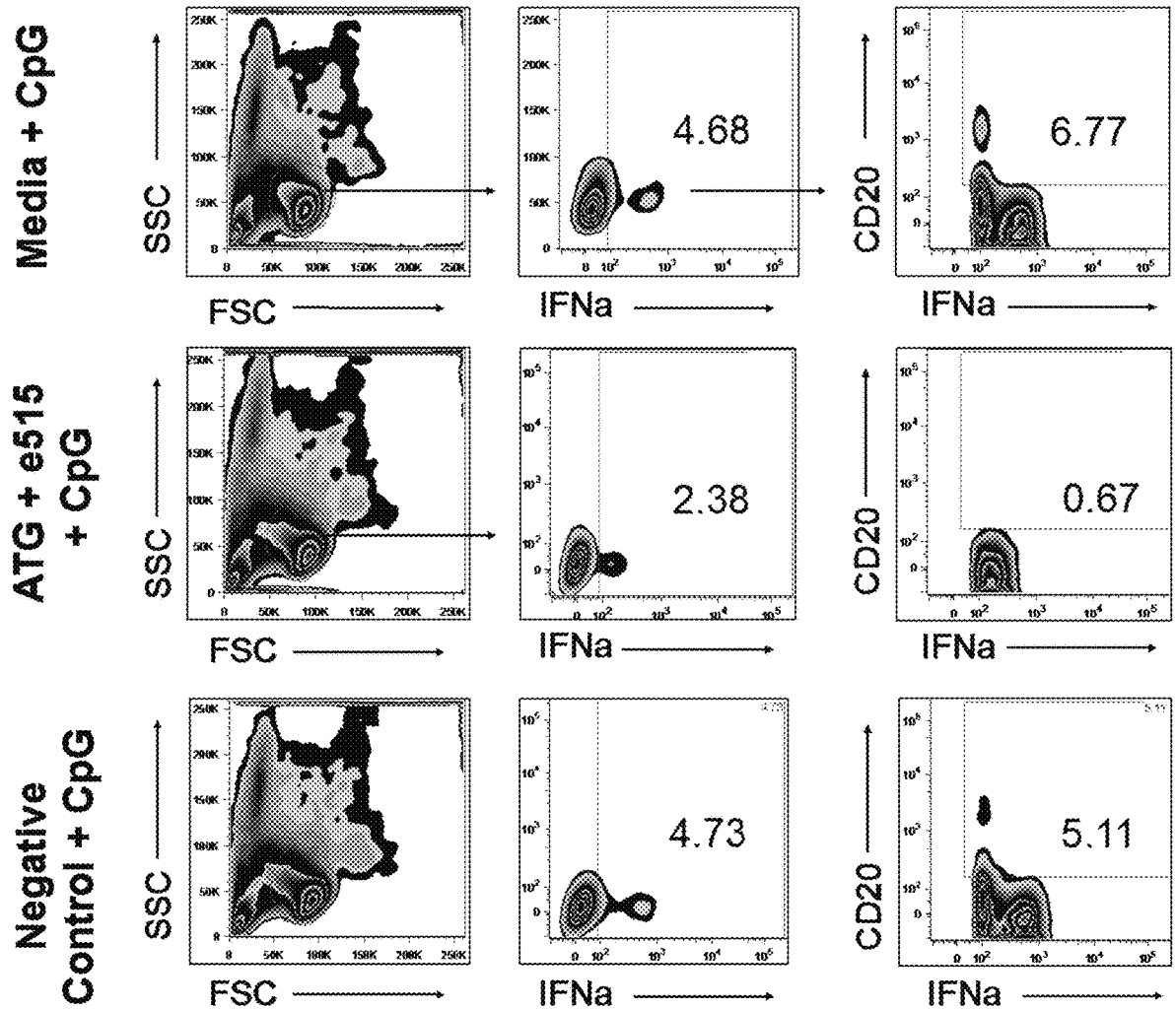
FIG. 11 is a representative flow cytometry plot showing percentages of IFN-alpha+ CD20+ B cells in healthy peripheral blood mononuclear cells (PBMCs) cultured in media with CpG (5 μM) stimulation alone, treatment with both ATG and e515 morpholinos (1 μM), or a negative control morpholino (1 μM) for 24 hours.
Figure 12:
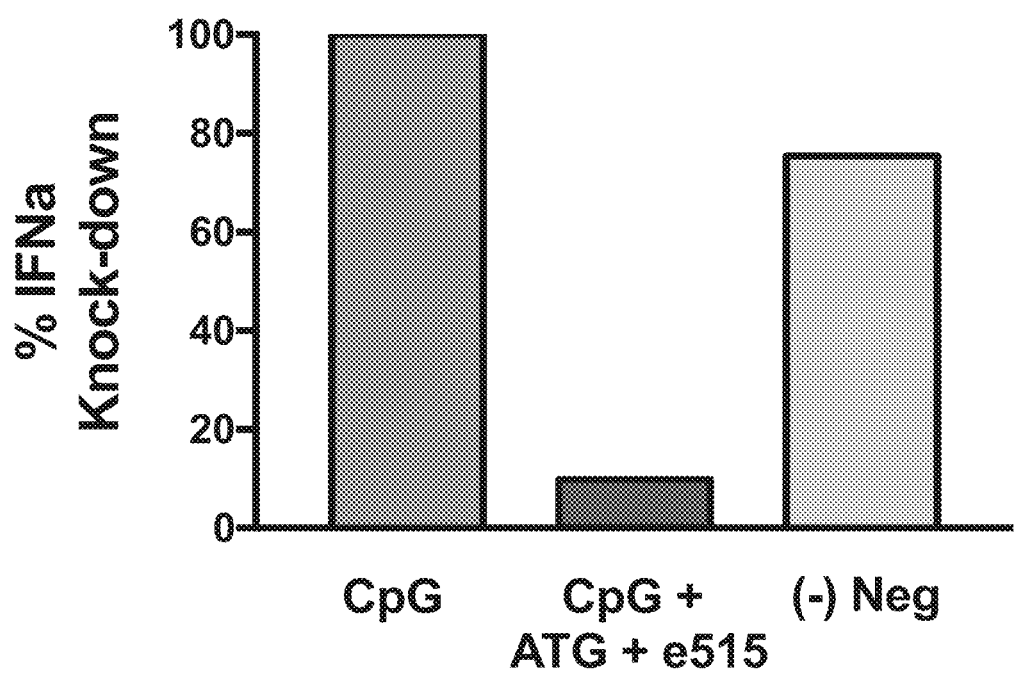
FIG. 12 is a flow cytometric analysis showing the percentage of IFN-alpha protein knockdown expression in CpG-stimulated (5 μM) healthy control PBMCs in media alone, treatment with both ATG and e515 morpholinos (1 μM), or a negative (−) control morpholino (1 μM) for 24 hours. Percent knockdown was calculated as a percentage of IFN-alpha+ cells with CpG-stimulation in media alone.
Figure 13:
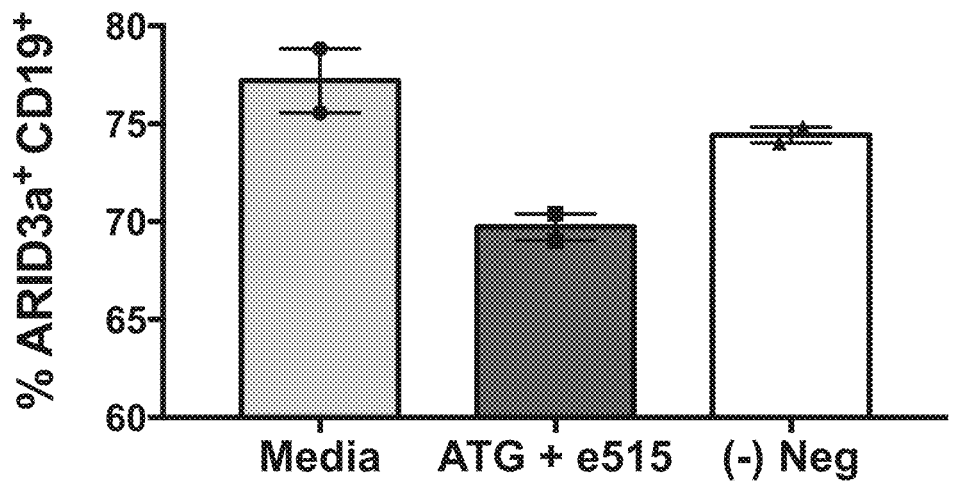
FIG. 13 is a flow cytometric analysis for the total percentage of (A) ARID3a+ or (B) IFN-alpha+ CD19+ B cells in ARID3a[H] SLE PBMCs cultured in media alone, treatment with both ATG and e515 morpholinos (3 μM), or a negative (−) control morpholino (3 μM) for 24 hours. Means and standard errors are shown.
Figure 13:
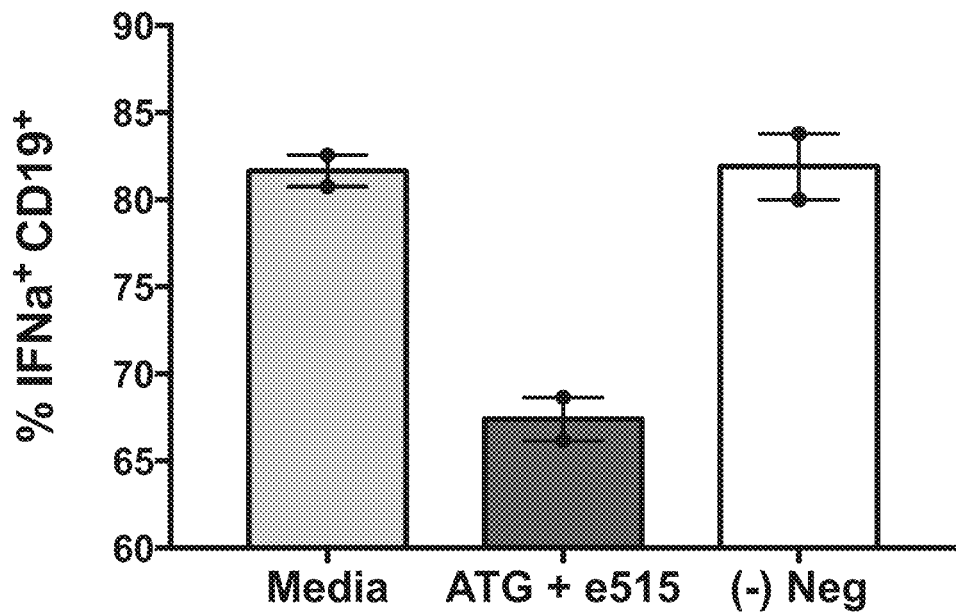
Figure 14:
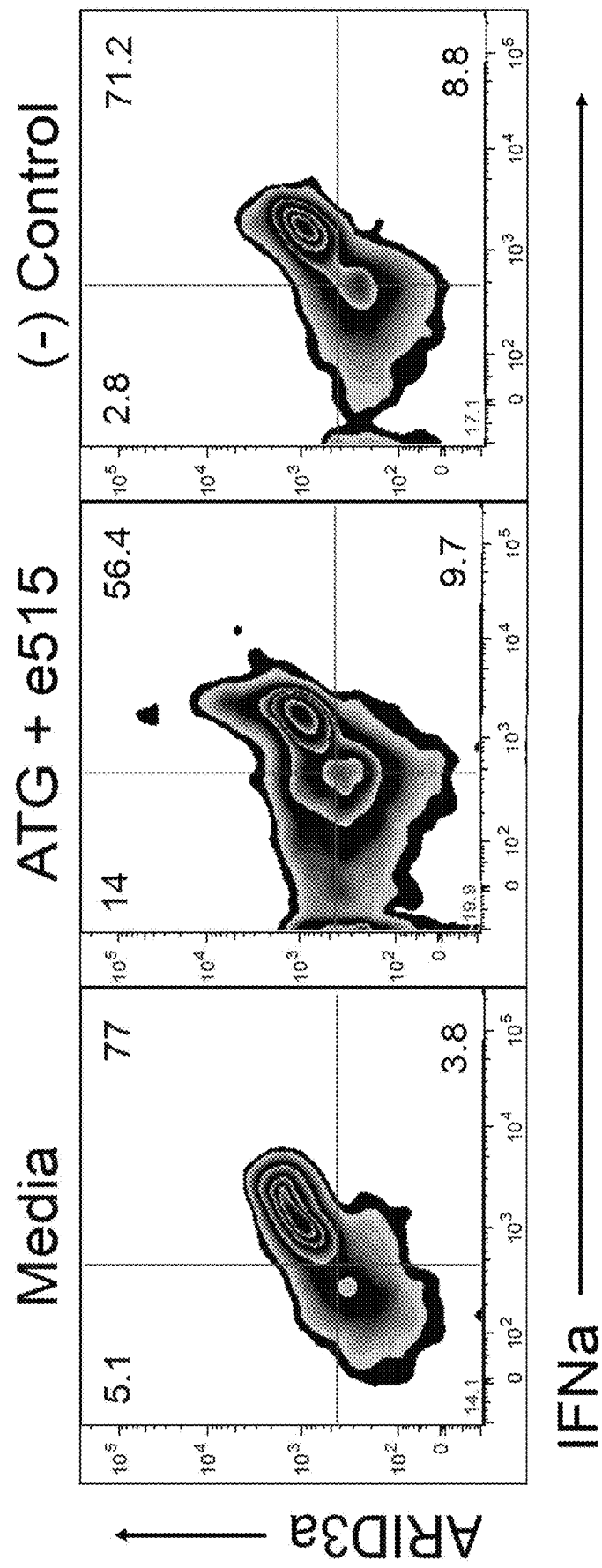
FIG. 14 is a representative flow cytometry plot showing percentages of both ARID3a and IFN-alpha expressing CD19+ B cells in peripheral blood mononuclear cells (PBMCs) cultured in media alone, treatment with both ATG and e515 morpholinos (3 μM), or a negative control morpholino (3 μM) for 24 hours.

As shown in FIG. 7, knockdown of ARID3a protein corresponds to a decrease in IFN-alpha protein expression, as demonstrated by representative flow cytometry plots showing percentages of both ARID3a and IFN-alpha in EBV-transformed B cells cultured in media alone or treated with negative control, morpholino e515, or both morpholinos ATG+e515 for 24 hours. FIG. 8 shows flow cytometric analyses showing the percentage of ARID3a (A,B) or IFN-alpha (C,D) protein knockdown expression in EBV-transformed B cells in media alone, or after treatment with negative control morpholino, morpholino e515 (A,C), or morpholinos ATG+e515 (B,D) at 1 or 3 μM concentrations. As shown in FIG. 9, anti-ARID3a morpholino treatments cause knockdown of ARID3a protein expression in K562 cells. Flow cytometric analyses showing the percentage of ARID3a protein knockdown expression in K562 cells in media alone or treatment with (A) morpholino ATG, (B) morpholino e515, or (C) morpholinos ATG+e515, at 1, 3, and 10 M concentrations. FIG. 10 shows representative flow cytometry plots showing percentages ARID3a in the K562 cell line cultured in media alone or treated with negative control, e515, or both ATG+e515 for 24 hours. FIG. 11 shows flow cytometry plots showing percentages of IFN-alpha$^+$CD20$^+$ B cells in peripheral blood mononuclear cells (PBMCs) cultured in media with CpG (5 μM) stimulation alone, treatment with both ATG and e515 (1 μM), or a negative control morpholino (1 μM) for 24 hours. FIG. 12 shows flow cytometric analyses showing the percentage of IFN-alpha protein knockdown expression in CpG-stimulated (5 μM) healthy control PBMCs in media alone, treatment with both ATG and e515 (1 μM), or a negative (−) control morpholino (1 μM) for 24 hours. FIG. 13 shows flow cytometric analyses for the total percentage of ARID3a$^+$ or IFN-alpha+ CD19$^+$ B cells in ARID3a$^H$ SLE PBMCs cultured in media alone, treatment with both ATG and e515 (3 μM), or a negative (−) control morpholino (3 μM) for 24 hours. FIG. 14 shows flow cytometry plots showing percentages of both ARID3a and IFN-alpha expressing CD19$^+$ B cells in peripheral blood mononuclear cells (PBMCs) cultured in media alone, treatment with both ATG and e515 (3 μM), or a negative control morpholino (3 μM) for 24 hours.

Figure 15:
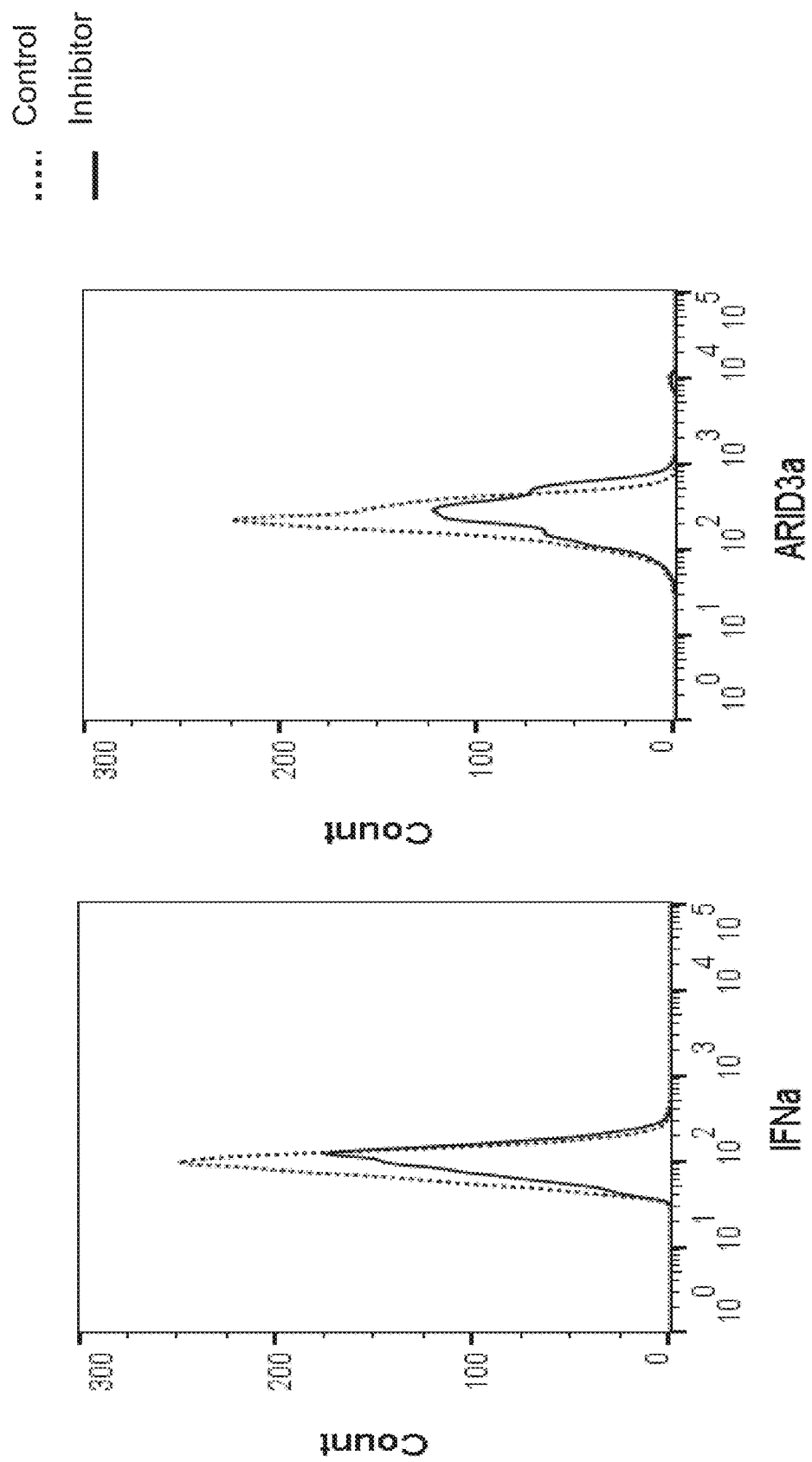
FIG. 15 shows that total numbers of interferon-expressing cells (IFNa) and ARID3a-expressing total PBMCs from an ARID3a[H] patient are reduced after only 24 hours of treatment with morpholinos ATG+e515 to inhibit ARID3a expression. Whole peripheral blood mononuclear cells from an SLE patient were depleted of erythrocytes via Ficoll gradient and cultured in a 24-well plate at 100,000 cells/well in 0.5 ml with a standard control morpholino (3 μM) or the two ARID3a-specific morpholinos (3 μM) for 24 hour prior to analyses by flow cytometry for total numbers of cells (Count on y axis) expressing intracellular ARID3a and IFNa.
Figure 16:
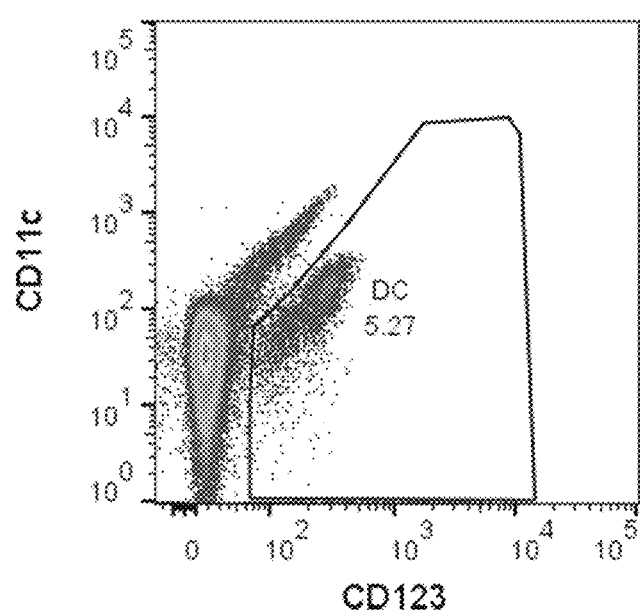
FIG. 16 shows gating of dendritic cells which express high levels of interferon in the experiment from FIG. 15. Whole peripheral blood mononuclear cells from an SLE patient were depleted of erythrocytes via Ficoll gradient and cultured in a 24-well plate at 100,000 cells/well in 0.5 ml with a standard control morpholino (3 μM) or a combination of ARID3a-specific morpholinos ATG+e515 (3 μM) for 24 hour and 48 hours prior to analyses by flow cytometry for numbers of cells expressing intracellular ARID3a and IFNa. Dendritic cells which express high levels of interferon that were gated by expression of CD11c and CD123.
Figure 17:
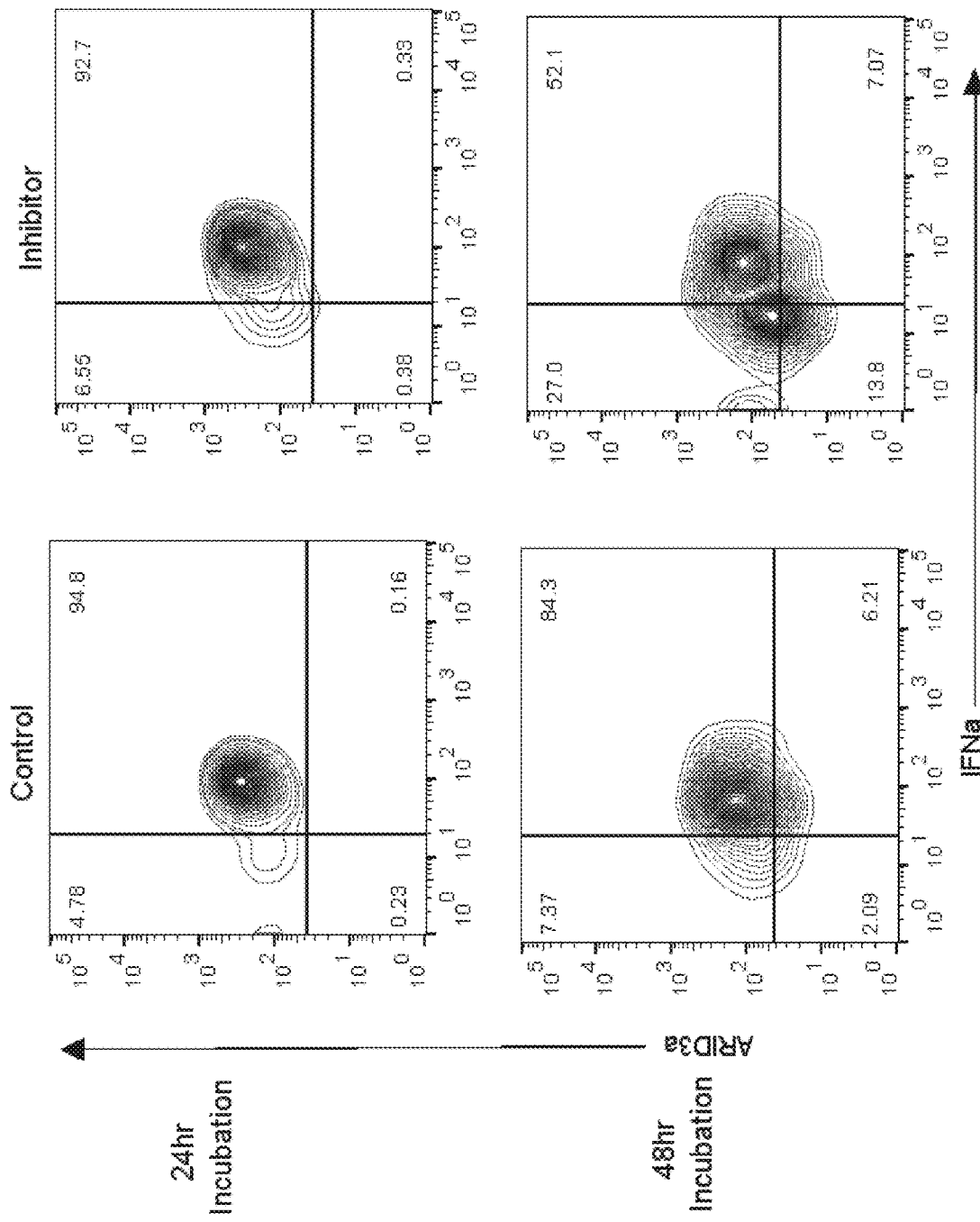
FIG. 17 shows analysis of the dendritic cells gated in FIG. 16. The gated dendritic cells were analyzed for ARID3a and IFNa. Percentages of positive and negative cells are shown in corners of each quadrant. Interferon protein expressing cells are reduced after 48 hours of ARID3a inhibition.

FIG. 15 shows that total numbers of IFNa-expressing cells and ARID3a-expressing cells were reduced after only 24 hours of treatment with morpholinos ATG+e515 to inhibit ARID3a expression. Whole peripheral blood mononuclear cells from an SLE patient were depleted of erythrocytes via Ficoll gradient and cultured in a 24-well plate at 100,000 cells/well in 0.5 ml with a standard control morpholino (3 μM) or the two ARID3a-specific morpholinos (3 μM) for 24 hour prior to analyses by flow cytometry for total numbers of cells (Count on y axis) expressing intracellular ARID3a and IFNa. FIG. 16 shows gating of dendritic cells which express high levels of interferon in the experiment shown in FIG. 15. Dendritic cells which express high levels of interferon are contained in the subpopulations expressing CD123 and having low to negative CD11c. FIG. 17 shows analysis of the dendritic cells gated in FIG. 16. The gated dendritic cells were analyzed for ARID3a and IFNa. Percentages of positive and negative cells are shown in the corners of each quadrant. Interferon protein expressing cells were reduced after 48 hours of ARID3a inhibition.

In at least certain embodiments, the present disclosure is directed to a method of characterizing the activity of SLE or other inflammatory-associated conditions in a subject by measuring the content of ARID3a. Measurement of ARID3a expressing cells or screening for upregulated ARID3a can therefore be used as a biomarker for patients undergoing inflammatory responses and/or disease flares. For example, to test for ARID3a and IFN-alpha, a combined screen with the following PCR primers could be used, followed by hybridization with probes recognizing both transcripts. ARID3a primers could include: exons 2-8 forward: 5'-AGCTGCAGCCGCCTGACCAC-3' (SEQ ID NO:31) and reverse: 5'-TGTTGGGAGCAGAGGTTGGC-3' (SEQ ID NO:32); and exons 4-7 forward: 5'-GTGGCGTGAGATCACCAAG-3' (SEQ ID NO:33) and reverse: 5'-CAGAACTCCTGTGTACATG-3' (SEQ ID NO:34). The IFN-alpha primers 5'-CCTGGCACAAATGAGGAGAA-3' (SEQ ID NO:35) and 5'-AGCTGCTGGTAAAGTTCAGTATAG-3' (SEQ ID NO:36), if used for qRT-PCR of SLE B cells, amplified about 70% of the IFN-alpha subtype genes.

In addition to their use in treating various inflammatory diseases related to IFN-alpha production as mentioned elsewhere herein, the antisense compounds of the present disclosure can be used as research reagents and diagnostics, and can be provided for example in kits. For example, the antisense compounds, by virtue of their ability to inhibit ARID3a expression and inhibit downstream production of IFN-alpha can be used to elucidate the function of particular ARID3a and IFN-alpha. The antisense compounds can be used, for example, to distinguish between functions of various components of a biological pathway and thus have use in research. The antisense compounds of the present disclosure, either alone or in combination with other antisense compounds or therapeutics, can be used as tools in differential and/or combinatorial analyses to elucidate expression patterns of distribution and activity of ARID3a and IFN-alpha in cells and tissues and as factors in various diseases and conditions. For example, expression patterns within cells or tissues treated with one or more antisense compounds disclosed herein can be compared to control cells or tissues not treated with the antisense compounds, and the patterns produced are analyzed for differential levels of gene expression as they pertain, for example, to disease association, signaling pathway, cellular localization, expression level, size, structure, or function of ARID3a and/or IFN-alpha. These analyses can be performed on stimulated or unstimulated cells and in the presence or absence of other compounds which affect expression patterns.

When employed as pharmaceuticals, the antisense oligonucleotides disclosed herein, for example as linked to cell penetrating moieties as described elsewhere herein, can be formulated with a pharmaceutically acceptable excipient or carrier to be formulated into a pharmaceutical composition. When employed as pharmaceuticals, the antisense compounds can be administered in the form of pharmaceutical compositions. These compounds can be administered by a variety of routes including, but not limited to, oral, rectal, transdermal, subcutaneous, intravenous, intramuscular, and intranasal. These compounds are effective as both injectable and oral compositions. Such compositions are prepared in a manner well known in the pharmaceutical art and comprise at least one antisense compound having anti-ARID3a activity. Examples of routes of administration of the active agents described herein include parenteral injection, e.g., by subcutaneous, intramuscular or transdermal delivery. Other forms of parenteral administration include intravenous, intraarterial, intralymphatic, intrathecal, intraocular, intracerebral, or intracavitary injection. In parenteral administration, the compositions will be formulated in a unit dosage injectable form such as (but not limited to) a solution, suspension, or emulsion, in association with a pharmaceutically acceptable excipient. Such excipients are inherently nontoxic and nontherapeutic. Examples of such excipients are saline, Ringer's solution, dextrose solution, and Hanks' solution. Nonaqueous excipients such as (but not limited to) fixed oils and ethyl oleate may also be used. An alternative excipient is 5% dextrose in saline. The excipient may contain minor amounts of additives such as (but not limited to) substances that enhance isotonicity and chemical stability, including buffers and preservatives.

The pharmaceutical compositions may comprise an antisense compound associated with one or more pharmaceutically acceptable excipients and/or carriers (i.e., diluents or vehicles). In making the compositions, the antisense compound is usually mixed with an excipient or carrier, diluted by an excipient or carrier, or enclosed within an excipient or carrier which can be in the form of a capsule, sachet, paper, or other container. When the excipient or carrier serves as a diluent, it can be a solid, semi-solid, or liquid material, which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as (but not limited to) talc, magnesium stearate, and mineral oil; wetting agents; emulsifying and suspending agents; preserving agents such as (but not limited to) methyl- and propylhydroxy-benzoates; sweetening agents; and flavoring agents. The compositions can be formulated so as to provide quick, sustained, or delayed release of the active ingredient after administration to the patient by employing procedures known in the art.

The antisense compounds are effective over a wide dosage range and are generally administered in a therapeutically-effective amount. It will be understood, however, that the amount of the antisense compound actually administered will be determined by a physician, in light of the relevant circumstances, including the condition to be treated, the chosen route of administration, the actual compound administered, the age, weight, and response of the individual patient, the severity of the patient's symptoms, and the like.

For preparing solid compositions such as (but not limited to) tablets or other solid dosage forms, the principal active ingredient can be mixed with a pharmaceutical excipient or carrier to form a solid preformulation composition containing a homogeneous mixture of the antisense compound. When referring to these preformulation compositions as homogeneous, it is meant that the active ingredient is dispersed evenly throughout the composition so that the composition may be readily subdivided into equally effective unit dosage forms such as tablets, pills, and capsules.

The dosage forms may be coated or otherwise compounded to provide a dosage form affording the advantage of prolonged action. For example, the tablet or pill can comprise an inner dosage component and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present disclosure may be incorporated for administration orally or by injection include (but are not limited to) aqueous solutions, suitably flavored syrups, aqueous or oil suspensions, and flavored emulsions with edible oils such as (but not limited to) corn oil, cottonseed oil, sesame oil, coconut oil, or peanut oil, as well as elixirs and similar pharmaceutical vehicles. In some embodiments, the antisense compound is administered in solution. The formulation thereof may be in a solution having a suitable pharmaceutically acceptable buffer such as (but not limited to) phosphate, Tris (hydroxymethyl) aminomethane-HCl or citrate, and the like. Buffer concentrations should be in the range of 1 to 100 mM. The formulated solution may also contain a salt, such as (but not limited to) sodium chloride or potassium chloride, in a concentration of 50 to 150 mM. An effective amount of a stabilizing agent such as (but not limited to) mannitol, trehalose, sorbitol, glycerol, albumin, a globulin, a detergent, a gelatin, a protamine, or a salt of protamine may also be included.

Compositions for inhalation or insufflation include solutions and suspensions in pharmaceutically acceptable, aqueous, or organic solvents, or mixtures thereof, and powders. The liquid or solid compositions may contain suitable pharmaceutically acceptable excipients as described supra. The compositions can be administered by the oral or nasal respiratory route for local or systemic effect. Compositions in pharmaceutically acceptable solvents may be nebulized by use of inert gases. Nebulized solutions may be inhaled directly from the nebulizing device, or the nebulizing device may be attached to a face mask tent or intermittent positive pressure breathing machine. Solution, suspension, or powder compositions may also be administered orally or nasally from devices which deliver the formulation in an appropriate manner.

The active agents of the present disclosure can be administered in the form of a liposome. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior. The aqueous portion contains the active agent to be delivered. In order to cross intact mammalian skin, lipid vesicles must pass through a series of fine pores, each with a diameter less than 50 nm, under the influence of a suitable transdermal gradient. Therefore, it is desirable in certain embodiments to use a liposome which is highly deformable and able to pass through such fine pores. Liposomes can be made from phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example (but not by way of limitation), soybean PC, and egg PC. Another type is formed from mixtures of phospholipid and/or phosphatidylcholine and/or cholesterol.

In certain embodiments, the compositions may be formulated in a unit dosage form, each dosage containing from about 5 mg to about 100 mg or more, such as (but not limited to) any of about 5 mg to about 10 mg, about 5 mg to about 20 mg, about 5 mg to about 30 mg, about 5 mg to about 40 mg, about 5 mg to about 50 mg, about 5 mg to about 60 mg, about 5 mg to about 70 mg, about 5 mg to about 80 mg, or about 5 mg to about 90 mg, inclusive, including any range in between these values, of the active ingredient, i.e., the antisense compound. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier. For example, but not by way of limitation, a therapeutically effective amount of an active agent used in the present disclosure will generally contain sufficient active agent to deliver in a range of from about 0.01 µg/kg to about 10 mg/kg (weight of active agent/body weight of patient). For example, but not by way of limitation, the composition will deliver about 0.1 µg/kg to about 5 mg/kg, and more particularly about 1 µg/kg to about 1 mg/kg.

Exemplary, non-limiting ranges for a therapeutically or prophylactically effective amount of the active agent (i.e., the antisense compound) also include but are not limited to 0.001 mg/kg of the subject's body weight to 100 mg/kg of the subject's body weight, more typically 0.01 mg/kg to 100 mg/kg, 0.1 mg/kg to 50 mg/kg, 0.1 mg/kg to 40 mg/kg, 1 mg/kg to 30 mg/kg, 1 mg/kg to 20 mg/kg, 2 mg/kg to 30 mg/kg, 2 mg/kg to 20 mg/kg, 2 mg/kg to 15 mg/kg, 2 mg/kg to 12 mg/kg, 2 mg/kg to 10 mg/kg, 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg, or 5 mg to 1500 mg, as a fixed dosage.

The composition is formulated to contain an effective amount of the active agent, wherein the amount depends on the animal to be treated and the condition to be treated. In certain embodiments, the active agent is administered at a dose ranging from about 0.001 mg to about 10 g, from about 0.01 mg to about 10 g, from about 0.1 mg to about 10 g, from about 1 mg to about 10 g, from about 1 mg to about 9 g, from about 1 mg to about 8 g, from about 1 mg to about 7 g, from about 1 mg to about 6 g, from about 1 mg to about 5 g, from about 10 mg to about 10 g, from about 50 mg to about 5 g, from about 50 mg to about 5 g, from about 50 mg to about 2 g, from about 0.05 µg to about 1.5 mg, from about 10 µg to about 1 mg, from about 30 µg to about 500 µg, from about 40 µg to about 300 µg, from about 0.1 µg to about 200 mg, from about 0.1 µg to about µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, or from about 1 mg to about 2 mg. The specific dosage level for any particular subject depends upon a variety of factors including the activity of the age, body weight, general health, sex, diet, time of administration, route of administration, and rate of excretion, drug combination, and the severity of the particular disease in the subject undergoing therapy.

The dosage of an administered active agent for humans will vary depending upon such factors as the patient's age, weight, height, sex, general medical condition and previous medical history. In certain non-limiting embodiments, the recipient is provided with a dosage of the active agent that is in the range of from about 1 mg to 1000 mg as a single infusion or single or multiple injections, although a lower or higher dosage also may be administered. The dosage may be in the range of from about 25 mg to 100 mg of the active agent per square meter ($m^2$) of body surface area for a typical adult, although a lower or higher dosage also may be administered. Examples of dosages that may be administered to a human subject further include, for example, 1 to 500 mg, 1 to 70 mg, or 1 to 20 mg, although higher or lower doses may be used. Dosages may be repeated as needed, for example, once per week for 4-10 weeks, or once per week for 8 weeks, or once per week for 4 weeks. It may also be given less frequently, such as (but not limited to) every other week for several months, or more frequently, such as (but not limited to) twice weekly or by continuous infusion.

The antisense compounds disclosed herein can be used for the treatment and/or prevention of symptoms of diseases and conditions associated with excessive IFN-alpha production, for example those associated with inflammatory responses. Such conditions and diseases are referred to as "interferonopathies." As demonstrated herein, IFN-alpha production characteristic of interferonopathies can be reduced, ameliorated, or inhibited by inhibiting ARID3a using the antisense compounds described herein. The antisense compounds can be used to treat SLE as well as other interferonopathies, including but not limited to lupus erythematosus, rheumatoid arthritis, and Sjogren's syndrome, Down Syndrome, and virally induced conditions with inflammation due to increased levels of IFN-alpha including herpes viruses, Epstein Barr virus, mononucleosis, and varicella zoster.

The embodiments of the present disclosure are directed to methods for inhibiting or reducing the symptoms or conditions (disabilities, impairments) associated with ARID3a expression such as IFN-alpha production as described in detail herein. As such, it is not required that all effects of the condition or disease be entirely prevented or reversed, although the effects of the presently disclosed methods likely extend to a significant therapeutic benefit for the patient. As such, a therapeutic benefit is not necessarily a complete prevention or cure for a particular condition or disease, but rather can encompass a result which includes reducing or preventing the symptoms that result from the condition, reducing or preventing the occurrence of such symptoms (either quantitatively or qualitatively), reducing the severity of such symptoms or physiological effects thereof, and/or enhancing the recovery of the individual after experiencing symptoms caused by the condition.

Provided in another aspect are methods for reducing the aggregation of one or more ARID3a mRNA transcripts within a cell. In some embodiments, the method reduces or prevents aggregation of one or more ARID3a mRNA transcripts in the nucleus of the cell. In some embodiments, the method prevents aggregation of one or more ARID3a proteins in the cell. In some embodiments, the method prevents aggregation of one or more IFN-alpha proteins in the cell.

Specifically, a composition of the present disclosure, when administered to an individual in need of such treatment, may treat, reduce, or prevent one or more of the symptoms or conditions associated with ARID3a and/or IFN-alpha production and/or reduce or alleviate symptoms of (or conditions associated with) this condition or disorder. As such, protecting an individual from the effects or symptoms resulting from a DM1 includes both preventing or reducing the occurrence and/or severity of the effects of the condition or disorder and treating a patient in which the effects of the condition or disorder are already occurring or beginning to occur. A beneficial effect can easily be assessed by one of ordinary skill in the art and/or by a trained clinician who is treating the patient. Preferably (but not by way of limitation), there is a positive or beneficial difference in the severity or occurrence of at least one clinical or biological score, value, or measure used to evaluate such patients in those who have been treated with the methods of the present disclosure as compared to those that have not.

It will be understood from the foregoing description that various modifications and changes may be made in the various embodiments of the present disclosure without departing from their true spirit. The description provided herein is intended for purposes of illustration only and is not intended to be construed in a limiting sense, except where specifically indicated. Thus, while the present disclosure has been described herein in connection with certain embodiments so that aspects thereof may be more fully understood and appreciated, it is not intended that the present disclosure be limited to these particular embodiments. On the contrary, it is intended that all alternatives, modifications, and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Changes may be made in the formulation of the various compounds and compositions described herein, the methods described herein, or in the steps or the sequence of steps of the methods described herein without departing from the spirit and scope of the present disclosure. All patents, published patent applications, and non-patent publications referenced in any portion of this application are herein expressly incorporated by reference in their entirety to the same extent as if each individual patent or publication was specifically and individually indicated to be incorporated by reference.

What is claimed is:

1. A method of inhibiting expression of interferon alpha in an individual having an interferon-alpha (IFN-alpha)-associated inflammatory disorder or condition, comprising:
    administering to a subject in need of such treatment an effective amount of an antisense compound which comprises an oligonucleotide consisting of 18-50 linked nucleosides, the oligonucleotide comprising a targeting sequence that is complementary and specifically hybridizable to a target sequence of an ARID3a nucleic acid selected from the group consisting of SEQ ID NOS:1-28, the target sequence comprising at least 18 contiguous nucleobases, and wherein the oligonucleotide is non-natural; and
    wherein the IFN-alpha-associated inflammatory disorder or condition is selected from the group consisting of lupus erythematosus, systemic lupus erythematosus, rheumatoid arthritis, Sjogren's syndrome, Down syndrome, and a virally-induced condition with inflammation due to increased levels of IFN-alpha associated with herpes viruses, Epstein Barr virus, mononucleosis, or varicella zoster.

2. The method of claim 1, wherein the oligonucleotide comprises at least one non-natural internucleoside linkage.

3. The method of claim 1, wherein the oligonucleotide comprises at least one non-natural nucleobase.

4. The method of claim 1, wherein the targeting sequence is complementary and specifically hybridizable to a target sequence of a nucleic acid selected from the group consisting of SEQ ID NOS:1, 14, 17, and 27.

5. The method of claim 1, wherein the targeting sequence is complementary and specifically hybridizable to SEQ ID NO:1.

6. The method of claim 1, wherein the targeting sequence is complementary and specifically hybridizable to SEQ ID NO:14.

7. The method of claim 1, wherein the targeting sequence is complementary and specifically hybridizable to SEQ ID NO:17.

8. The method of claim 1, wherein the targeting sequence is complementary and specifically hybridizable to SEQ ID NO: 27.

9. The method of claim 1, wherein the antisense compound hybridizes to at least one of an ARID3a precursor mRNA and an ARID3a mature mRNA.

10. The method of claim 1, wherein the antisense compound further comprises a cell penetrating moiety linked to the oligonucleotide.

11. The method of claim 1, wherein the at least one non-natural internucleoside linkage of the oligonucleotide is selected from the group consisting of phosphoramidites, phosphorodiamidates, phosphorothioates, phosphorodithioates, phosphotriesters, aminoalkylphosphotriesters, alkyl phosphonates, chiral phosphonates, phosphinates, aminoalkylphosphoramidates, thiono-phosphoramidates, thionoalkylphosphonates, thionoalkylphospho-triesters, selenophosphates, boranophosphates, and peptide.

12. The method of claim 1, wherein the oligonucleotide comprises a phosphorodiamidate morpholino backbone.

13. The method of claim 1, wherein the oligonucleotide consists of 18-40 nucleobases.

14. The method of claim 1, wherein the oligonucleotide consists of 20-30 nucleobases.

15. The method of claim 1, wherein the oligonucleotide consists of 22-28 nucleobases.

16. The method of claim 1, wherein the targeting sequence is at least 84% complementary to the target sequence.

17. The method of claim 1, wherein the targeting sequence is at least 90% complementary to the target sequence.

* * * * *

UNITED STATES PATENT AND TRADEMARK OFFICE
CERTIFICATE OF CORRECTION

PATENT NO. : 10,876,116 B2
APPLICATION NO. : 16/317719
DATED : December 29, 2020
INVENTOR(S) : Carol F. Webb, Julie Ward and Michelle Ratliff Page 1 of 1

It is certified that error appears in the above-identified patent and that said Letters Patent is hereby corrected as shown below:

In the Specification
Column 1, Line 20: Delete "A1118836" and replace with -- AI118836 --
Column 1, Line 29: Delete "erythemnatosus" and replace with -- erythematosus --
Column 39, Line 17: Delete "mRNAtranscription" and replace with -- mRNA transcription --
Column 41, Line 22: After "Mass." insert -- ). --
Column 47, Line 34: Delete "10 M" and replace with -- 10 µM --
Column 51, Line 62: Delete "40 µg" and replace with -- 40 pg --
Column 51, Line 62: Delete "300 µg" and replace with -- 300 pg --
Column 51, Line 63: After "0.1 µg to about" insert -- 5 --

Signed and Sealed this
Twenty-third Day of February, 2021

Drew Hirshfeld
*Performing the Functions and Duties of the
Under Secretary of Commerce for Intellectual Property and
Director of the United States Patent and Trademark Office*

```
                        SEQUENCE LISTING

<160> NUMBER OF SEQ ID NOS: 36

<210> SEQ ID NO 1
<211> LENGTH: 32
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 1
atgaaactac aggccgtgat ggagacgctg tt                                   32

<210> SEQ ID NO 2
<211> LENGTH: 29
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 2
cagtttaagc agctctacga actcgacgg                                       29

<210> SEQ ID NO 3
<211> LENGTH: 23
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 3
cagaagcgag ggacacctgt gaa                                             23

<210> SEQ ID NO 4
<211> LENGTH: 34
<212> TYPE: DNA
<213> ORGANISM: Artificial sequence
```

```
<220> FEATURE:
<223> OTHER INFORMATION: Artificial DNA sequence derived from the human
      ARID3a gene

<400> SEQUENCE: 4
ctaagatcaa gaaagaggag gactcagcca tccc                              34

<210> SEQ ID NO 5
<211> LENGTH: 29
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 5
caccctgcgg acccaataca tgaagtacc                                    29

<210> SEQ ID NO 6
<211> LENGTH: 22
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 6
cagcagctgt gcaagcagca gc                                           22

<210> SEQ ID NO 7
<211> LENGTH: 34
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 7
gctgatgcaa cgtgcactcc agcagaactt cctg                              34

<210> SEQ ID NO 8
<211> LENGTH: 53
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 8
agctacccgt gtcctccctg ggcctggccg caagcaccaa tggcagctcc atc          53

<210> SEQ ID NO 9
<211> LENGTH: 23
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 9
attcggatca acagccaagc ctc                                          23

<210> SEQ ID NO 10
<211> LENGTH: 89
<212> TYPE: DNA
<213> ORGANISM: Artificial sequence
<220> FEATURE:
```

<223> OTHER INFORMATION: Artificial DNA sequence derived from the human
    ARID3a gene

<400> SEQUENCE: 10
accctgtggt ggcagcccag gcagcagctg tgcaagcagc agccgcccaa gcagctgtgg    60
ccgcacaggc agctgccctg gaacagctg                                      89

<210> SEQ ID NO 11
<211> LENGTH: 73
<212> TYPE: DNA
<213> ORGANISM: Artificial sequence
<220> FEATURE:
<223> OTHER INFORMATION: Artificial DNA sequence derived from the human
    ARID3a gene

<400> SEQUENCE: 11
aagatggccc tggtggccga tgagcagcaa cggctgatgc aacgtgcact ccagcagaac    60
ttcctggcca tgg                                                       73

<210> SEQ ID NO 12
<211> LENGTH: 28
<212> TYPE: DNA
<213> ORGANISM: Artificial sequence
<220> FEATURE:
<223> OTHER INFORMATION: Artificial DNA sequence derived from the human
    ARID3a gene

<400> SEQUENCE: 12
cggatcaaca gccaagcctc cgaaagcc                                       28

<210> SEQ ID NO 13
<211> LENGTH: 35
<212> TYPE: DNA
<213> ORGANISM: Artificial sequence
<220> FEATURE:
<223> OTHER INFORMATION: Artificial DNA sequence derived from the human
    ARID3a gene

<400> SEQUENCE: 13
ggcatcatgt acacaggagt tctgtttgct cagcc                               35

<210> SEQ ID NO 14
<211> LENGTH: 34
<212> TYPE: DNA
<213> ORGANISM: Artificial sequence
<220> FEATURE:
<223> OTHER INFORMATION: Artificial DNA sequence derived from the human
    ARID3a gene

<400> SEQUENCE: 14
ctccacatct acctcaaata actcgttgcc ttaa                                34

<210> SEQ ID NO 15
<211> LENGTH: 35
<212> TYPE: DNA
<213> ORGANISM: Artificial sequence
<220> FEATURE:
<223> OTHER INFORMATION: Artificial DNA sequence derived from the human
    ARID3a gene

<400> SEQUENCE: 15
aggacatggc ctccgacgag gacatgtgag ttggg                               35

<210> SEQ ID NO 16
<211> LENGTH: 50

```
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 16
gactcctgcc ctctgctcac cccaggaagc ccaaatggga ggaggaggag              50

<210> SEQ ID NO 17
<211> LENGTH: 36
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 17
gacttacgag gagcagttta agcaggtgag tgggcg                             36

<210> SEQ ID NO 18
<211> LENGTH: 43
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 18
acccatcccc tctccaccct cacagctcta cgaactcgac ggg                     43

<210> SEQ ID NO 19
<211> LENGTH: 41
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 19
ttgttcagct tcatgcagaa gcgaggtgag ccctctgccc c                       41

<210> SEQ ID NO 20
<211> LENGTH: 50
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 20
acctccctct cgccccttcc cccagggaca cctgtgaacc gcatccccat              50

<210> SEQ ID NO 21
<211> LENGTH: 50
<212> TYPE: DNA
<213> ORGANISM: Artificial sequence
<220> FEATURE:
<223> OTHER INFORMATION: Artificial DNA sequence derived from the human
      ARID3a gene

<400> SEQUENCE: 21
agtgcagcct tcaccctgcg gacccagtga gtgcggacgg ttgtgccgag              50

<210> SEQ ID NO 22
<211> LENGTH: 50
<212> TYPE: DNA
```

<213> ORGANISM: Artificial sequence
<220> FEATURE:
<223> OTHER INFORMATION: Artificial DNA sequence derived from the human ARID3a gene

<400> SEQUENCE: 22
tcctcttccc tcgtcccacc cacagataca tgaagtacct gtacccctac        50

<210> SEQ ID NO 23
<211> LENGTH: 34
<212> TYPE: DNA
<213> ORGANISM: Artificial sequence
<220> FEATURE:
<223> OTHER INFORMATION: Artificial DNA sequence derived from the human ARID3a gene

<400> SEQUENCE: 23
ccctaagatc aagaaaggta agggcctgta tggg        34

<210> SEQ ID NO 24
<211> LENGTH: 28
<212> TYPE: DNA
<213> ORGANISM: Artificial sequence
<220> FEATURE:
<223> OTHER INFORMATION: Artificial DNA sequence derived from the human ARID3a gene

<400> SEQUENCE: 24
gggaggagga ctcagccatc cccatcac        28

<210> SEQ ID NO 25
<211> LENGTH: 50
<212> TYPE: DNA
<213> ORGANISM: Artificial sequence
<220> FEATURE:
<223> OTHER INFORMATION: Artificial DNA sequence derived from the human ARID3a gene

<400> SEQUENCE: 25
atgagcattc ggatcaacag ccaaggtact gccctcgtgc ccagacccgc        50

<210> SEQ ID NO 26
<211> LENGTH: 50
<212> TYPE: DNA
<213> ORGANISM: Artificial sequence
<220> FEATURE:
<223> OTHER INFORMATION: Artificial DNA sequence derived from the human ARID3a gene

<400> SEQUENCE: 26
aactaatttg ttcttcttcc cacagcctcc gaaagccgcc aggactctgc        50

<210> SEQ ID NO 27
<211> LENGTH: 49
<212> TYPE: DNA
<213> ORGANISM: Artificial sequence
<220> FEATURE:
<223> OTHER INFORMATION: Artificial DNA sequence derived from the human ARID3a gene

<400> SEQUENCE: 27
gagatcaacg gcatcatgta cacaggtagg accccctgagc cacgccctg        49

<210> SEQ ID NO 28
<211> LENGTH: 46
<212> TYPE: DNA
<213> ORGANISM: Artificial sequence
<220> FEATURE:
<223> OTHER INFORMATION: Artificial DNA sequence derived from the human
     ARID3a gene

<400> SEQUENCE: 28
catatgtctt ctgttcttgc cttaggagtt ctgtttgctc agccgc          46

<210> SEQ ID NO 29
<211> LENGTH: 25
<212> TYPE: DNA
<213> ORGANISM: Artificial sequence
<220> FEATURE:
<223> OTHER INFORMATION: Artificial nucleobase sequence of
     phosphorodiamidate morpholino
     oligomer

<400> SEQUENCE: 29
tctccatcac ggcctgtagt ttcat          25

<210> SEQ ID NO 30
<211> LENGTH: 22
<212> TYPE: DNA
<213> ORGANISM: Artificial sequence
<220> FEATURE:
<223> OTHER INFORMATION: Artificial nucleobase sequence of
     phosphorodiamidate morpholino oligomer

<400> SEQUENCE: 30
cacaaccgtc cgccactcac tg          22

<210> SEQ ID NO 31
<211> LENGTH: 20
<212> TYPE: DNA
<213> ORGANISM: Artificial sequence
<220> FEATURE:
<223> OTHER INFORMATION: Forward primer for a human ARID3a exon

<400> SEQUENCE: 31
agctgcagcc gcctgaccac          20

<210> SEQ ID NO 32
<211> LENGTH: 20
<212> TYPE: DNA
<213> ORGANISM: Artificial sequence
<220> FEATURE:
<223> OTHER INFORMATION: Reverse primer for a human ARID3a exon (paired
     with SEQ ID NO:31)

<400> SEQUENCE: 32
tgttgggagc agaggttggc          20

<210> SEQ ID NO 33
<211> LENGTH: 19
<212> TYPE: DNA
<213> ORGANISM: Artificial sequence
<220> FEATURE:
<223> OTHER INFORMATION: Forward primer for a human ARID3a exon

<400> SEQUENCE: 33
gtggcgtgag atcaccaag          19

<210> SEQ ID NO 34
<211> LENGTH: 19
<212> TYPE: DNA
<213> ORGANISM: Artificial sequence
<220> FEATURE:
<223> OTHER INFORMATION: Reverse primer for a human ARID3a exon (paired with SEQ ID NO:33)

<400> SEQUENCE: 34
cagaactcct gtgtacatg                                                19

<210> SEQ ID NO 35
<211> LENGTH: 20
<212> TYPE: DNA
<213> ORGANISM: Artificial sequence
<220> FEATURE:
<223> OTHER INFORMATION: Forward primer for human IFN-alpha

<400> SEQUENCE: 35
cctggcacaa atgaggagaa                                               20

<210> SEQ ID NO 36
<211> LENGTH: 24
<212> TYPE: DNA
<213> ORGANISM: Artificial sequence
<220> FEATURE:
<223> OTHER INFORMATION: Reverse primer for human IFN-alpha (paired with
      SEQ ID NO:35)

<400> SEQUENCE: 36
agctgctggt aaagttcagt atag                                          24